United States Patent
Lee et al.

(10) Patent No.: US 11,997,927 B2
(45) Date of Patent: May 28, 2024

(54) COMPOUND AND ORGANIC LIGHT EMITTING DIODE COMPRISING SAME

(71) Applicant: LG CHEM, LTD., Seoul (KR)

(72) Inventors: Jungha Lee, Daejeon (KR); Dong Hoon Lee, Daejeon (KR); Boon Jae Jang, Daejeon (KR); Min Woo Jung, Daejeon (KR); Su Jin Han, Daejeon (KR); Seulchan Park, Daejeon (KR); Sunghyun Hwang, Daejeon (KR)

(73) Assignee: LG Chem, Ltd., Seoul (KR)

( * ) Notice: Subject to any disclaimer, the term of this patent is extended or adjusted under 35 U.S.C. 154(b) by 668 days.

(21) Appl. No.: 17/262,622

(22) PCT Filed: Oct. 4, 2019

(86) PCT No.: PCT/KR2019/013051
§ 371 (c)(1),
(2) Date: Jan. 22, 2021

(87) PCT Pub. No.: WO2020/071860
PCT Pub. Date: Apr. 9, 2020

(65) Prior Publication Data
US 2021/0376257 A1    Dec. 2, 2021

(30) Foreign Application Priority Data
Oct. 4, 2018    (KR) ........................ 10-2018-0118270

(51) Int. Cl.
*H10K 85/60*    (2023.01)
*C07D 405/14*    (2006.01)
(Continued)

(52) U.S. Cl.
CPC ....... *H10K 85/6574* (2023.02); *C07D 405/14* (2013.01); *C07D 409/14* (2013.01);
(Continued)

(58) Field of Classification Search
CPC ................ C07D 405/14; C07D 409/14; H10K 85/6572; H10K 85/6574; H10K 85/6576
See application file for complete search history.

(56) References Cited

U.S. PATENT DOCUMENTS

| 2004/0251816 A1 | 12/2004 | Leo et al. |
| 2015/0159084 A1 | 6/2015 | Cho et al. |

(Continued)

FOREIGN PATENT DOCUMENTS

| CN | 109563065 | 4/2019 |
| KR | 10-2012-0116269 | 10/2012 |

(Continued)

OTHER PUBLICATIONS

Machine-generated English-language translation of KR-20190078040-A.*

(Continued)

*Primary Examiner* — Vu A Nguyen
(74) *Attorney, Agent, or Firm* — Bryan Cave Leighton Paisner LLP

(57) ABSTRACT

Provided is a compound of Chemical Formula 1:

(Continued)

wherein:
X is O or S;
L is a direct bond, a substituted or unsubstituted arylene group, or a substituted or unsubstituted heteroarylene group;
Ar1 is a substituted or unsubstituted aryl group or a substituted or unsubstituted heteroaryl group;
Ar2 is a substituted or unsubstituted aryl group having 6 to 30 carbon atoms;
R1 to R8 are the same as or different from each other, and each independently is hydrogen, a substituted or unsubstituted aryl group, or a substituted or unsubstituted heteroaryl group; and
m and n are each an integer of 0 to 7, and when m is 2 or greater, R7s are the same as or different from each other, and when n is 2 or greater, R8s are the same as or different from each other,
and an organic light emitting device including the same.

9 Claims, 1 Drawing Sheet

(51) Int. Cl.
| | | |
|---|---|---|
| $C07D\ 409/14$ | (2006.01) | |
| $C09K\ 11/06$ | (2006.01) | |
| $H10K\ 50/11$ | (2023.01) | |
| $H10K\ 50/15$ | (2023.01) | |
| $H10K\ 50/17$ | (2023.01) | |
| $H10K\ 101/10$ | (2023.01) | |

(52) U.S. Cl.
CPC ............ *C09K 11/06* (2013.01); *H10K 85/615* (2023.02); *H10K 85/622* (2023.02); *H10K 85/6572* (2023.02); *H10K 85/6576* (2023.02); *C07B 2200/05* (2013.01); *C09K 2211/1018* (2013.01); *H10K 50/11* (2023.02); *H10K 50/15* (2023.02); *H10K 50/17* (2023.02); *H10K 2101/10* (2023.02)

(56) References Cited

U.S. PATENT DOCUMENTS

| | | |
|---|---|---|
| 2015/0221874 A1 | 8/2015 | Kim et al. |
| 2015/0318487 A1 | 11/2015 | Ito et al. |
| 2016/0072074 A1 | 3/2016 | Choi et al. |
| 2016/0163995 A1 | 6/2016 | Kang et al. |
| 2017/0098784 A1 | 4/2017 | Kim et al. |
| 2018/0138425 A1 | 5/2018 | Ma et al. |
| 2019/0189929 A1 | 6/2019 | Heo et al. |
| 2022/0336754 A1* | 10/2022 | Parham ................ C07D 209/94 |

FOREIGN PATENT DOCUMENTS

| | | |
|---|---|---|
| KR | 10-2014-0012440 | 2/2014 |
| KR | 10-2014-0025119 | 3/2014 |
| KR | 10-2014-0039121 | 4/2014 |
| KR | 10-2014-0049227 | 4/2014 |
| KR | 10-2015-0126756 | 11/2015 |
| KR | 10-2015-0135123 | 12/2015 |
| KR | 10-2016-0069934 | 6/2016 |
| KR | 20170121577 | 11/2017 |
| KR | 10-2018-0054490 | 5/2018 |
| WO | 2003-012890 | 2/2003 |
| WO | 2012-141499 | 10/2012 |
| WO | 2014-061991 | 4/2014 |

OTHER PUBLICATIONS

Machine-generated English-language translation of KR-20190073009-A.*

* cited by examiner

【FIG. 1】
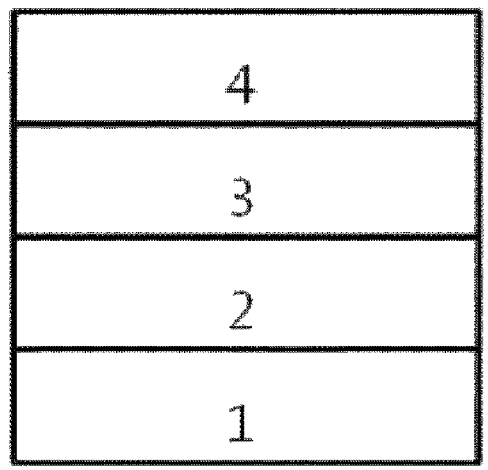
【FIG. 2】
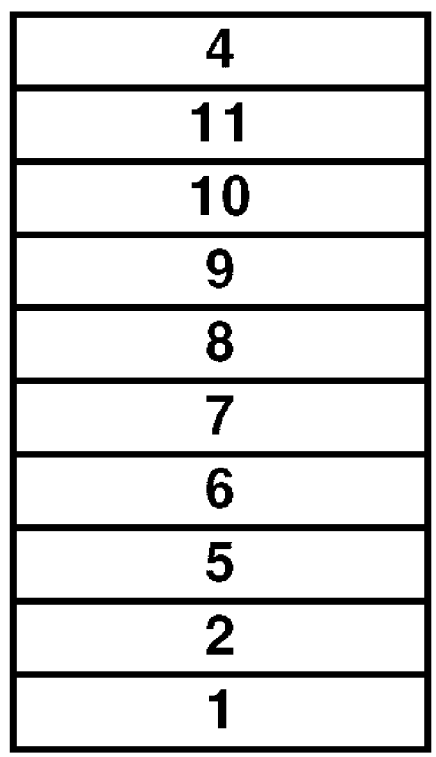

COMPOUND AND ORGANIC LIGHT EMITTING DIODE COMPRISING SAME

CROSS-REFERENCE TO RELATED APPLICATION (S)

This application is a National Stage Application of International Application No. PCT/KR2019/013051 filed on Oct. 4, 2019, which claims priority to and the benefits of Korean Patent Application No. 10-2018-0118270, filed with the Korean Intellectual Property Office on Oct. 4, 2018, the entire contents of which are incorporated herein by reference.

TECHNICAL FIELD

The present specification relates to a compound, and an organic light emitting device including the same.

BACKGROUND ART

An organic light emitting device has a structure disposing an organic thin film between two electrodes. When a voltage is applied to an organic light emitting device having such a structure, electrons and holes injected from the two electrodes bind and pair in the organic thin film, and light emits as these annihilate. The organic thin film can be formed in a single layer or a multilayer as necessary.

A material of the organic thin film can have a light emitting function as necessary. For example, as a material of the organic thin film, compounds capable of forming a light emitting layer themselves alone can be used, or compounds capable of performing a role of a host or a dopant of a host-dopant-based light emitting layer can also be used. In addition thereto, compounds capable of performing roles of hole injection, hole transfer, electron blocking, hole blocking, electron transfer, electron injection or the like can also be used as a material of the organic thin film.

Development of an organic thin film material has been continuously required for enhancing performance, lifetime or efficiency of an organic light emitting device.

BRIEF DESCRIPTION

Technical Problem

The present specification is directed to providing a compound, and an organic light emitting device including the same.

Technical Solution

One embodiment of the present specification provides a compound of Chemical Formula 1:

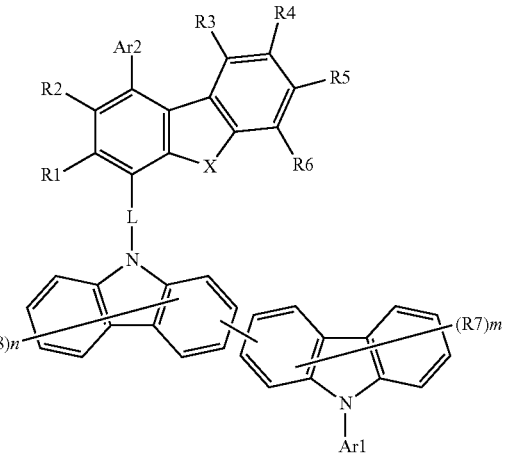

Chemical Formula 1 wherein, in Chemical Formula 1:

X is O or S;

L is a direct bond, a substituted or unsubstituted arylene group, or a substituted or unsubstituted heteroarylene group;

Ar1 is a substituted or unsubstituted aryl group or a substituted or unsubstituted heteroaryl group;

Ar2 is a substituted or unsubstituted aryl group having 6 to 30 carbon atoms;

R1 to R8 are the same as or different from each other, and each independently is hydrogen, a substituted or unsubstituted aryl group, or a substituted or unsubstituted heteroaryl group; and m and n are each an integer of 0 to 7, and when m is 2 or greater, the R7s are the same as or different from each other, and when n is 2 or greater, the R8s are the same as or different from each other.

Another embodiment of the present application provides an organic light emitting device including a first electrode; a second electrode provided opposite to the first electrode; and one or more organic material layers provided between the first electrode and the second electrode, wherein one or more layers of the organic material layers include the compound described above.

Advantageous Effects

A compound according to one embodiment of the present application is, when used in an organic light emitting device, capable of increasing luminance, increasing a lifetime, lowering a driving voltage and enhancing light efficiency of the organic light emitting device, and enhancing device lifetime properties by thermal stability of the compound.

DESCRIPTION OF DRAWINGS

FIG. 1 illustrates an example of an organic light emitting device in which a substrate (1), an anode (2), an organic material layer (3) and a cathode (4) are consecutively laminated.

FIG. 2 illustrates an example of an organic light emitting device in which a substrate (1), an anode (2), a hole injection layer (5), a hole transfer layer (6), an electron blocking layer (7), a light emitting layer (8), a hole blocking layer (9), an electron transfer layer (10), an electron injection layer (11) and a cathode (4) are consecutively laminated.

REFERENCE NUMERALS

1: Substrate
2: Anode
3: Organic Material Layer
4: Cathode
5: Hole Injection Layer
6: Hole Transfer Layer
7: Electron Blocking Layer
8: Light Emitting Layer
9: Hole Blocking Layer
10: Electron Transfer Layer
11: Electron Injection Layer

DETAILED DESCRIPTION

Hereinafter, the present specification will be described in more detail.

One embodiment of the present specification provides a compound of Chemical Formula 1.

Examples of substituents in the present specification will be described below, however, the substituents are not limited thereto.

The term "substitution" means a hydrogen atom bonding to a carbon atom of a compound is changed to another substituent, and the position of substitution is not limited as long as it is a position at which the hydrogen atom is substituted, that is, a position at which a substituent can substitute, and when two or more substituents substitute, the two or more substituents can be the same as or different from each other.

In the present specification, the term "substituted or unsubstituted" means being substituted with one, two or more substituents selected from the group consisting of deuterium; a halogen group; a nitrile group; an alkyl group; a cycloalkyl group; an alkoxy group; an aryl group; and a heteroaryl group, or being substituted with a substituent linking two or more substituents of the substituents illustrated above, or having no substituents. For example, a "substituent linking two or more substituents" can include a biphenyl group. In other words, a biphenyl group can be an aryl group, or can be interpreted as a substituent linking two phenyl groups.

In the present specification, examples of the halogen group can include fluorine, chlorine, bromine or iodine.

In the present specification, the alkyl group can be linear or branched, and although not particularly limited thereto, the number of carbon atoms is preferably from 1 to 50. Specific examples thereof can include methyl, ethyl, propyl, n-propyl, isopropyl, butyl, n-butyl, isobutyl, tert-butyl, sec-butyl, 1-methyl-butyl, 1-ethyl-butyl, pentyl, n-pentyl, isopentyl, neopentyl, tert-pentyl, hexyl, n-hexyl, 1-methylpentyl, 2-methylpentyl, 4-methyl-2-pentyl, 3,3-dimethylbutyl, 2-ethylbutyl, heptyl, n-heptyl, 1-methylhexyl, cyclopentylmethyl, cyclohexylmethyl, octyl, n-octyl, tert-octyl, 1-methylheptyl, 2-ethylhexyl, 2-propylpentyl, n-nonyl, 2,2-dimethylheptyl, 1-ethylpropyl, 1,1-dimethylpropyl, isohexyl, 2-methylpentyl, 4-methylhexyl, 5-methylhexyl and the like, but are not limited thereto.

In the present specification, the cycloalkyl group is not particularly limited, but preferably has 3 to 30 carbon atoms. Specific examples thereof can include cyclopropyl, cyclobutyl, cyclopentyl, 3-methylcyclopentyl, 2,3-dimethylcyclopentyl, cyclohexyl, 3-methylcyclohexyl, 4-methylcyclohexyl, 2,3-dimethylcyclohexyl, 3,4,5-trimethyl-cyclohexyl, 4-tert-butylcyclohexyl, cycloheptyl, cyclooctyl and the like, but are not limited thereto.

In the present specification, the alkoxy group can be linear, branched or cyclic. The number of carbon atoms of the alkoxy group is not particularly limited, but is preferably from 1 to 30. Specific examples thereof can include methoxy, ethoxy, n-propoxy, isopropoxy, i-propyloxy, n-butoxy, isobutoxy, tert-butoxy, sec-butoxy, n-pentyloxy, neopentyloxy, isopentyloxy, n-hexyloxy, 3,3-dimethyl-butyloxy, 2-ethylbutyloxy, n-octyloxy, n-nonyloxy, n-decyloxy, benzyloxy, p-methylbenzyloxy and the like, but are not limited thereto.

In the present specification, when the aryl group is a monocyclic aryl group, the number of carbon atoms is not particularly limited, but is preferably from 6 to 30. Specific examples of the monocyclic aryl group can include a phenyl group, a biphenyl group, a terphenyl group and the like, but are not limited thereto.

When the aryl group is a polycyclic aryl group, the number of carbon atoms is not particularly limited, but is preferably from 10 to 24. Specific examples of the polycyclic aryl group can include a naphthyl group, an anthracene group, a phenanthrene group, a pyrenyl group, a perylenyl group, a chrysene group, a fluorene group and the like, but are not limited thereto.

In the present specification, the heteroaryl group is a group including one or more atoms that are not carbon, that is, heteroatoms, and specifically, the heteroatom can include one or more atoms selected from the group consisting of O, N, Se, Si, S and the like. The number of carbon atoms of the heteroaryl group is not particularly limited, but is preferably from 2 to 60 or 2 to 30. Examples of the heteroaryl group can include a thiophene group, a furan group, a pyrrole group, an imidazolyl group, a thiazolyl group, an oxazolyl group, an oxadiazolyl group, a triazolyl group, a pyridyl group, a bipyridyl group, a pyrimidyl group, a triazinyl group, an acridyl group, a pyridazinyl group, a pyrazinyl group, a quinolinyl group, a quinazolinyl group, a quinoxalinyl group, a phthalazinyl group, a pyridopyrimidinyl group, a pyridopyrazinyl group, a pyrazinopyrazinyl group, an isoquinolinyl group, an indole group, a carbazolyl group, a benzoxazolyl group, a benzimidazolyl group, a benzo-thiazolyl group, a benzocarbazolyl group, a dibenzocarbazolyl group, a benzothiophene group, a dibenzothiophene group, a benzofuran group, a dibenzofuran group, a benzosilole group, a dibenzosilole group, a phenanthrolinyl group, an isoxazolyl group, a thiadiazolyl group, a phenothiazinyl group, a phenoxazine group, fused structures thereof, and the like, but are not limited thereto.

In the present specification, the arylene group means the aryl group having two bonding sites, that is, a divalent group. Descriptions on the aryl group provided above can be applied thereto except for those that are each a divalent.

In the present specification, the heteroarylene group means the heteroaryl group having two bonding sites, that is, a divalent group. Descriptions on the heteroaryl group provided above can be applied thereto except for those that are each a divalent.

In one embodiment of the present specification, Chemical Formula 1 is any one of the following Chemical Formula 2 or 3:

Chemical Formula 2
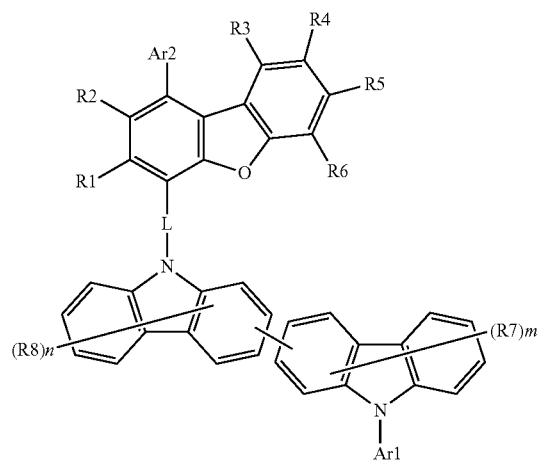
Chemical Formula 3
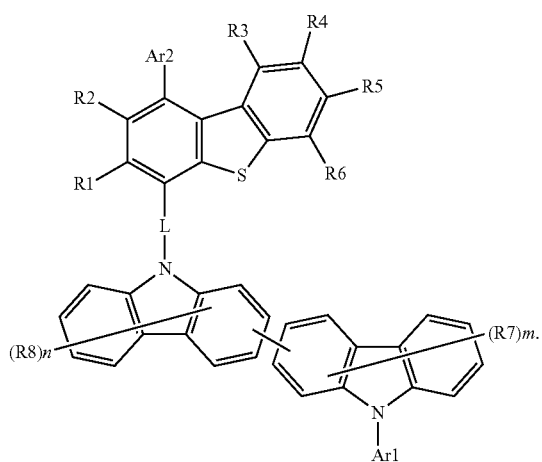
In Chemical Formulae 2 and 3, Ar1, Ar2, L, m, n and R1 to R8 have the same definitions as in Chemical Formula 1.
In one embodiment of the present specification, Chemical Formula 1 is any one of the following Chemical Formulae 4 to 7:
Chemical Formula 4
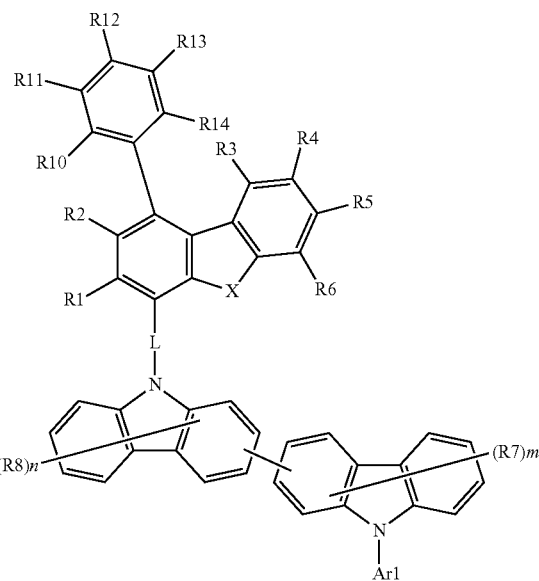
Chemical Formula 5
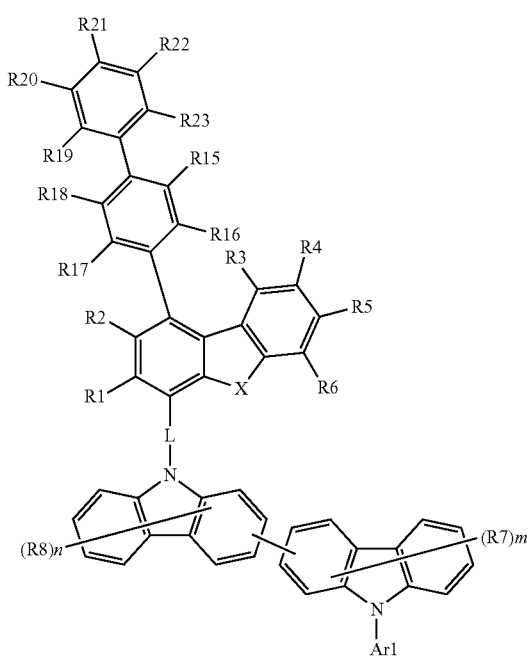

Chemical Formula 6

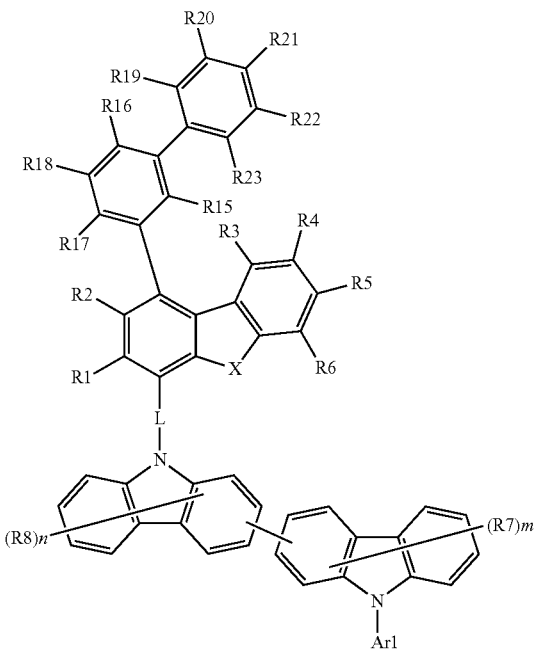

Chemical Formula 7

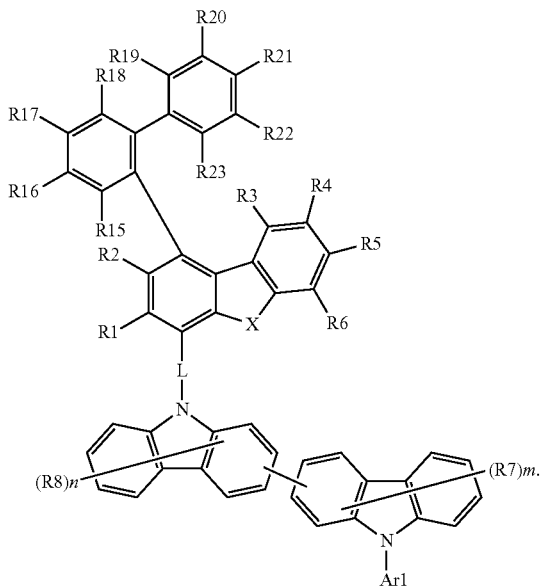

In Chemical Formulae 4 to 7, Ar1, X, L, m, n and R1 to R8 have the same definitions as in Chemical Formula 1, and R10 to R23 are the same as or different from each other, and each independently is hydrogen, deuterium, or a substituted or unsubstituted aryl group.

In one embodiment of the present specification, R10 to R23 are the same as or different from each other, and each independently is hydrogen, deuterium, or a substituted or unsubstituted aryl group having 6 to 30 carbon atoms.

In one embodiment of the present specification, R10 to R23 are the same as or different from each other, and each independently is hydrogen, deuterium, or an aryl group having 6 to 30 carbon atoms.

In one embodiment of the present specification, R10 to R23 are the same as or different from each other, and each independently is hydrogen, deuterium, or an aryl group having 6 to 20 carbon atoms.

In one embodiment of the present specification, R10 to R23 are the same as or different from each other, and each independently is hydrogen, deuterium, or an aryl group having 6 to 10 carbon atoms.

In one embodiment of the present specification, R10 to R23 are the same as or different from each other, and each independently is hydrogen, deuterium, or a phenyl group.

In one embodiment of the present specification, R10 to R14 are the same as or different from each other, and each independently is hydrogen, deuterium, or an aryl group.

In one embodiment of the present specification, R10 to R14 are the same as or different from each other, and each independently is hydrogen, deuterium, or a phenyl group.

In one embodiment of the present specification, R10 to R14 are the same as or different from each other, and each independently is hydrogen or deuterium.

In one embodiment of the present specification, R15 to R23 are the same as or different from each other, and each independently is hydrogen, deuterium, or a phenyl group.

In one embodiment of the present specification, R15 to R23 are hydrogen or deuterium.

In one embodiment of the present specification, Chemical Formula 1 is any one of the following Chemical Formulae 1-1 to 1-12:

Chemical Formula 1-1

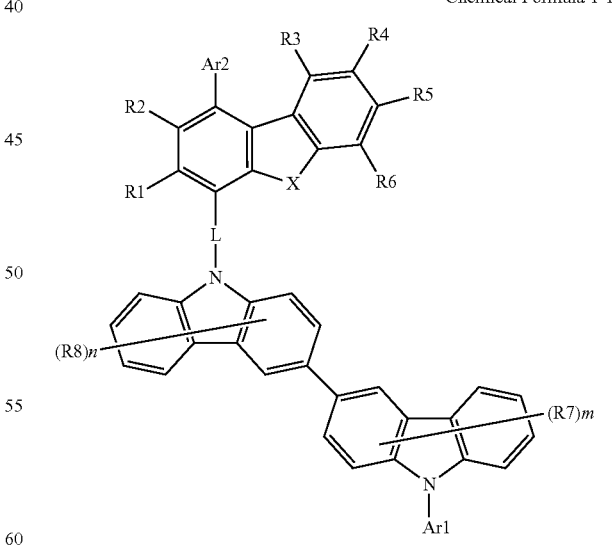

Chemical Formula 1-2
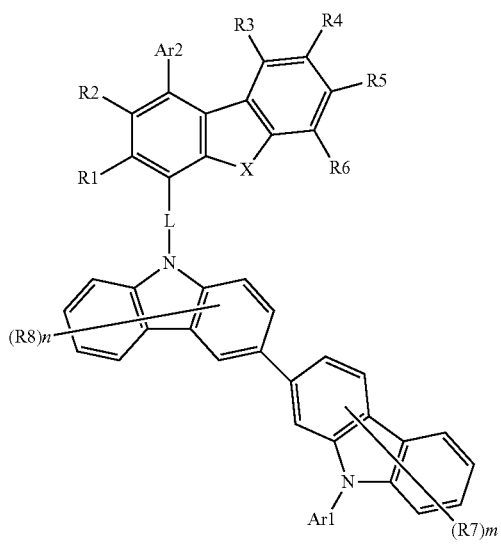
Chemical Formula 1-3
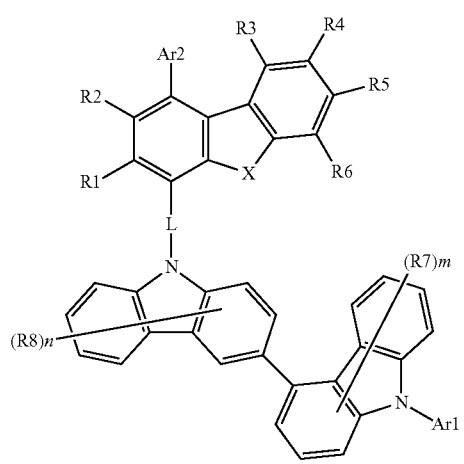
Chemical Formula 1-4
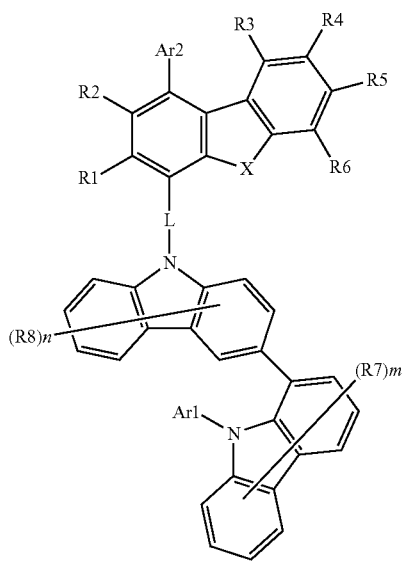
Chemical Formula 1-5
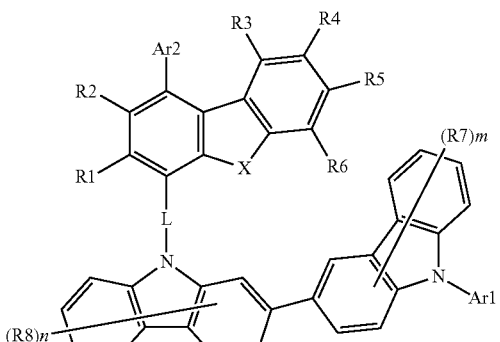
Chemical Formula 1-6
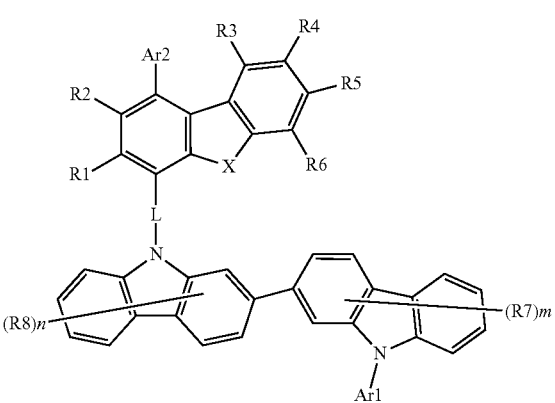
Chemical Formula 1-7
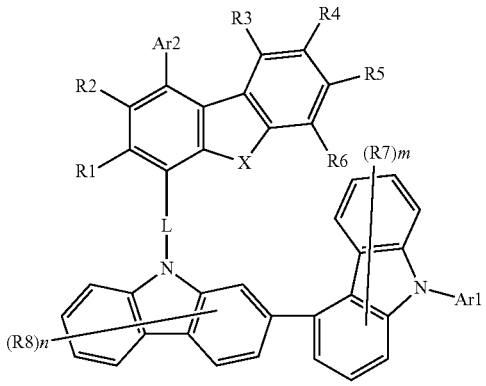

Chemical Formula 1-8
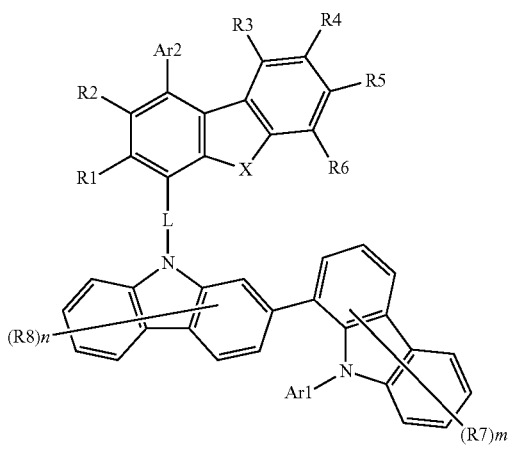
Chemical Formula 1-9
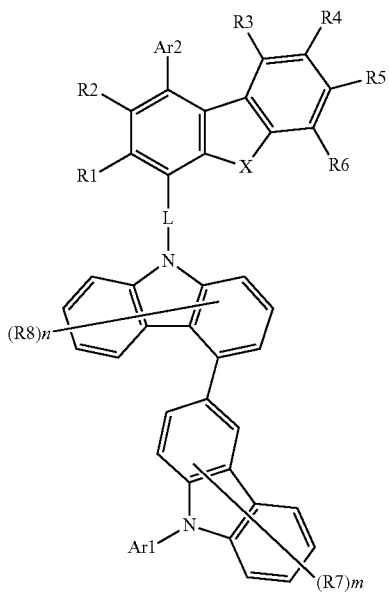
Chemical Formula 1-10
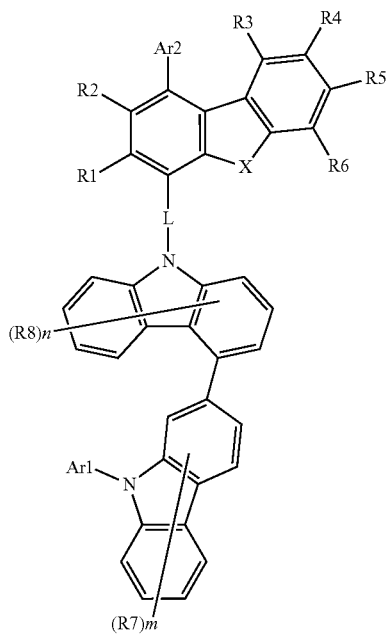
Chemical Formula 1-11
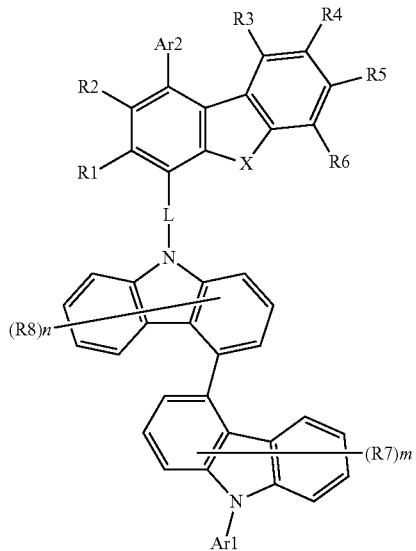

-continued

Chemical Formula 1-12

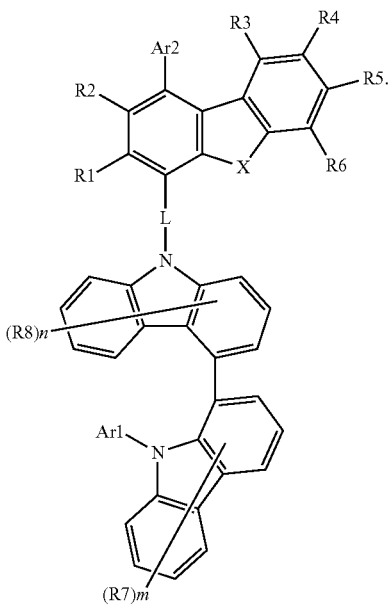

In Chemical Formulae 1-1 to 1-12, Ar1, Ar2, X, L, m, n and R1 to R8 have the same definitions as in Chemical Formula 1.

In one embodiment of the present specification, L is a direct bond, or a substituted or unsubstituted arylene group.

In one embodiment of the present specification, L is a direct bond, or an arylene group.

In one embodiment of the present specification, L is a direct bond, a phenylene group, a biphenylylene group, or a naphthylene group.

In one embodiment of the present specification, L is a direct bond.

The compound having L of Chemical Formula 1 of the present specification being a direct bond is effective in enhancing a lifetime of an organic light emitting device when used in the organic light emitting device.

In one embodiment of the present specification, Ar1 and Ar2 are the same as or different from each other, and each independently is an aryl group unsubstituted or substituted with deuterium, an alkyl group or an aryl group.

In one embodiment of the present specification, Ar1 and Ar2 are the same as or different from each other, and each independently is a substituted or unsubstituted phenyl group, a substituted or unsubstituted biphenyl group, a substituted or unsubstituted naphthyl group, a substituted or unsubstituted triphenylene group, a substituted or unsubstituted phenanthrene group, a substituted or unsubstituted fluorene group, or a substituted or unsubstituted spirobifluorene group.

In one embodiment of the present specification, Ar1 and Ar2 are the same as or different from each other, and each independently a substituted or unsubstituted phenyl group, a substituted or unsubstituted biphenyl group, a substituted or unsubstituted naphthyl group, a substituted or unsubstituted triphenylene group, a substituted or unsubstituted phenanthrene group, or a substituted or unsubstituted fluorene group.

In one embodiment of the present specification, Ar1 and Ar2 are the same as or different from each other, and each independently is a phenyl group that is unsubstituted or substituted with deuterium or an aryl group; a biphenyl group that is unsubstituted or substituted with deuterium or an aryl group; a naphthyl group that is unsubstituted or substituted with deuterium or an aryl group; a triphenylene group that is unsubstituted or substituted with deuterium or an aryl group; a phenanthrene group that is unsubstituted or substituted with deuterium or an aryl group; or a fluorene group that is unsubstituted or substituted with deuterium, an aryl group or an alkyl group.

In one embodiment of the present specification, Ar1 and Ar2 are the same as or different from each other, and each independently is a phenyl group that is unsubstituted or substituted with deuterium or a phenyl group; a biphenyl group that is unsubstituted or substituted with deuterium or a phenyl group; a naphthyl group that is unsubstituted or substituted with deuterium or a phenyl group; a triphenylene group that is unsubstituted or substituted with deuterium or a phenyl group; a phenanthrene group that is unsubstituted or substituted with deuterium or a phenyl group; or a fluorene group that is unsubstituted or substituted with deuterium, a phenyl group or a methyl group.

In one embodiment of the present specification, Ar1 and Ar2 are the same as or different from each other, and each independently is a phenyl group that is unsubstituted or substituted with deuterium; a biphenyl group; a naphthyl group; a triphenylene group; a phenanthrene group; or a fluorene group that is unsubstituted or substituted with an alkyl group.

In one embodiment of the present specification, Ar1 and Ar2 are the same as or different from each other, and each independently is a phenyl group that is unsubstituted or substituted with deuterium; a biphenyl group; a naphthyl group; a triphenylene group; a phenanthrene group; or a fluorene group that is unsubstituted or substituted with a methyl group. In one embodiment of the present specification, Ar1 is a substituted or unsubstituted phenyl group, a substituted or unsubstituted biphenyl group, a substituted or unsubstituted naphthyl group, a substituted or unsubstituted triphenylene group, a substituted or unsubstituted phenanthrene group, a substituted or unsubstituted fluorene group, or a substituted or unsubstituted spirobifluorene group.

In one embodiment of the present specification, Ar1 is a substituted or unsubstituted phenyl group, a substituted or unsubstituted biphenyl group, a substituted or unsubstituted naphthyl group, a substituted or unsubstituted triphenylene group, a substituted or unsubstituted phenanthrene group, or a substituted or unsubstituted fluorene group.

In one embodiment of the present specification, Ar1 is a phenyl group that is unsubstituted or substituted with deuterium or an aryl group; a biphenyl group that is unsubstituted or substituted with deuterium or an aryl group; a naphthyl group that is unsubstituted or substituted with deuterium or an aryl group; a triphenylene group that is unsubstituted or substituted with deuterium or an aryl group; a phenanthrene group that is unsubstituted or substituted with deuterium or an aryl group; or a fluorene group that is unsubstituted or substituted with deuterium, an aryl group or an alkyl group.

In one embodiment of the present specification, Ar1 is a phenyl group that is unsubstituted or substituted with deuterium or a phenyl group; a biphenyl group that is unsubstituted or substituted with deuterium or a phenyl group; a naphthyl group that is unsubstituted or substituted with deuterium or a phenyl group; a triphenylene group that is unsubstituted or substituted with deuterium or a phenyl group; a phenanthrene group that is unsubstituted or substituted with deuterium or a phenyl group; or a fluorene group that is unsubstituted or substituted with deuterium, a phenyl group or a methyl group.

In one embodiment of the present specification, Ar1 is a phenyl group that is unsubstituted or substituted with deuterium; a biphenyl group; a naphthyl group; a triphenylene group; a phenanthrene group; or a fluorene group that is unsubstituted or substituted with an alkyl group.

In one embodiment of the present specification, Ar1 is a phenyl group that is unsubstituted or substituted with deuterium; a biphenyl group; a naphthyl group; a triphenylene group; a phenanthrene group; or a fluorene group that is unsubstituted or substituted with a methyl group.

In one embodiment of the present specification, Ar1 is a phenyl group that is unsubstituted or substituted with deuterium; or a biphenyl group that is unsubstituted or substituted with deuterium.

In one embodiment of the present specification, Ar2 is a substituted or unsubstituted phenyl group, a substituted or unsubstituted biphenyl group, a substituted or unsubstituted naphthyl group, a substituted or unsubstituted triphenylene group, a substituted or unsubstituted phenanthrene group, a substituted or unsubstituted fluorene group, or a substituted or unsubstituted spirobifluorene group.

In one embodiment of the present specification, Ar2 is a substituted or unsubstituted phenyl group, a substituted or unsubstituted biphenyl group, a substituted or unsubstituted naphthyl group, a substituted or unsubstituted triphenylene group, a substituted or unsubstituted phenanthrene group, or a substituted or unsubstituted fluorene group.

In one embodiment of the present specification, Ar2 is a phenyl group that is unsubstituted or substituted with deuterium or an aryl group; a biphenyl group that is unsubstituted or substituted with deuterium or an aryl group; a naphthyl group that is unsubstituted or substituted with deuterium or an aryl group; a triphenylene group that is unsubstituted or substituted with deuterium or an aryl group; a phenanthrene group that is unsubstituted or substituted with deuterium or an aryl group; or a fluorene group that is unsubstituted or substituted with deuterium, an aryl group or an alkyl group.

In one embodiment of the present specification, Ar2 is a phenyl group that is unsubstituted or substituted with deuterium or a phenyl group; a biphenyl group that is unsubstituted or substituted with deuterium or a phenyl group; a naphthyl group that is unsubstituted or substituted with deuterium or a phenyl group; a triphenylene group that is unsubstituted or substituted with deuterium or a phenyl group; a phenanthrene group that is unsubstituted or substituted with deuterium or a phenyl group; or a fluorene group that is unsubstituted or substituted with deuterium, a phenyl group or a methyl group.

In one embodiment of the present specification, Ar2 is a phenyl group that is unsubstituted or substituted with deuterium; a biphenyl group; a naphthyl group; a triphenylene group; a phenanthrene group; or a fluorene group that is unsubstituted or substituted with an alkyl group.

In one embodiment of the present specification, Ar2 is a phenyl group that is unsubstituted or substituted with deuterium; a biphenyl group; a naphthyl group; a triphenylene group; a phenanthrene group; or a fluorene group that is unsubstituted or substituted with a methyl group.

In one embodiment of the present specification, Ar2 is a phenyl group; a biphenyl group; or a naphthyl group.

In one embodiment of the present specification, R1 to R6 and R8 are the same as or different from each other, and each independently is hydrogen or an aryl group.

In one embodiment of the present specification, R1 to R6 and R8 are the same as or different from each other, and each independently is hydrogen, a phenyl group, a biphenyl group, or a naphthyl group.

In one embodiment of the present specification, R1 to R6 and R8 are the same as or different from each other, and each independently is hydrogen or a phenyl group.

In one embodiment of the present specification, R1 to R6 and R8 are hydrogen.

In one embodiment of the present specification, R7 is hydrogen or an aryl group.

In one embodiment of the present specification, R7 is hydrogen, a phenyl group, a biphenyl group, or a naphthyl group.

In one embodiment of the present specification, R7 is hydrogen or a phenyl group.

In one embodiment of the present specification, the compound of Chemical Formula 1 is selected from among the following compounds:

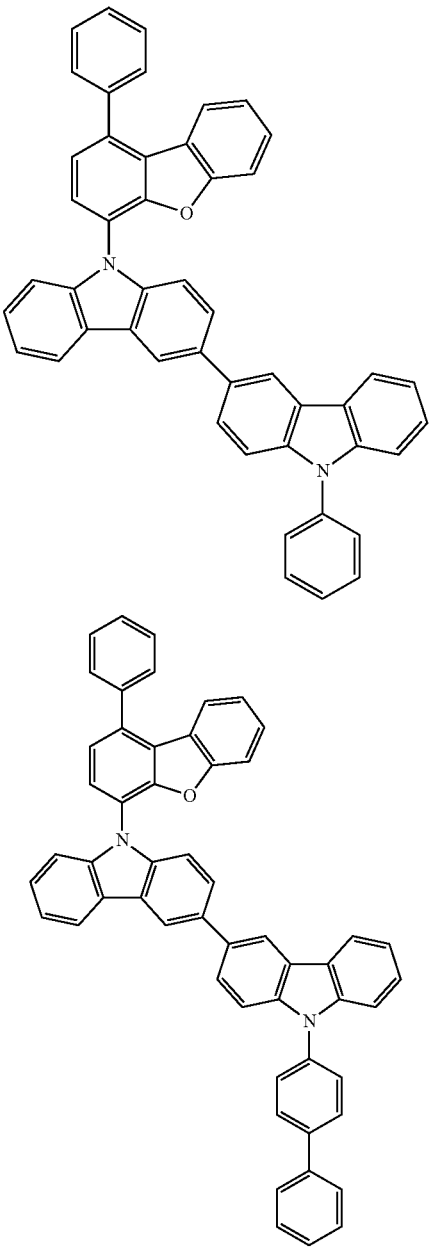

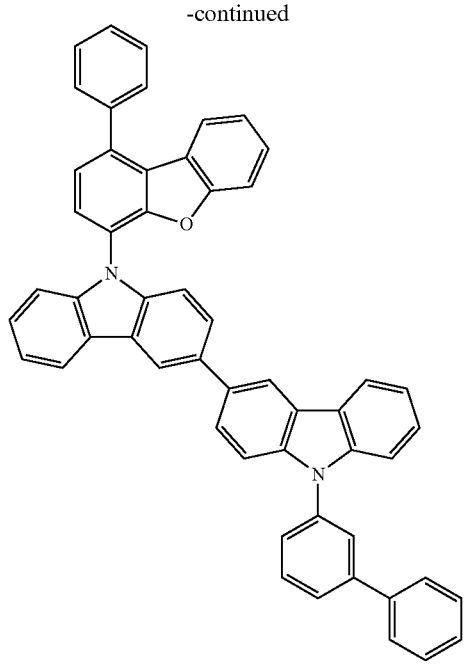
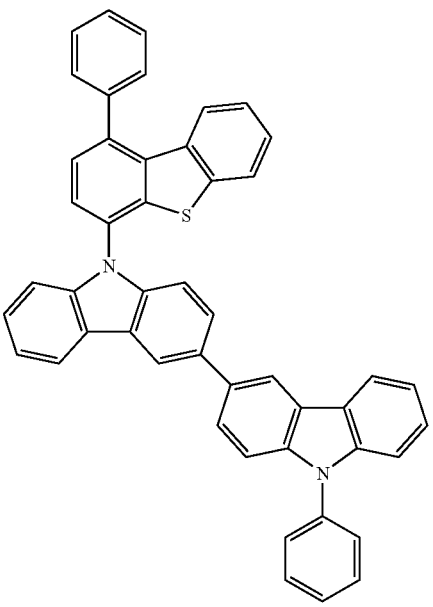
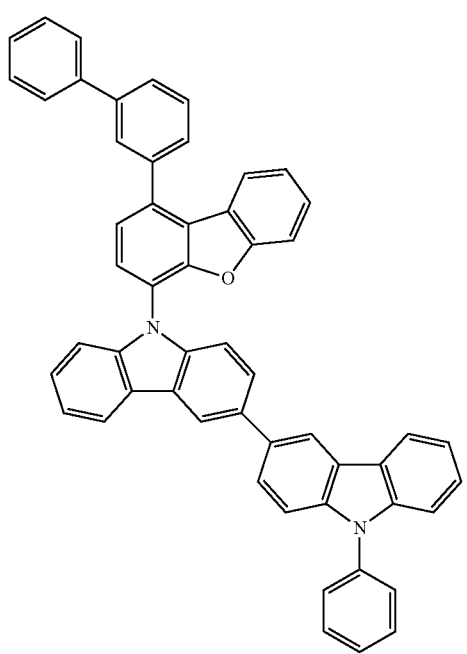
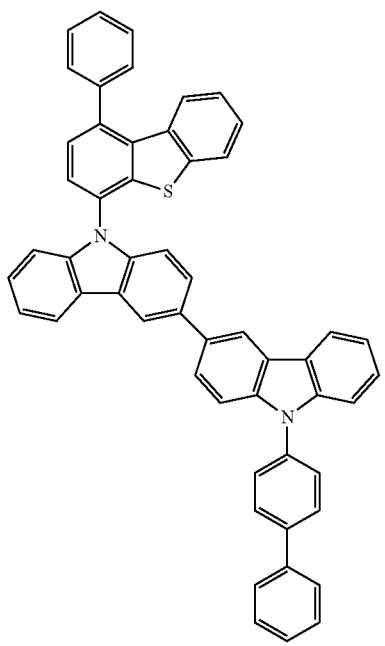

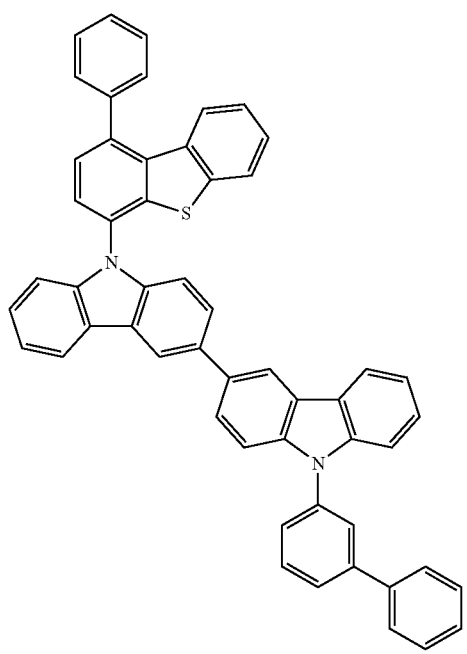
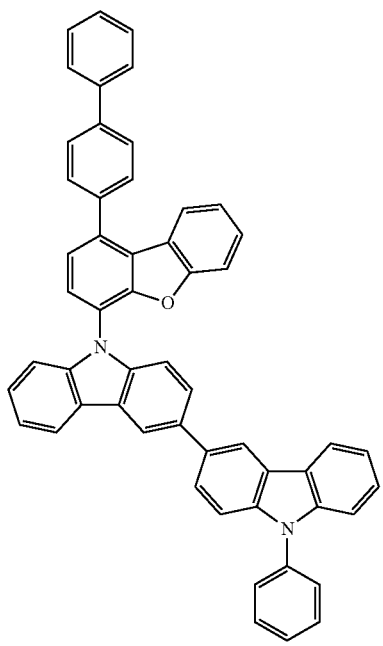
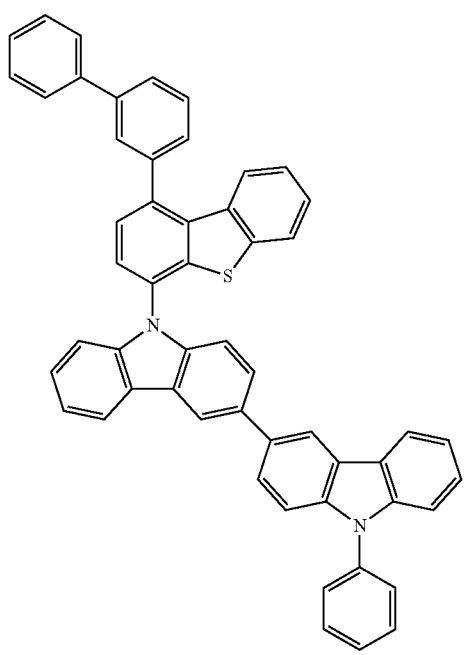
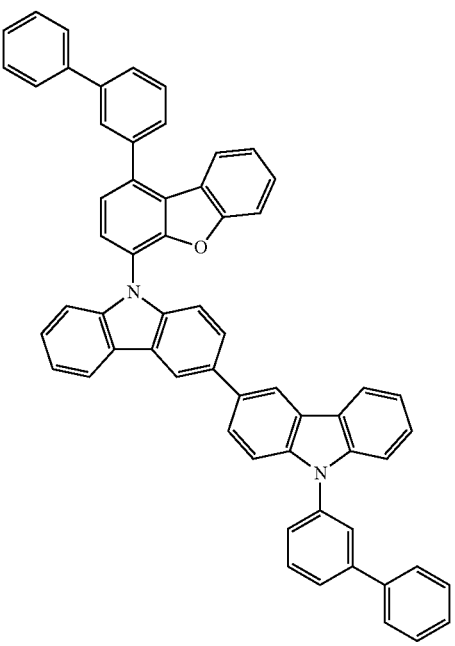

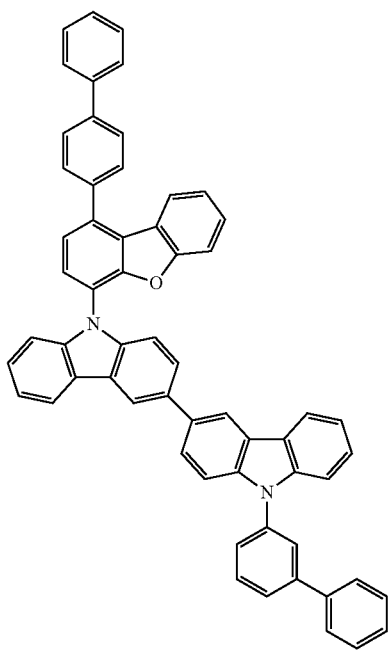
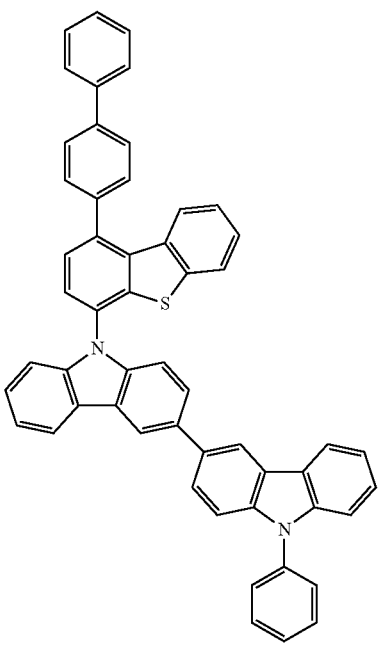
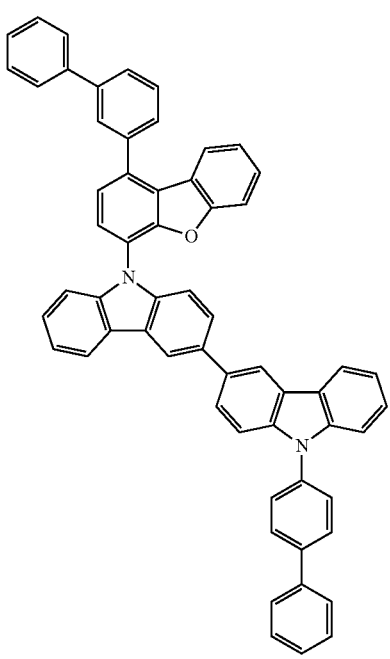
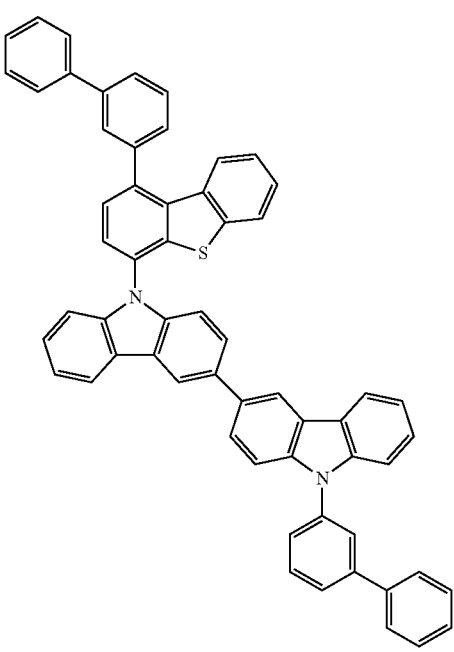

23
-continued
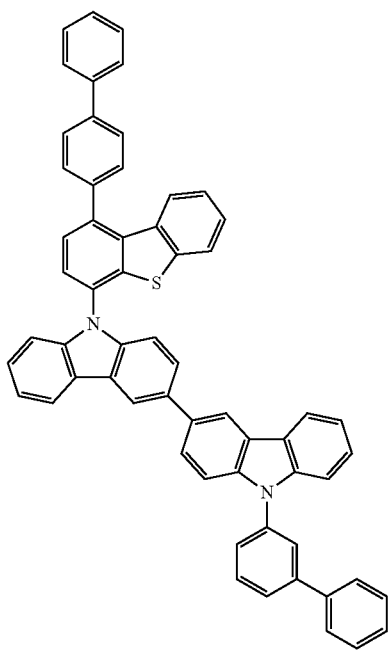
24
-continued
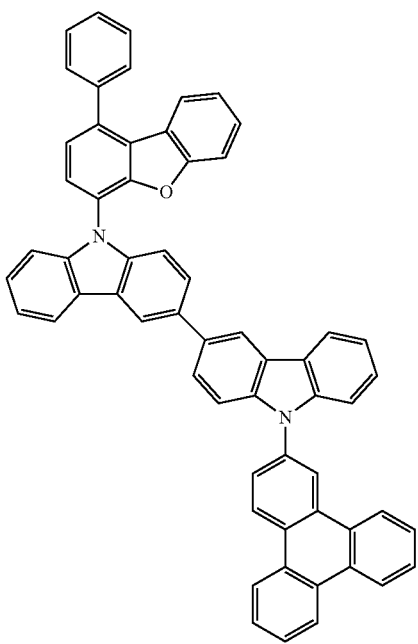
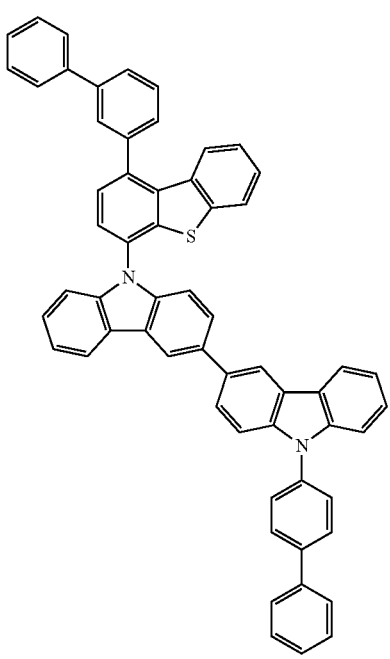
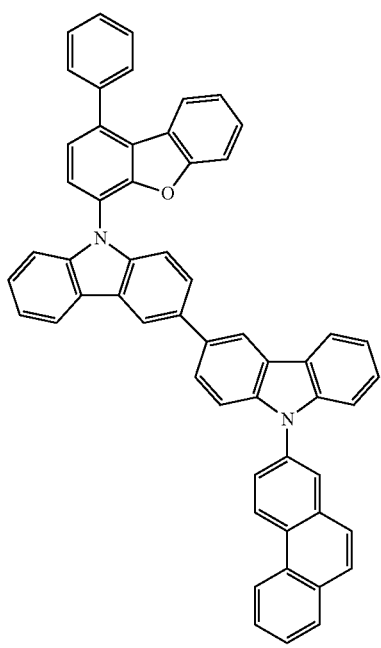

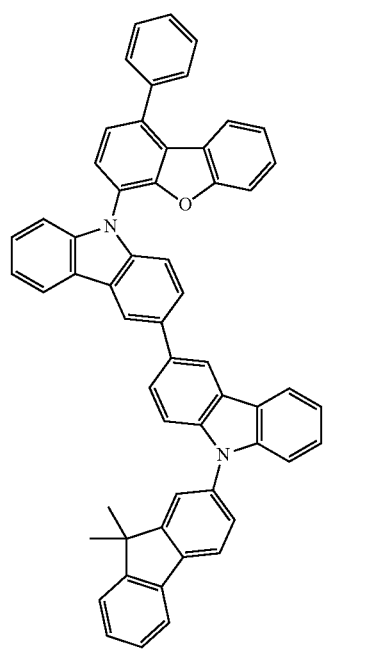
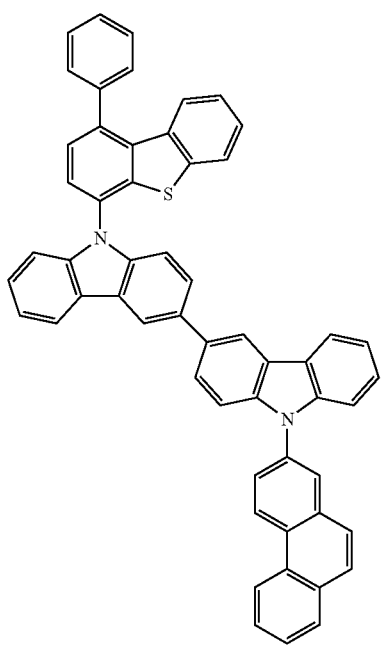
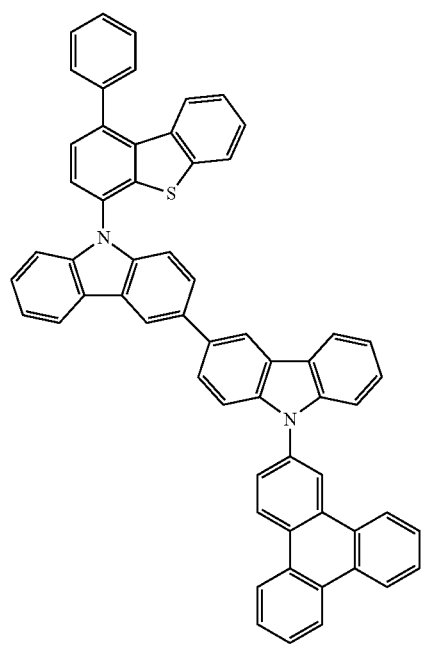

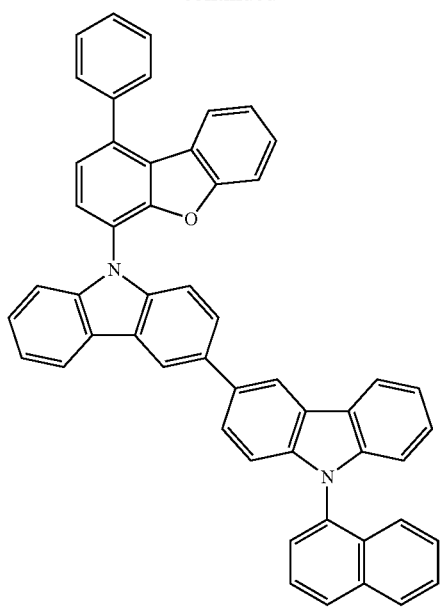
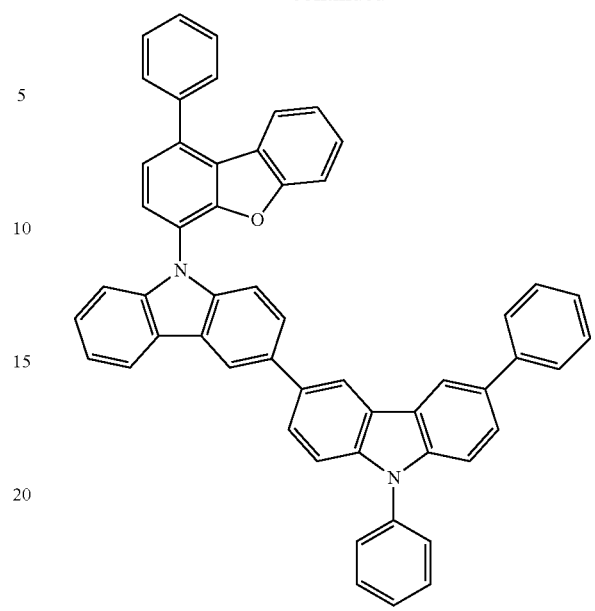
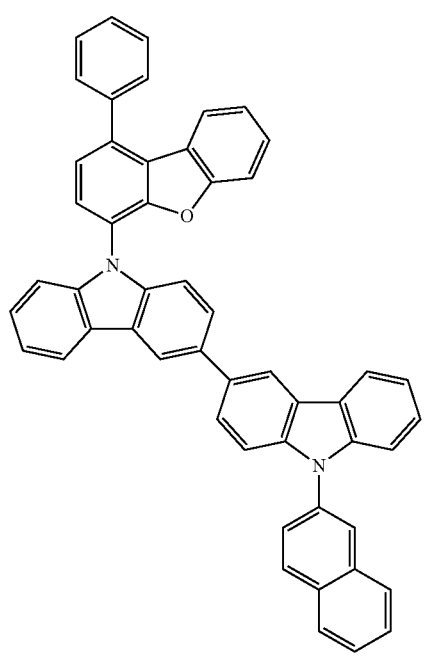
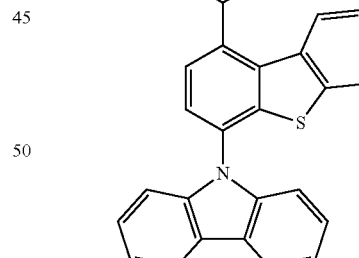

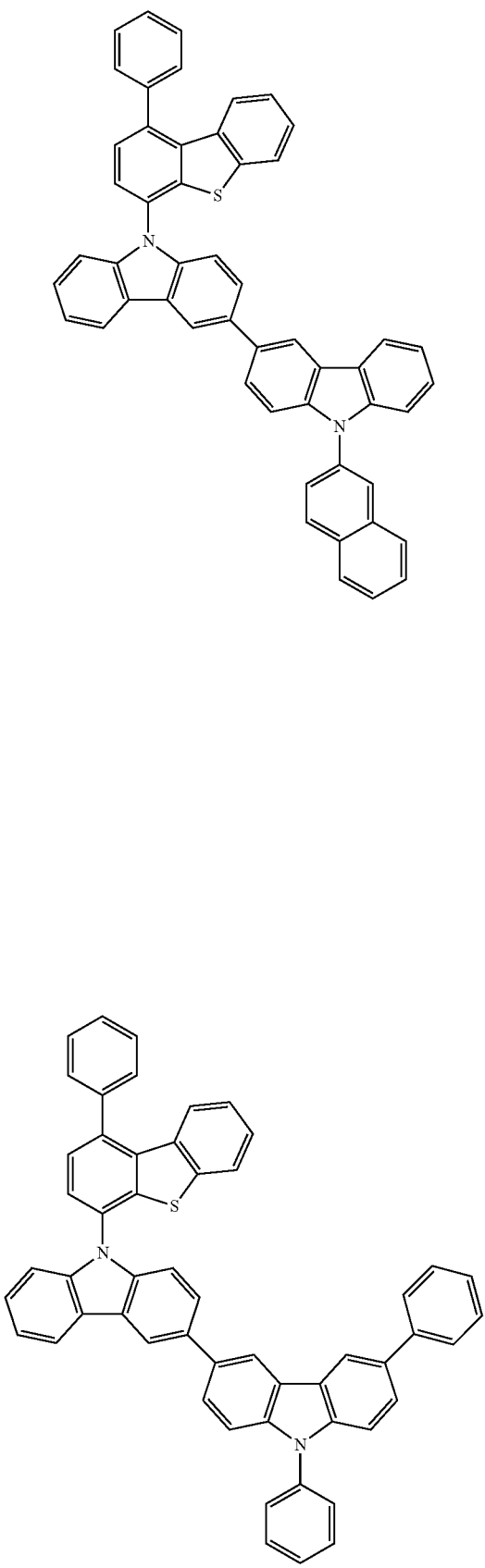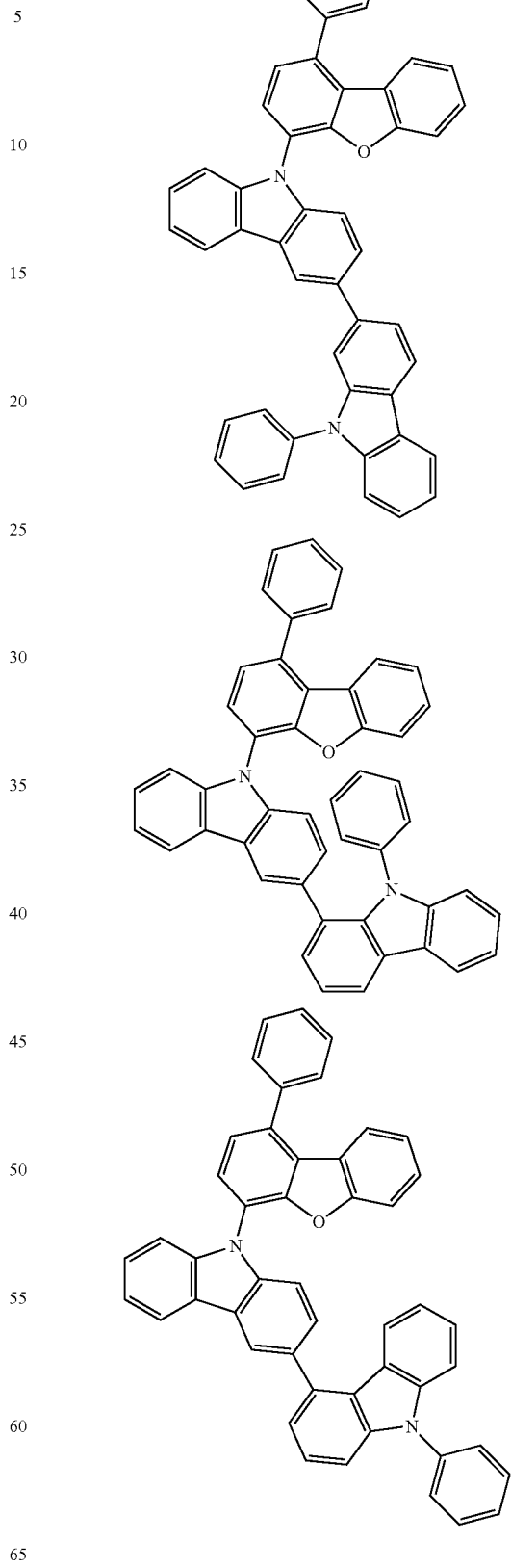

31
-continued
32
-continued
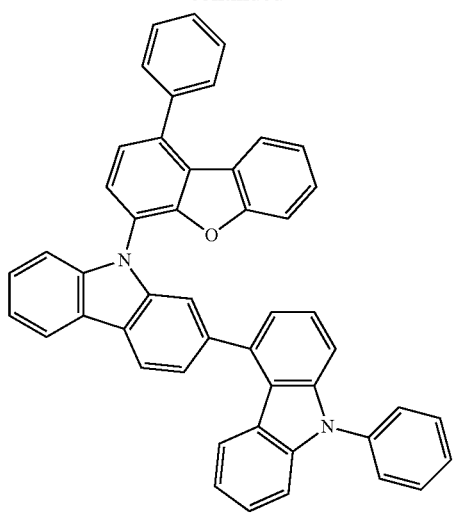
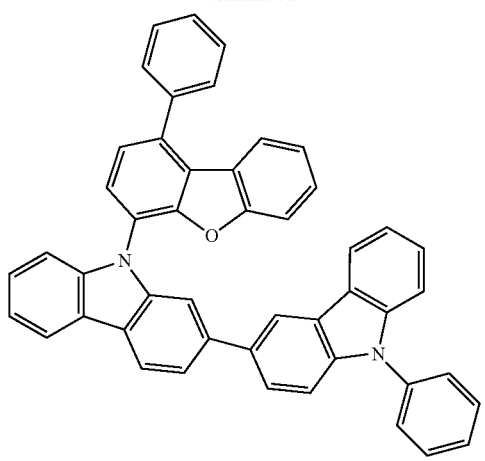

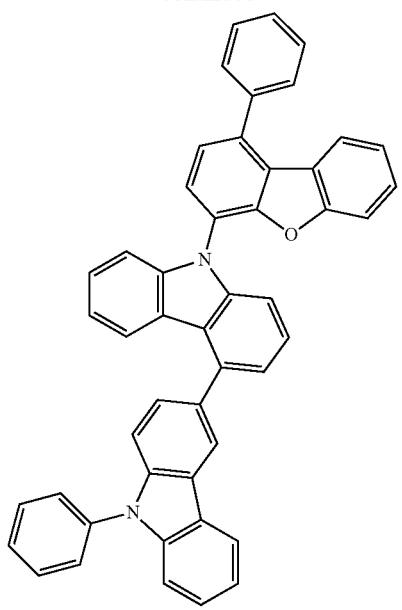
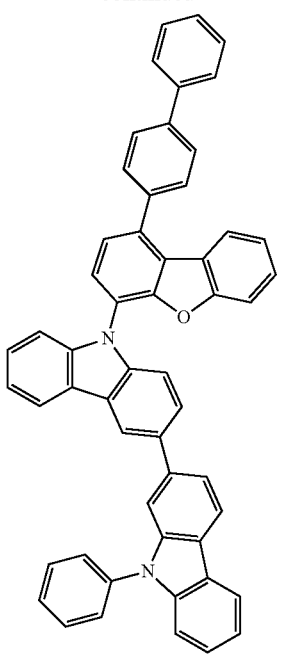
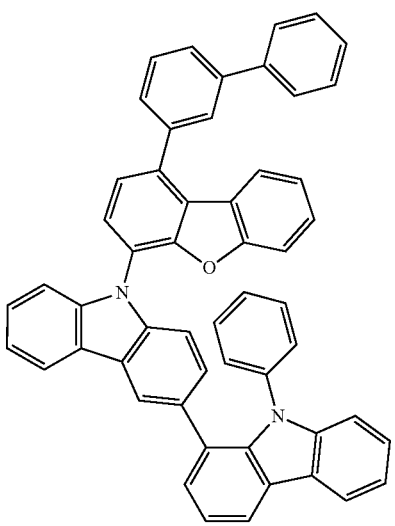

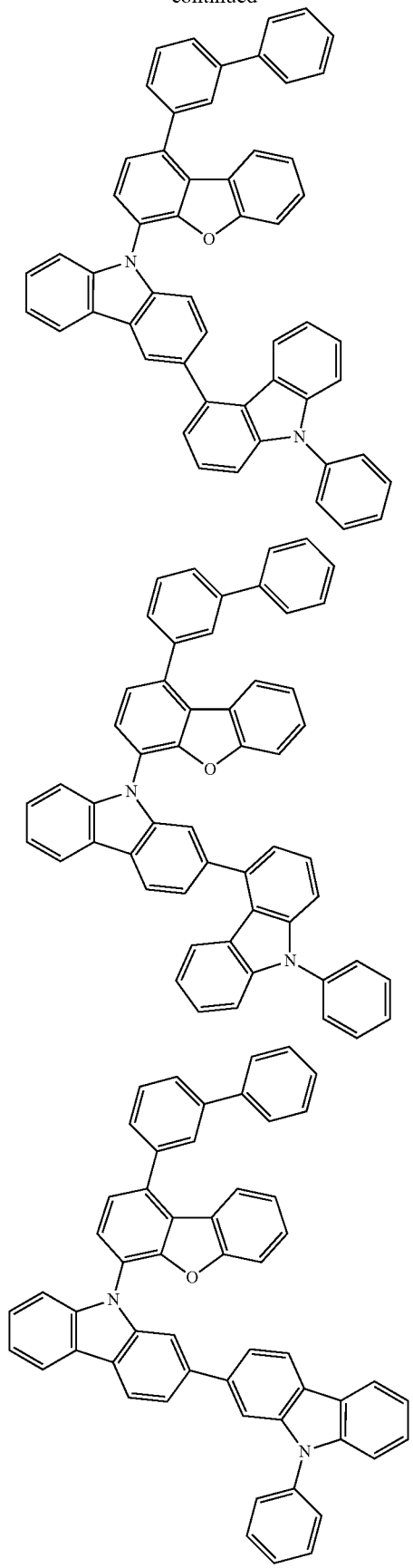
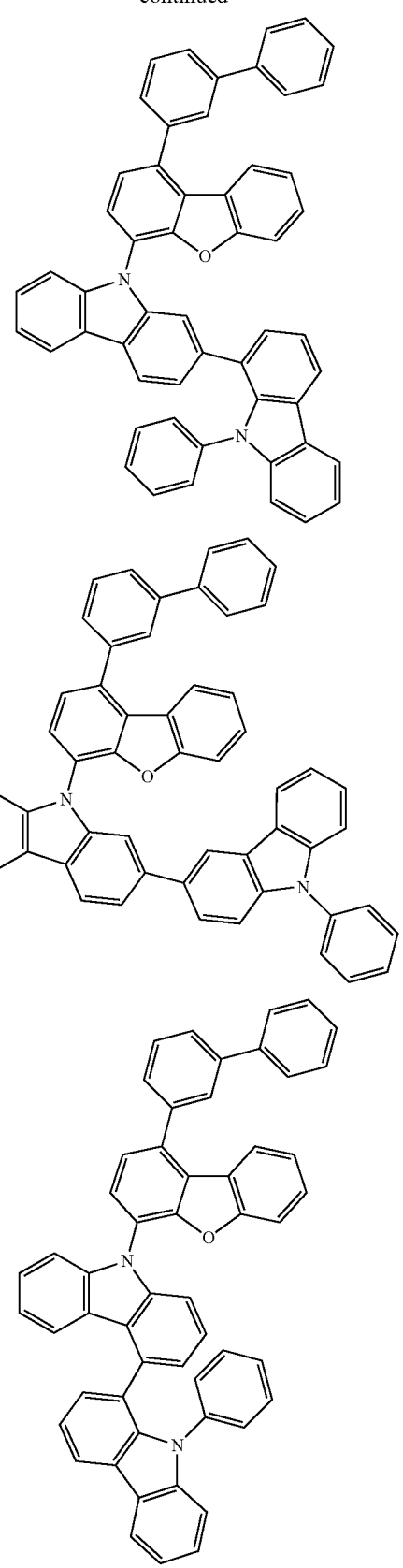

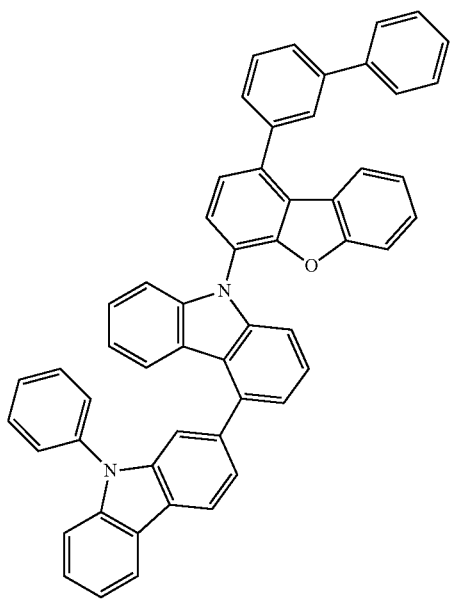
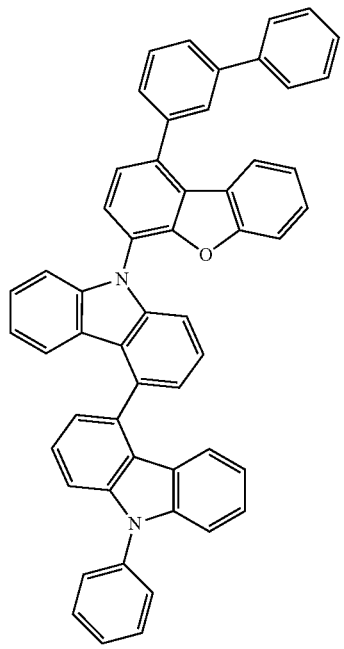
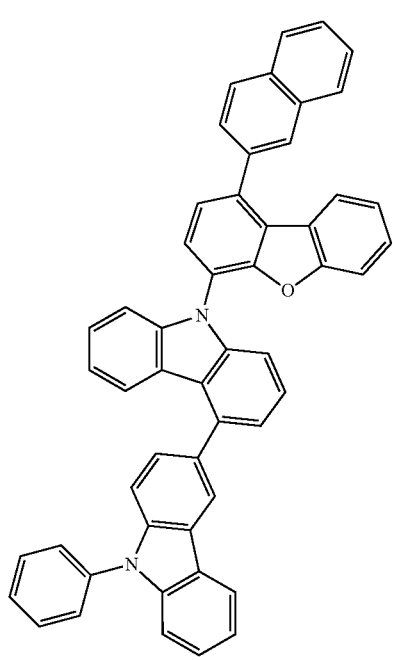
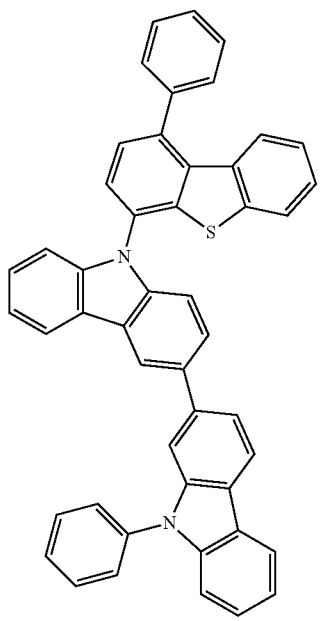

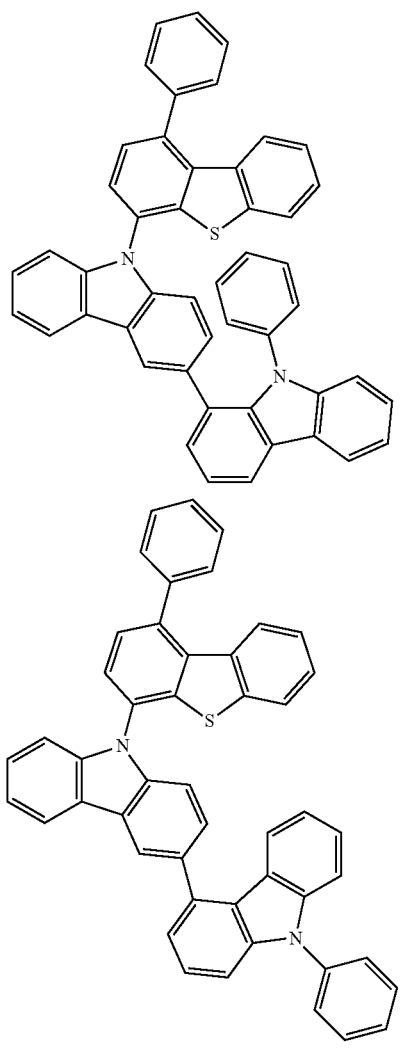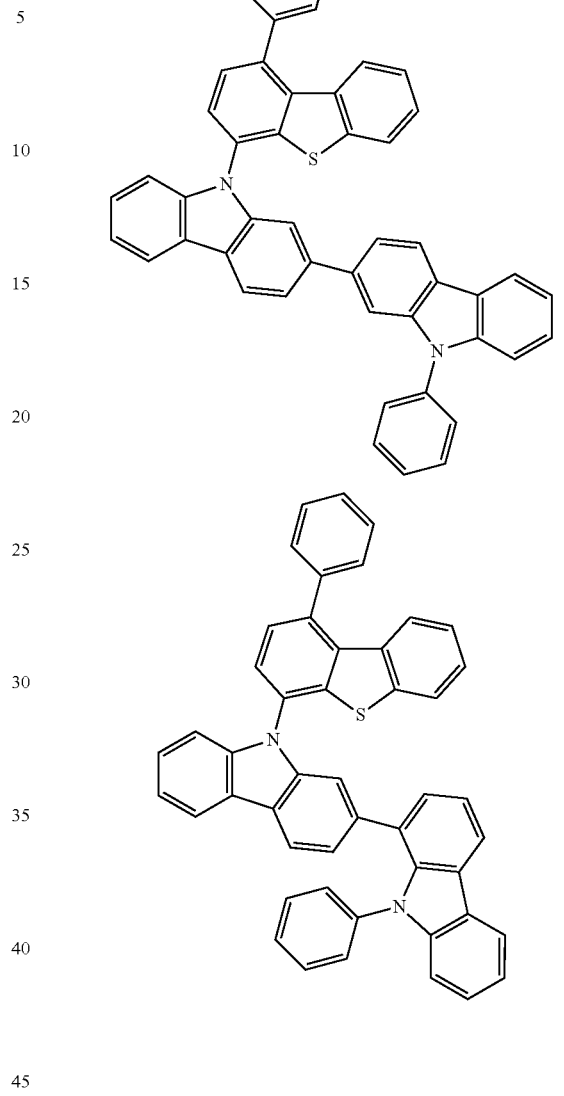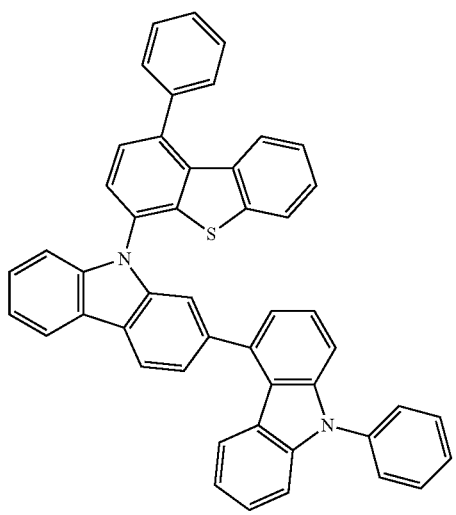

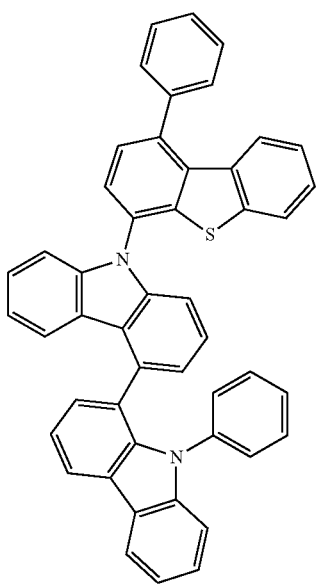
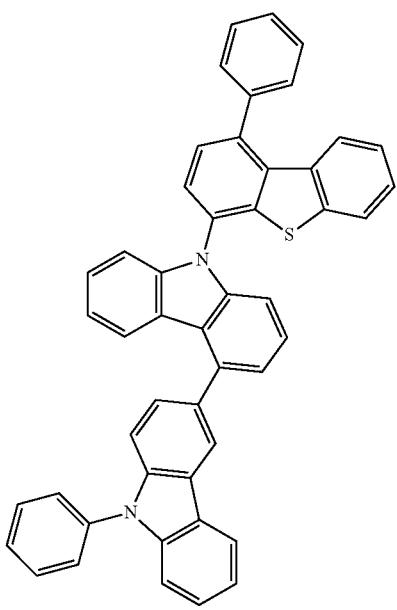
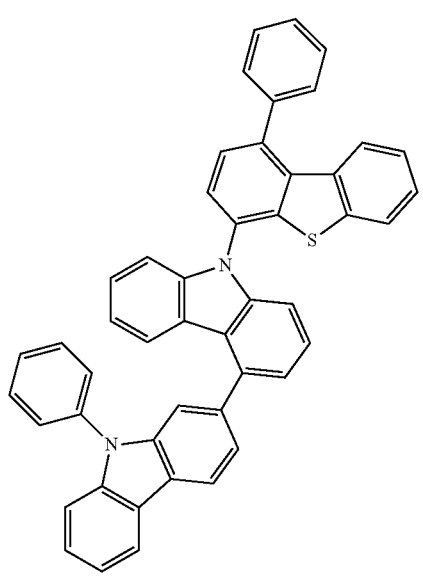
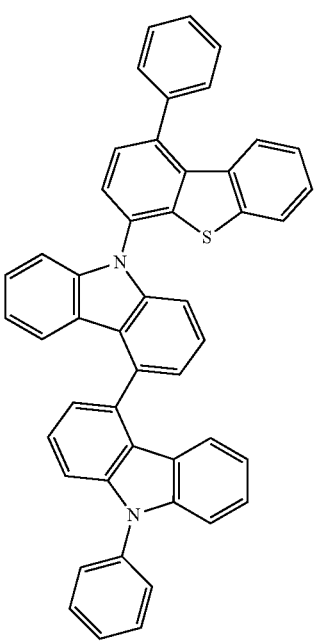

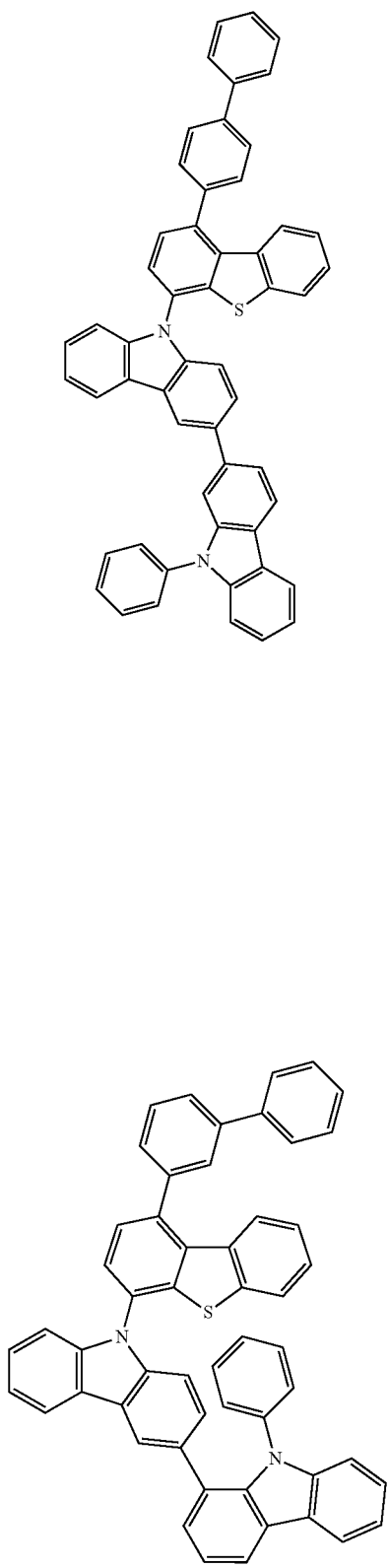
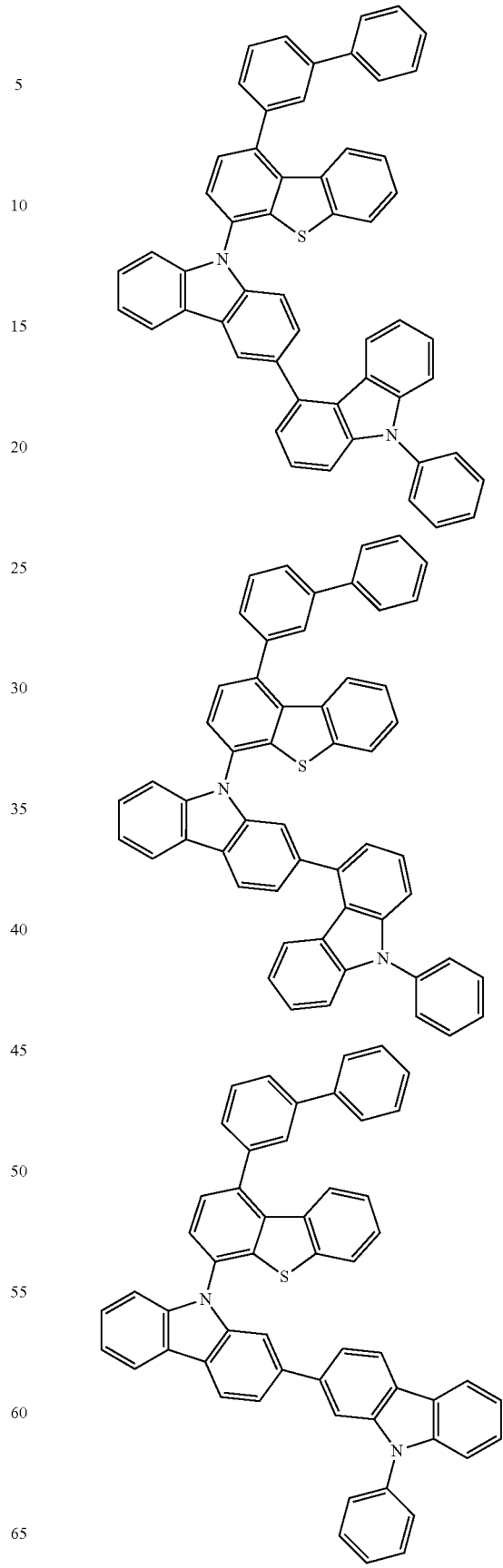

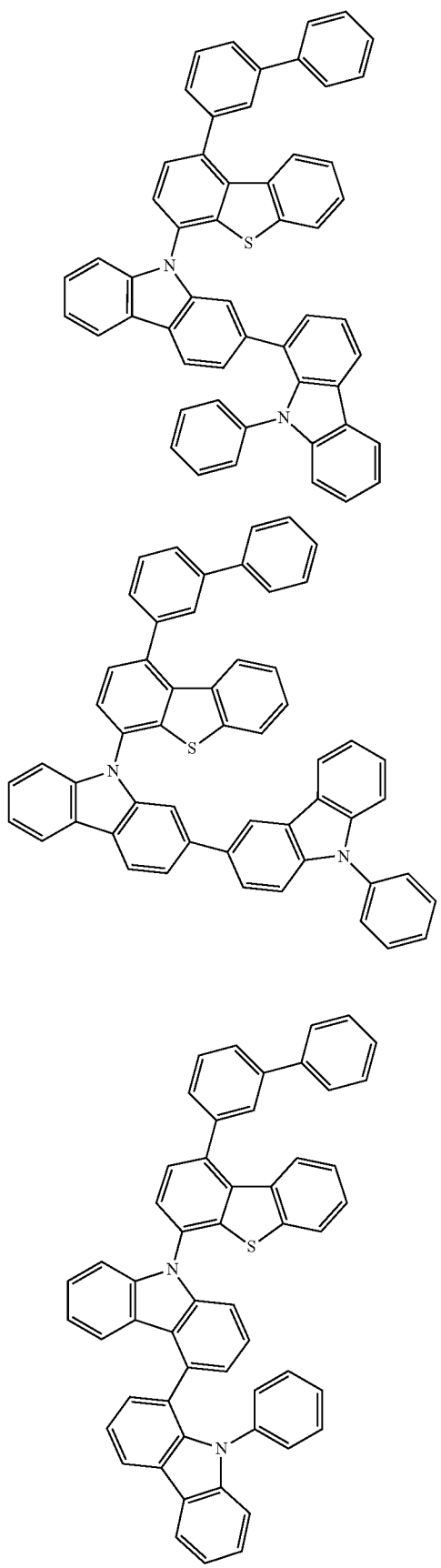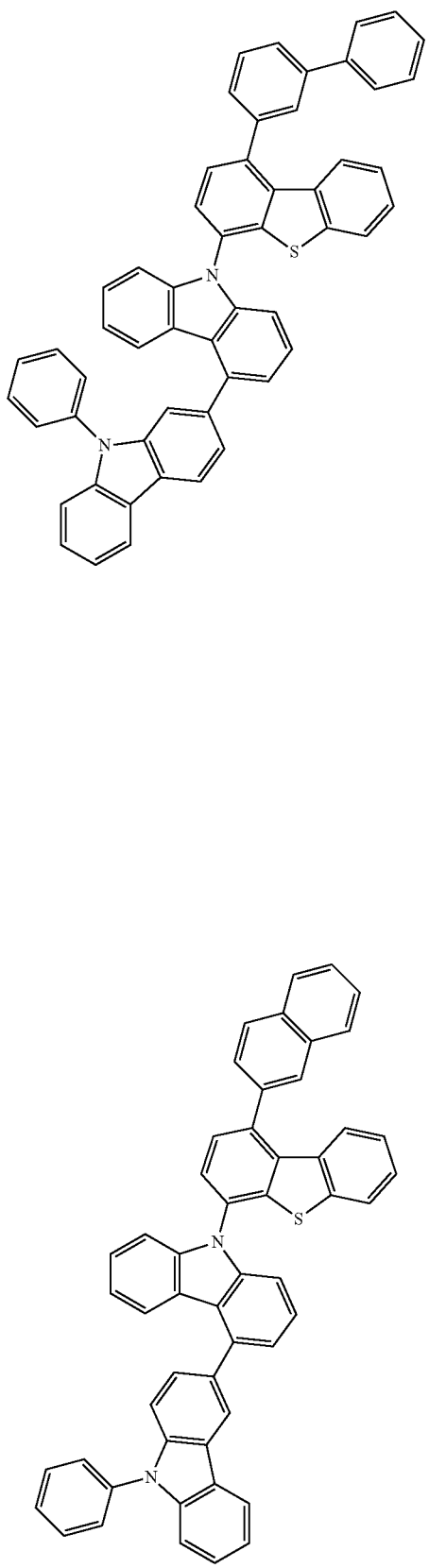

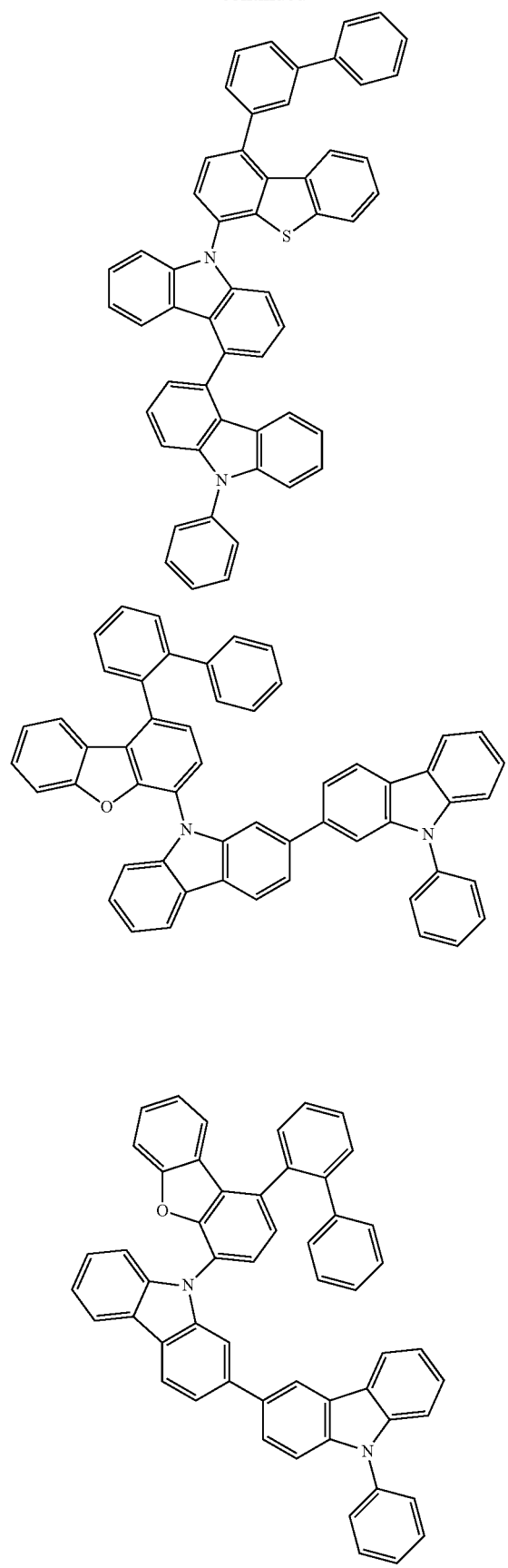
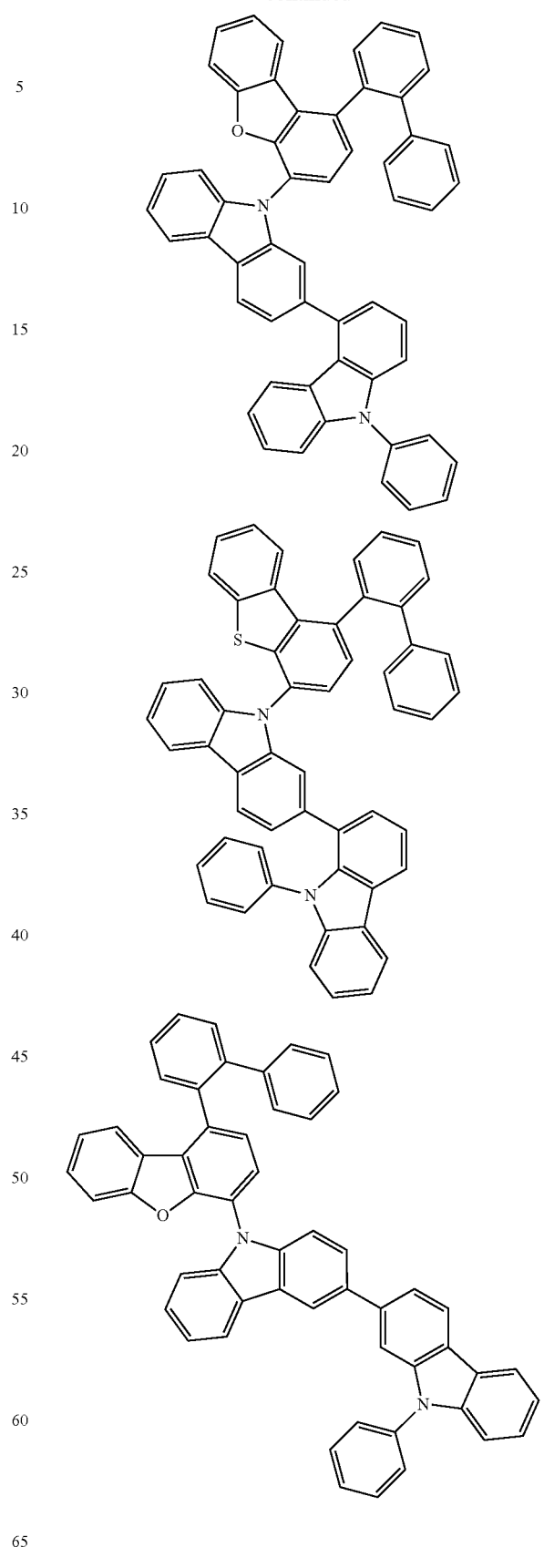

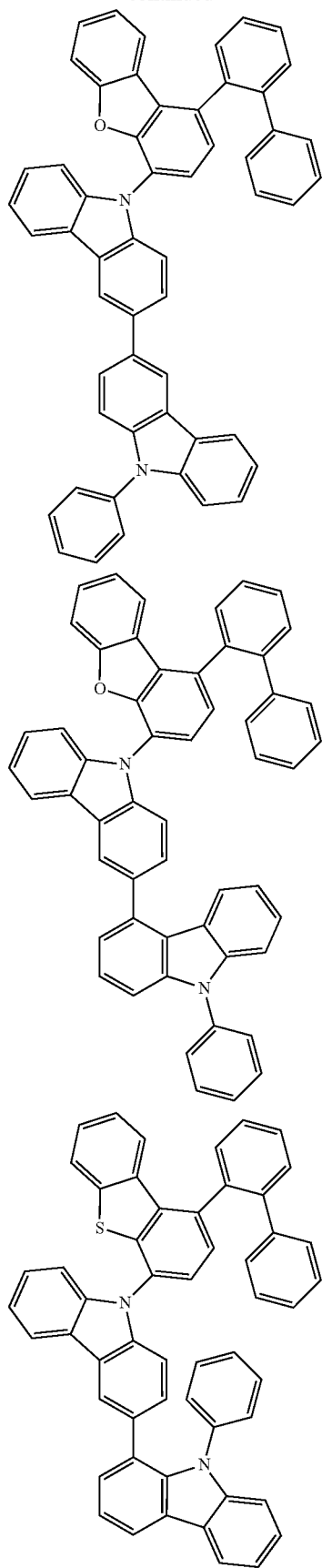
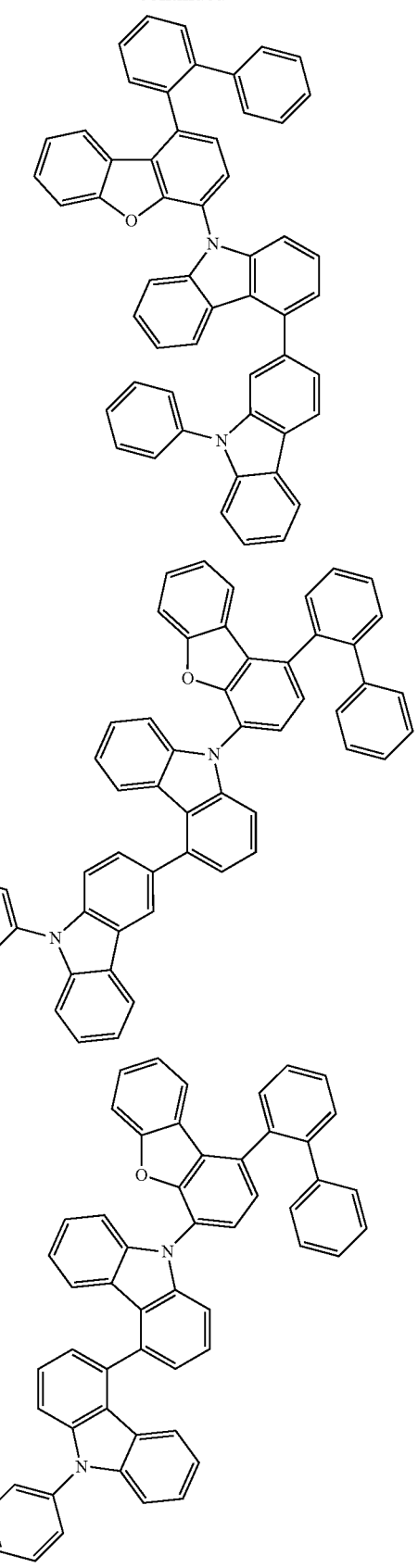

51
-continued
52
-continued
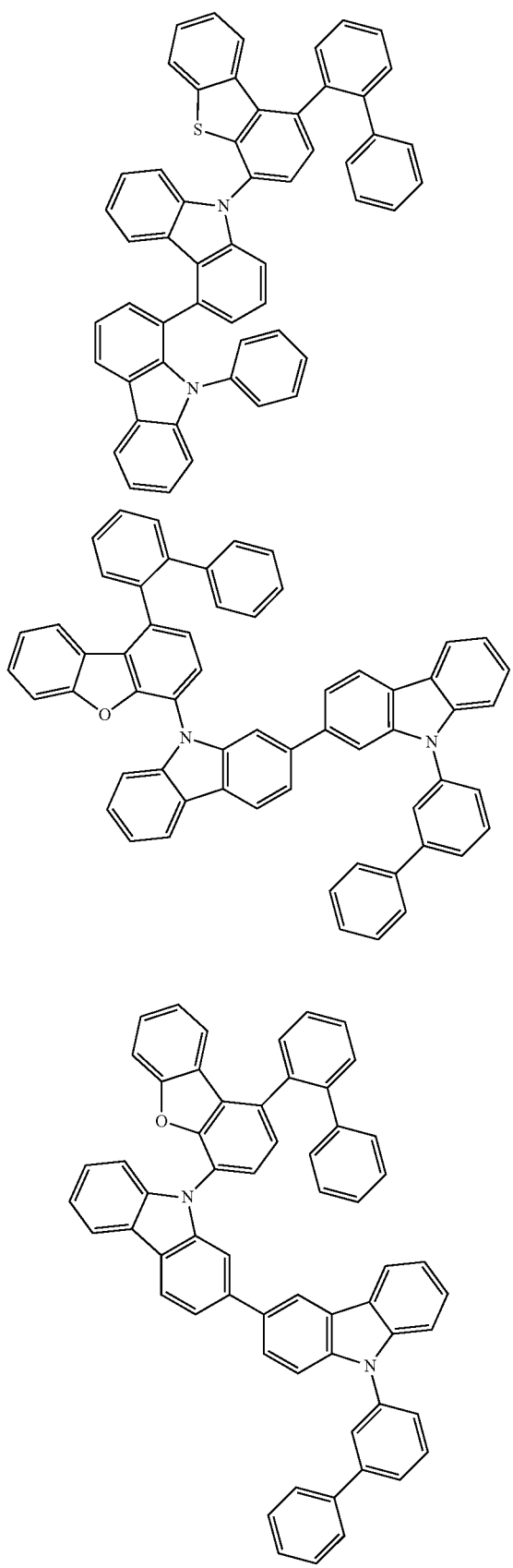
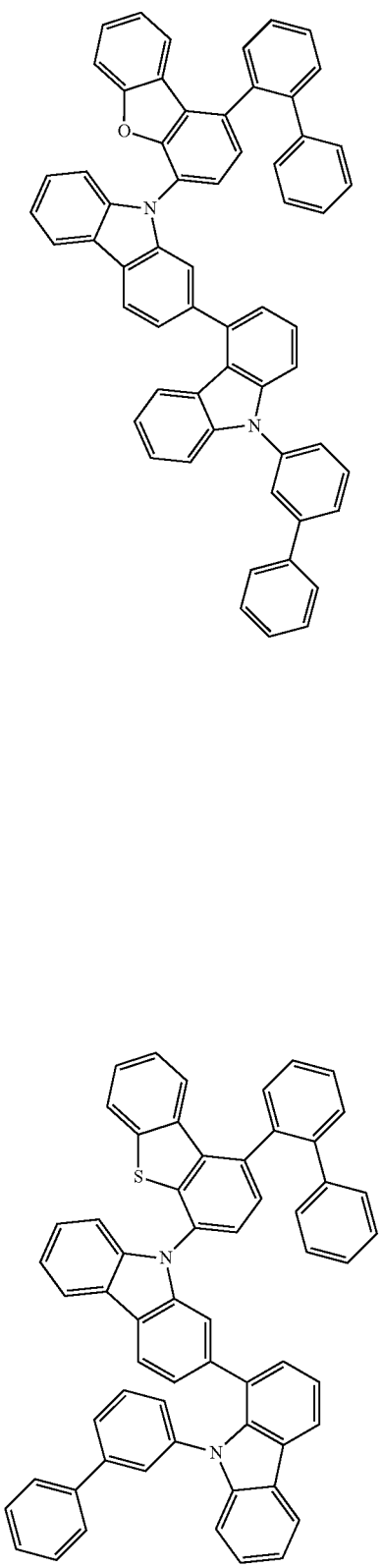

53
-continued
54
-continued
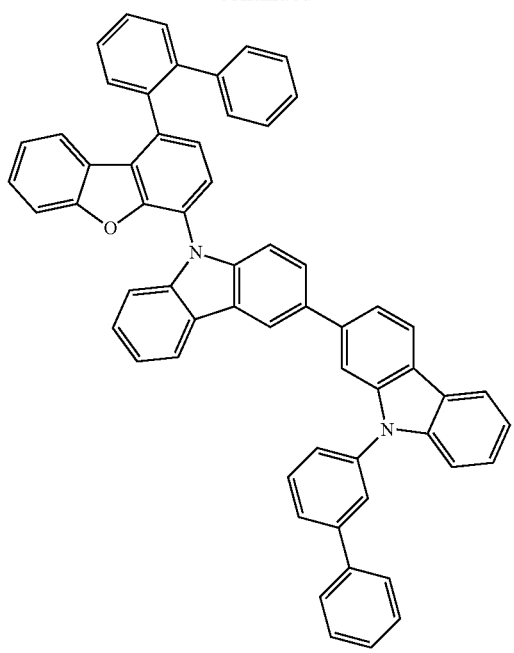
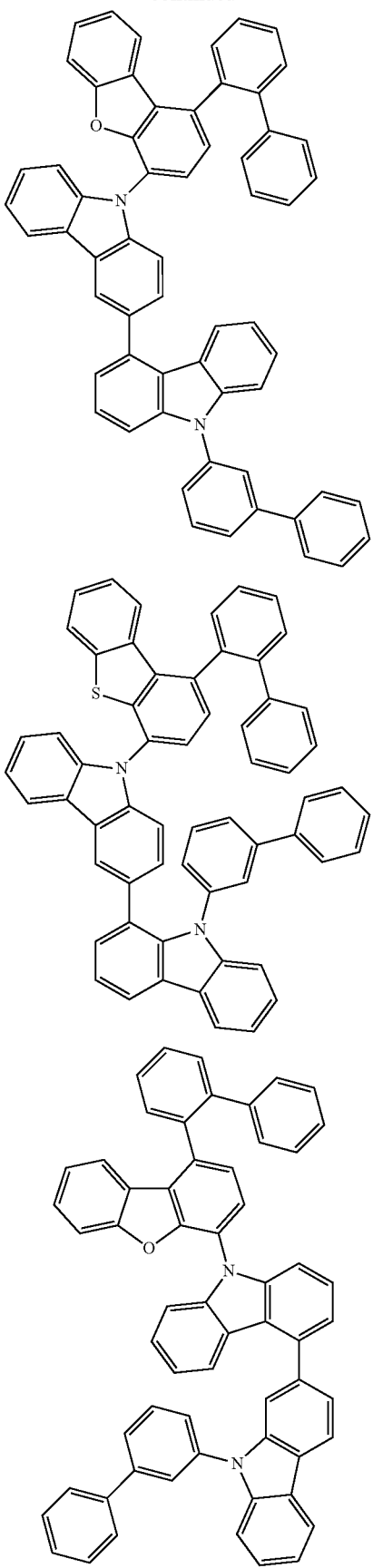

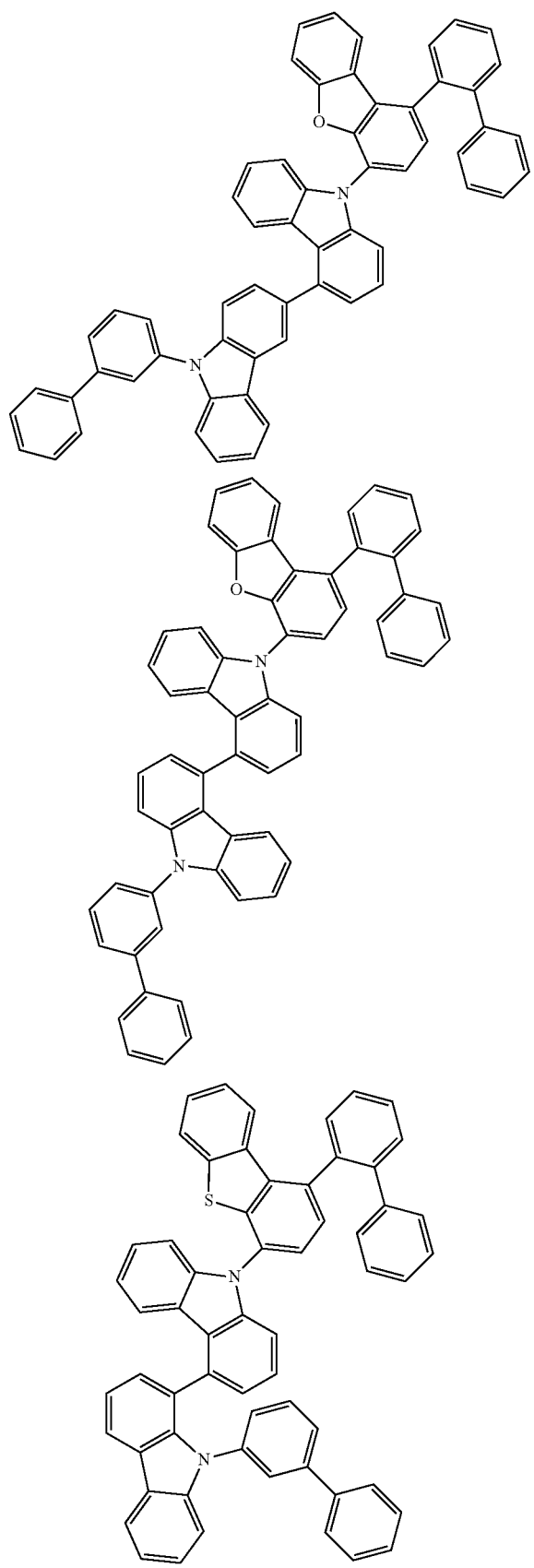
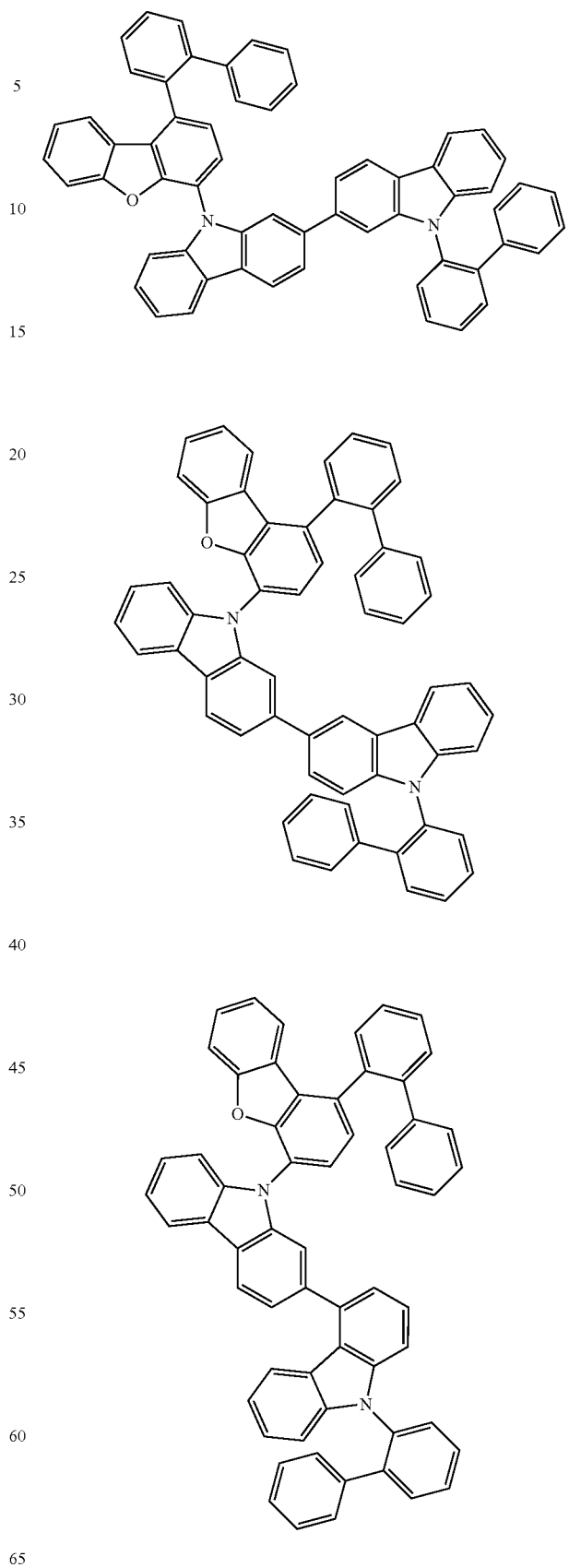

-continued
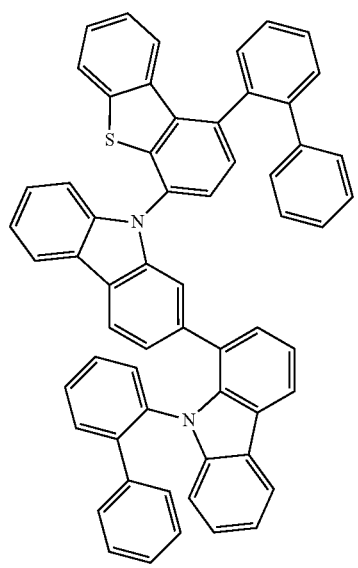
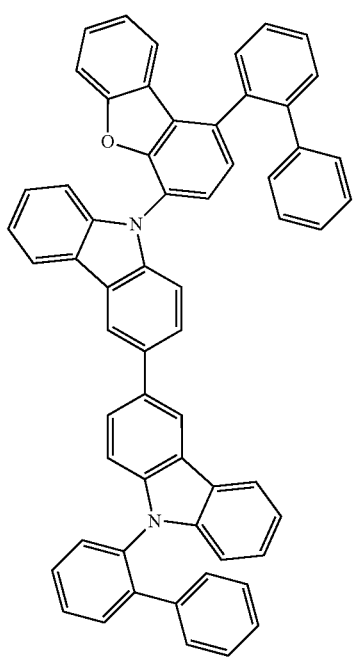
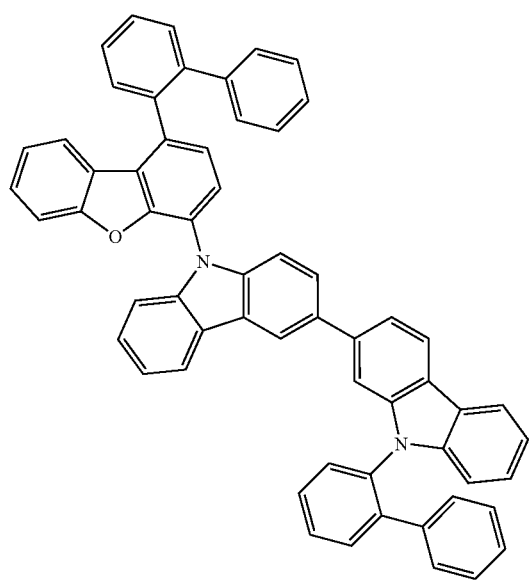
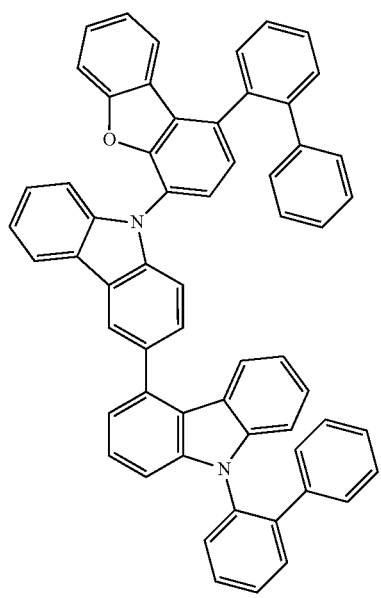

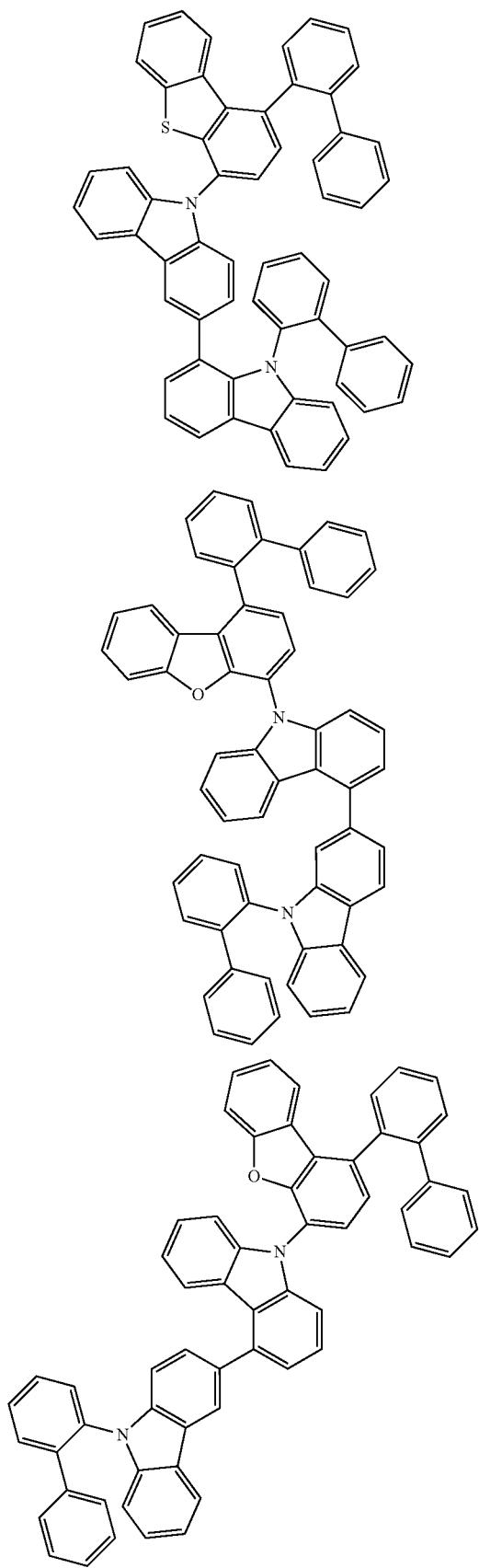

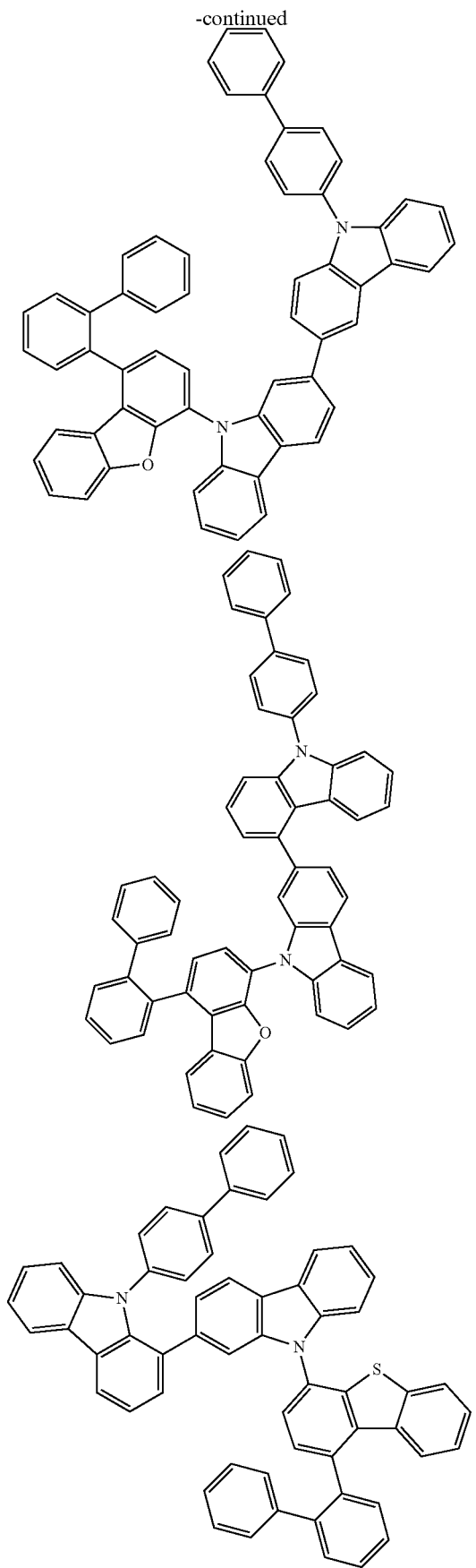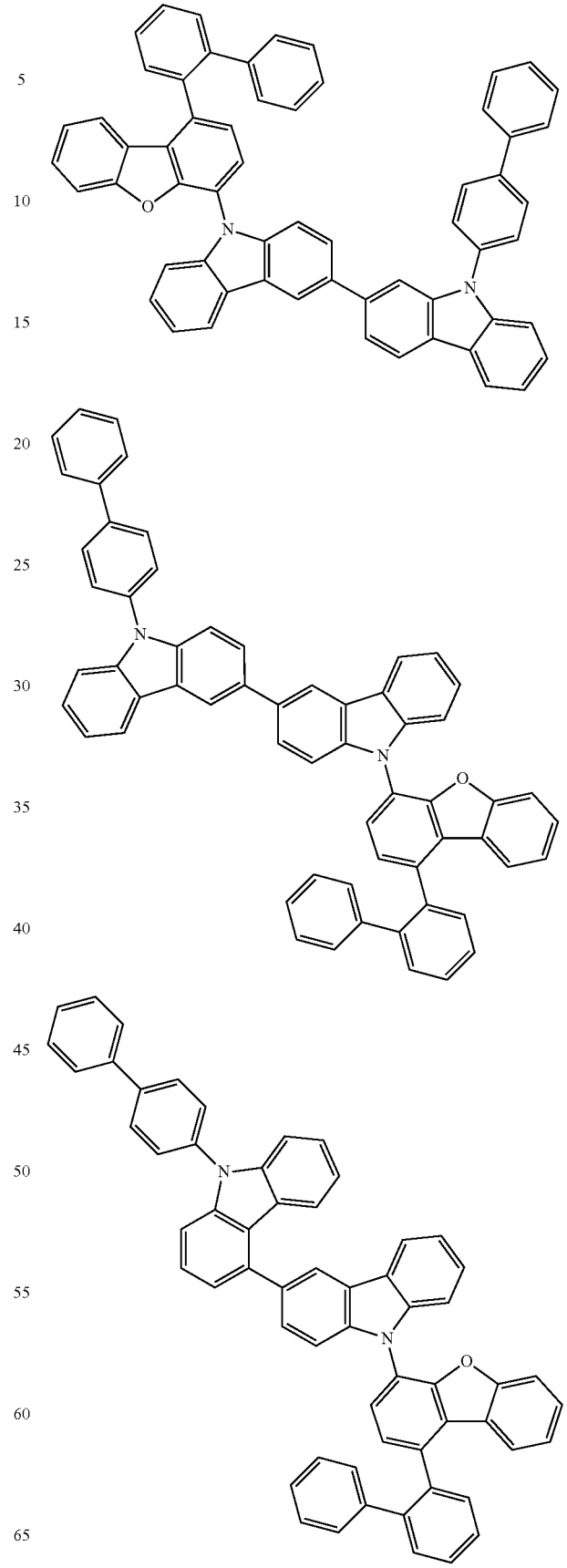

63
-continued
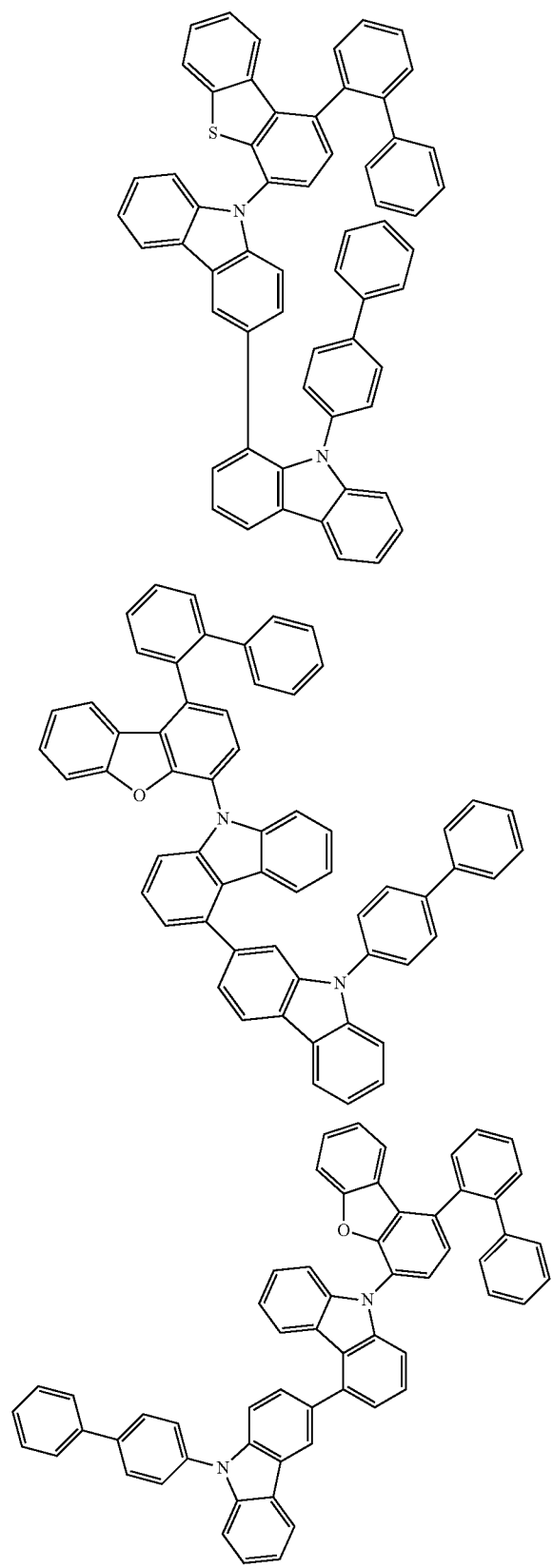
64
-continued
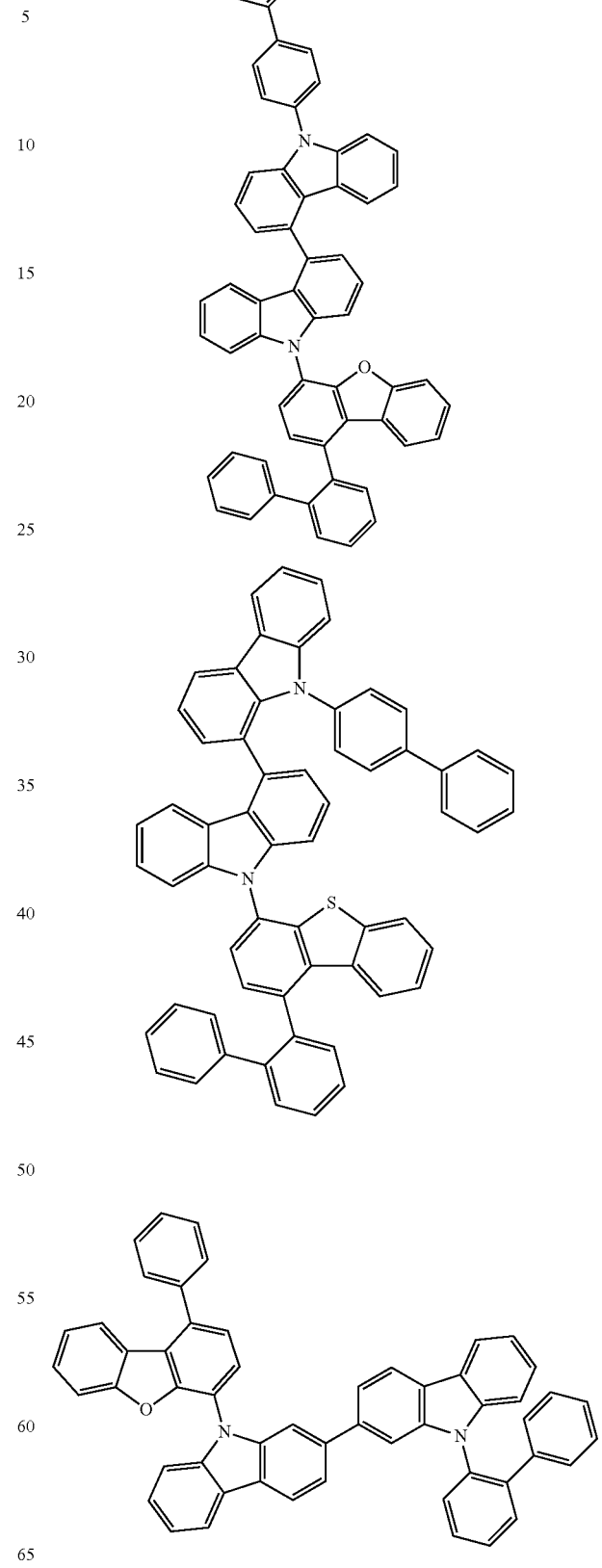

65
-continued
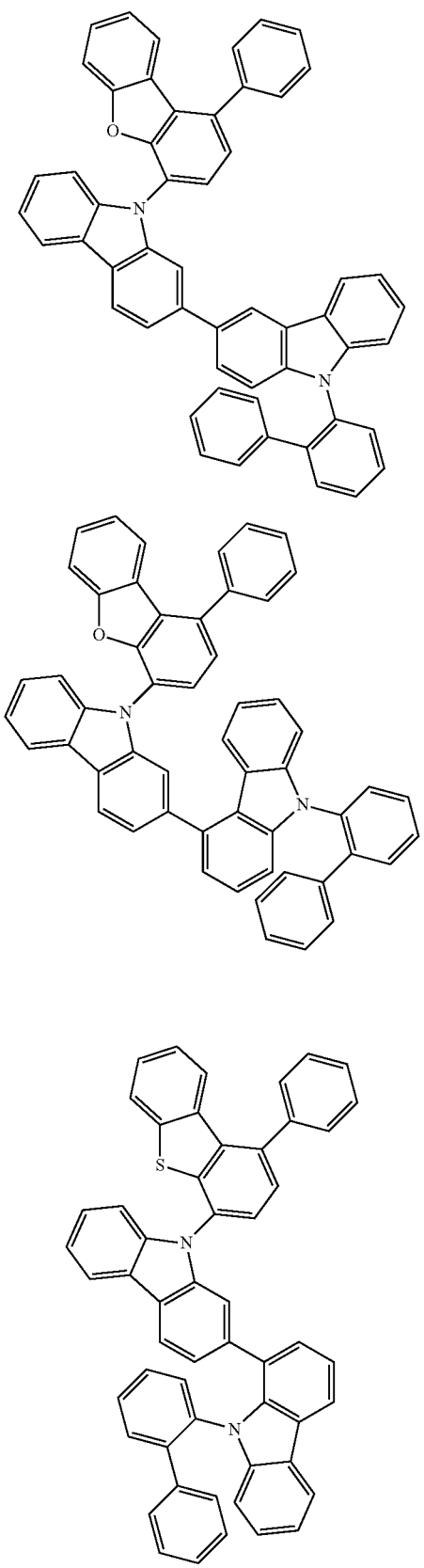
66
-continued
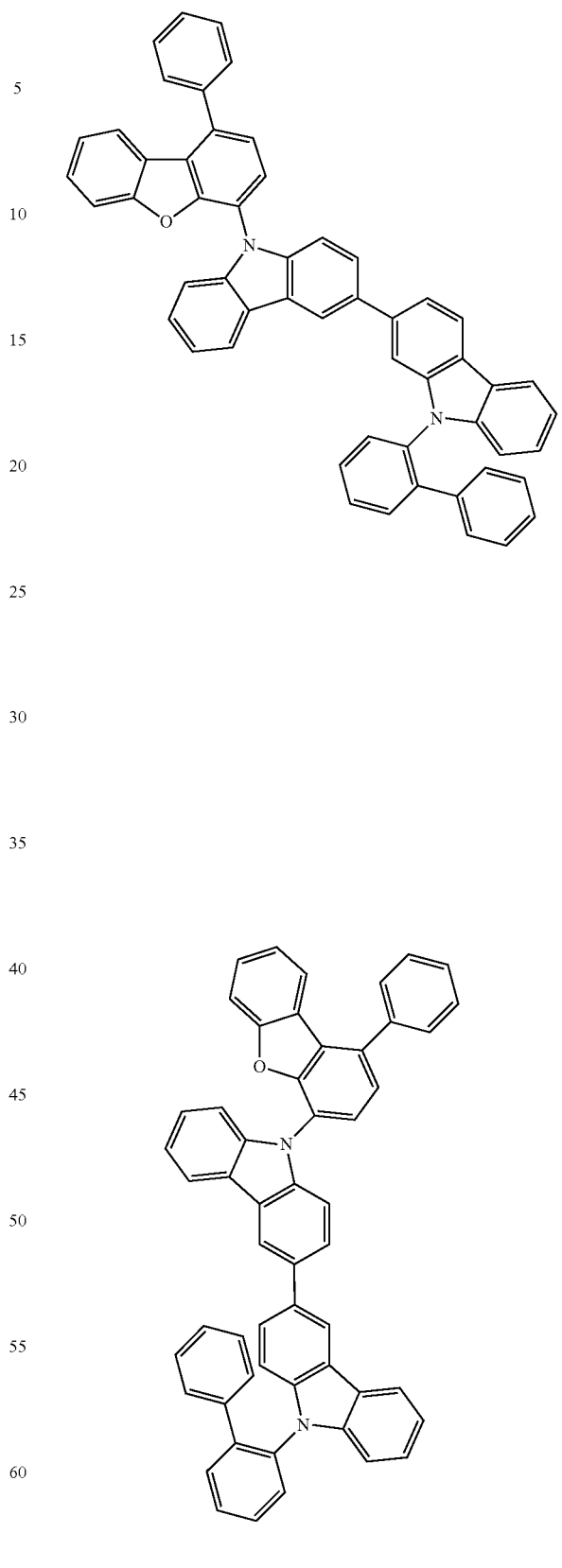

67
-continued
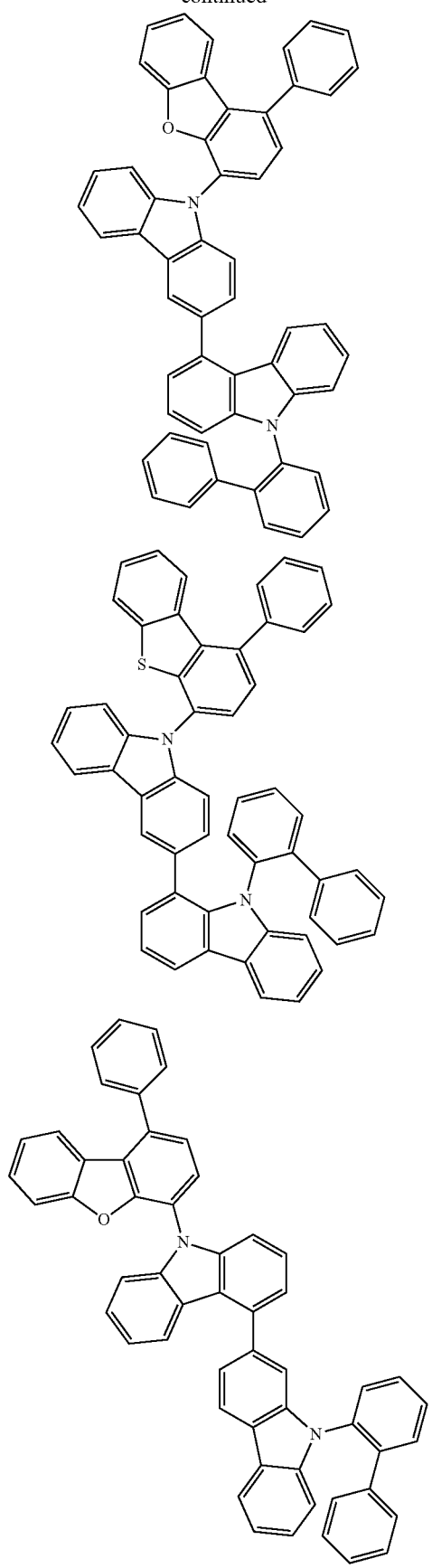
68
-continued
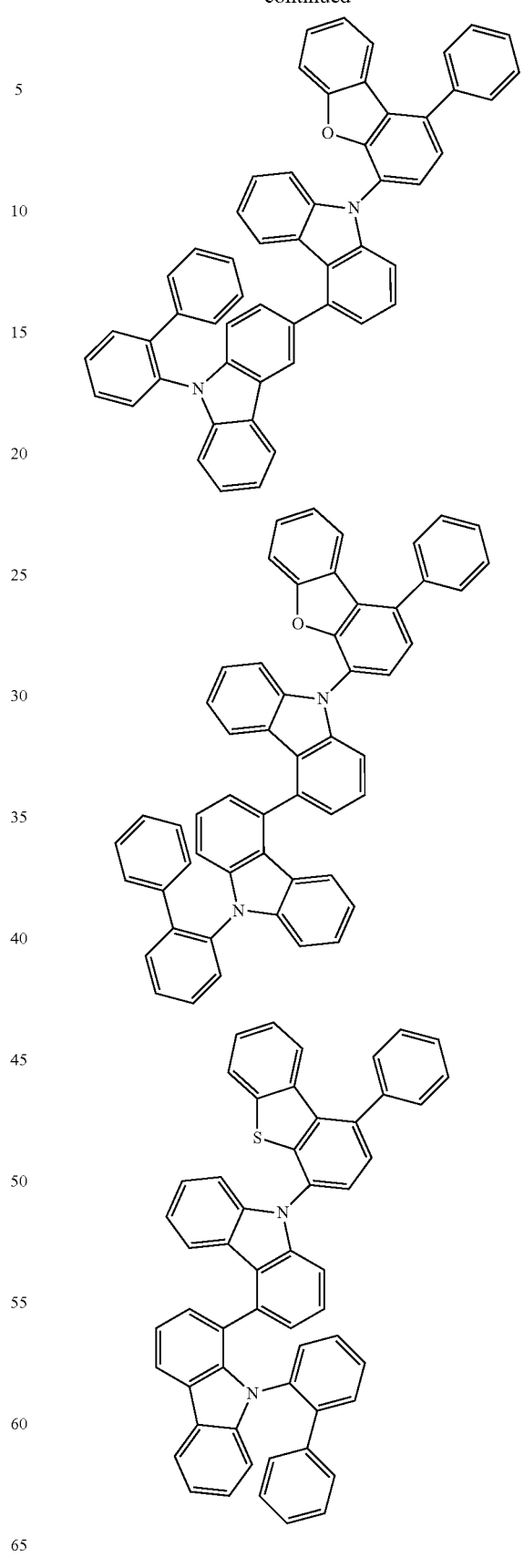

69
-continued
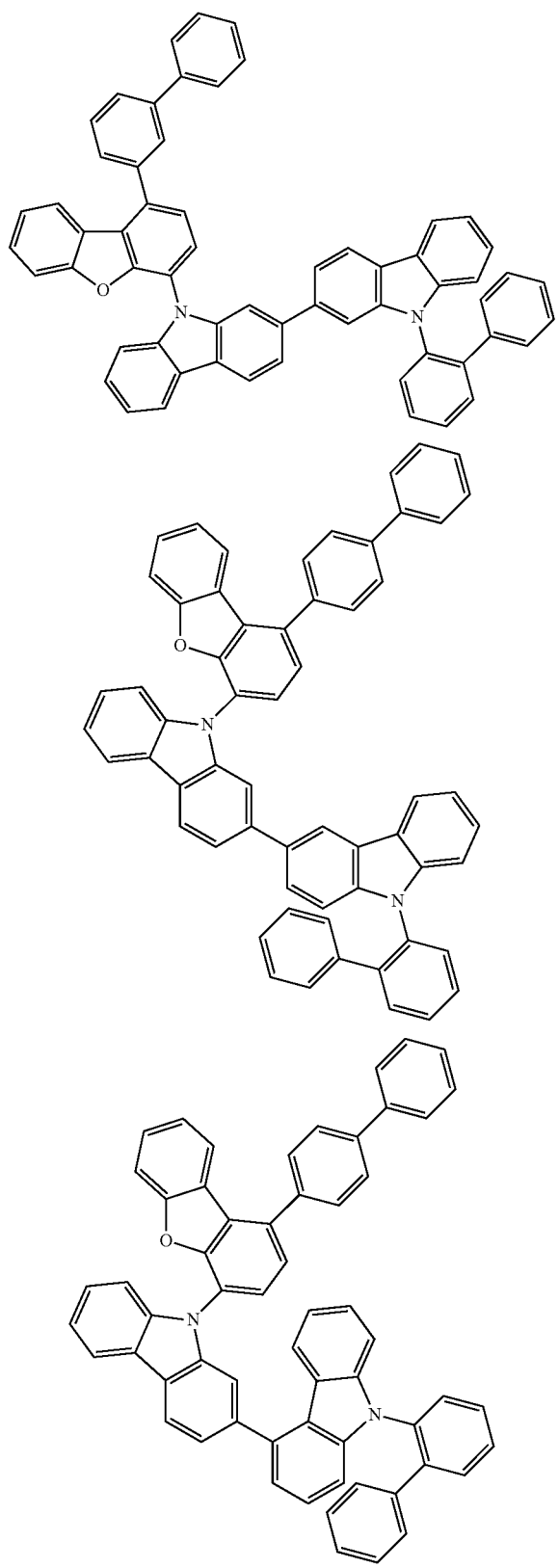
70
-continued
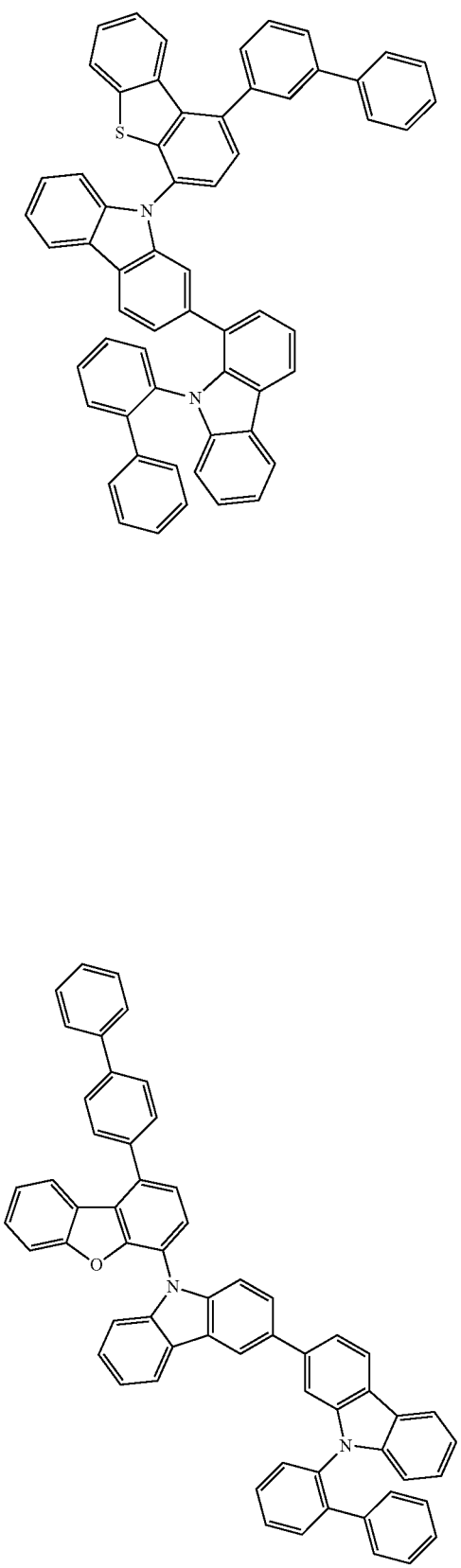

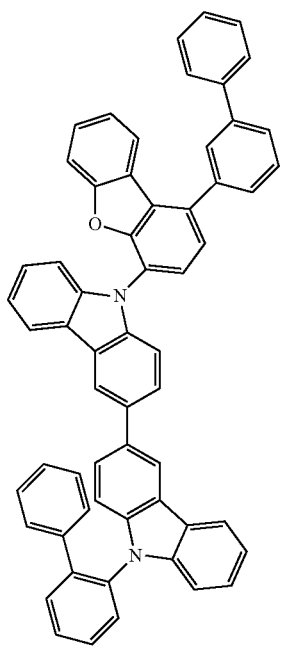
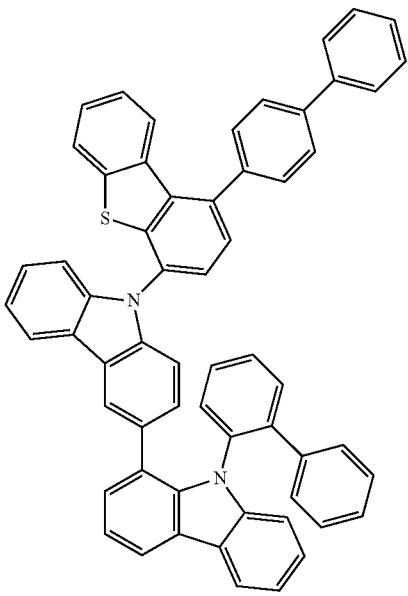
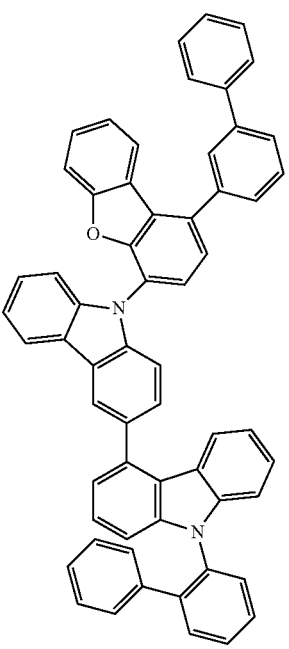
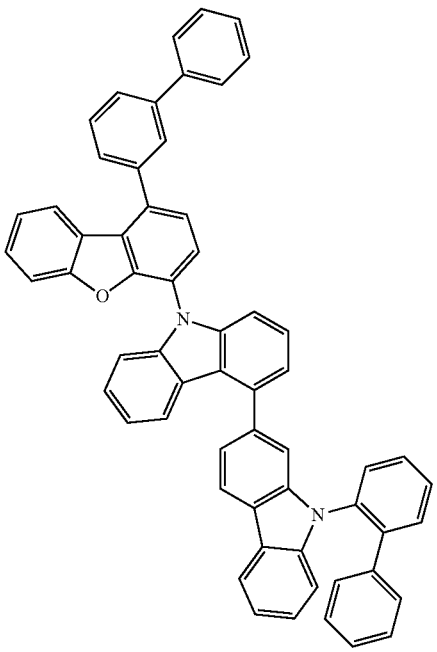

73
-continued
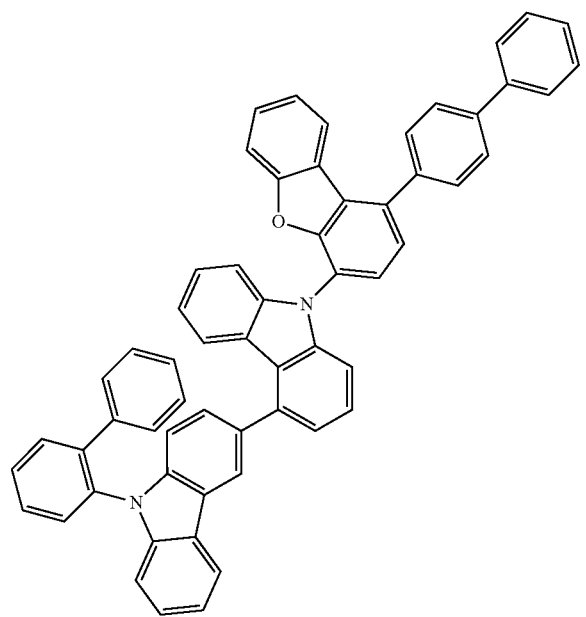
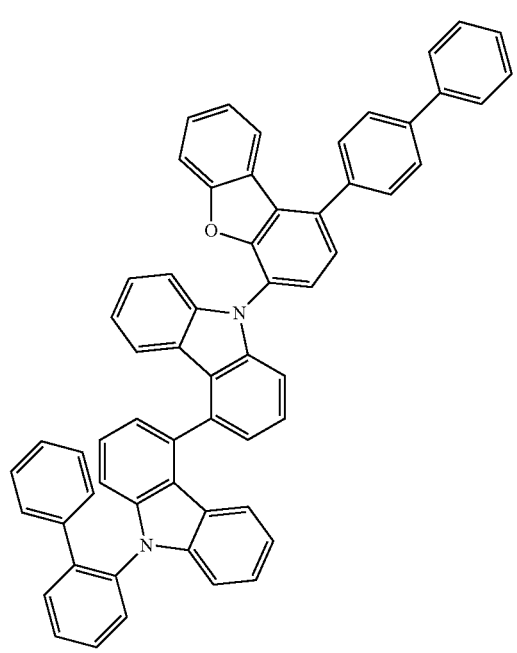
74
-continued
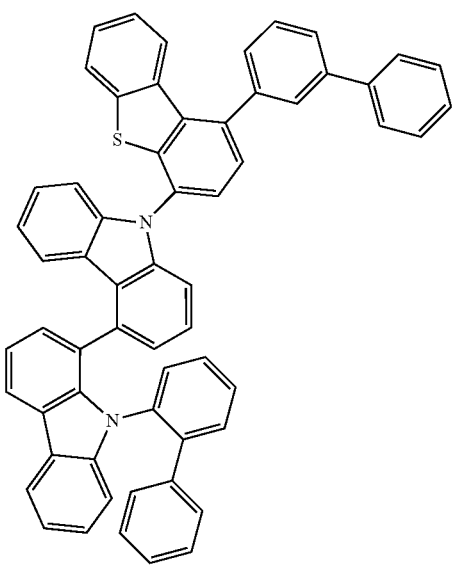
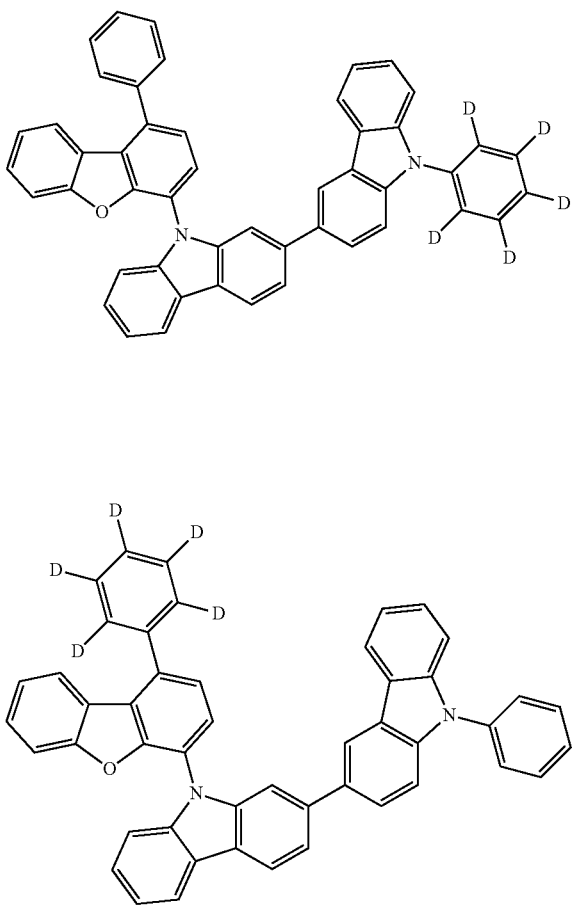

75
-continued
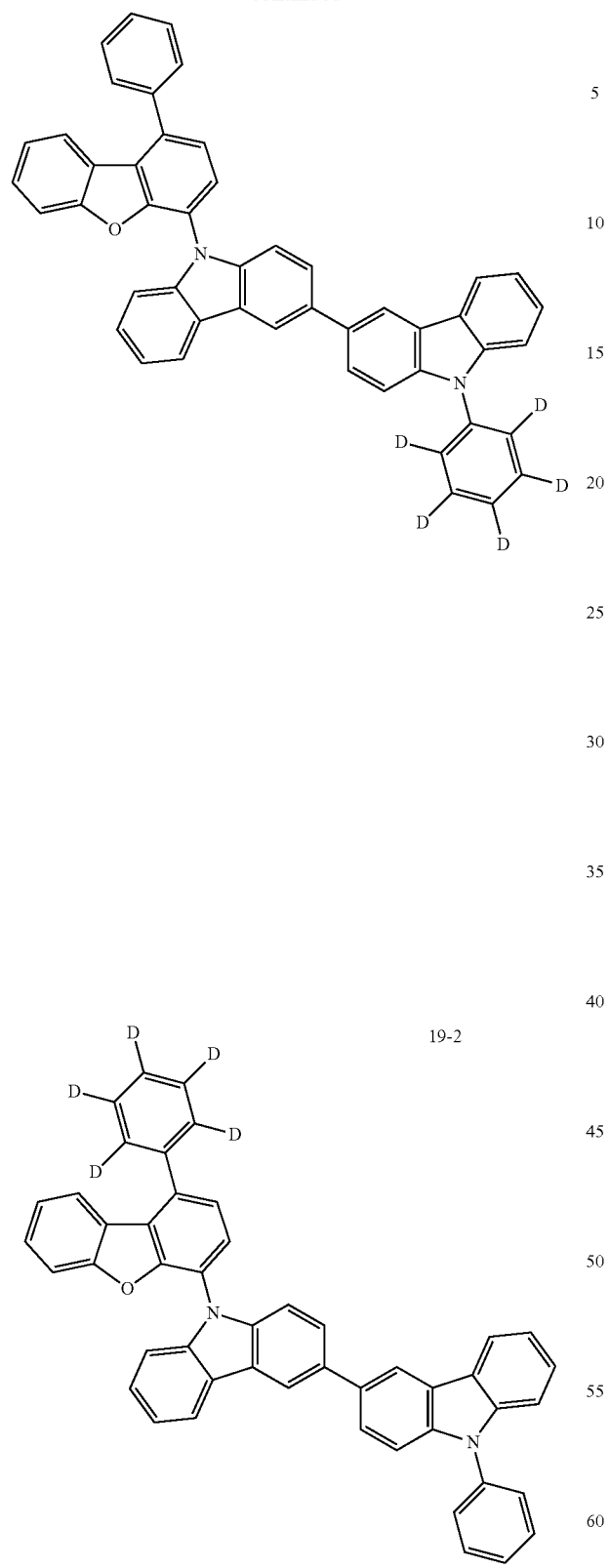
19-2
76
-continued
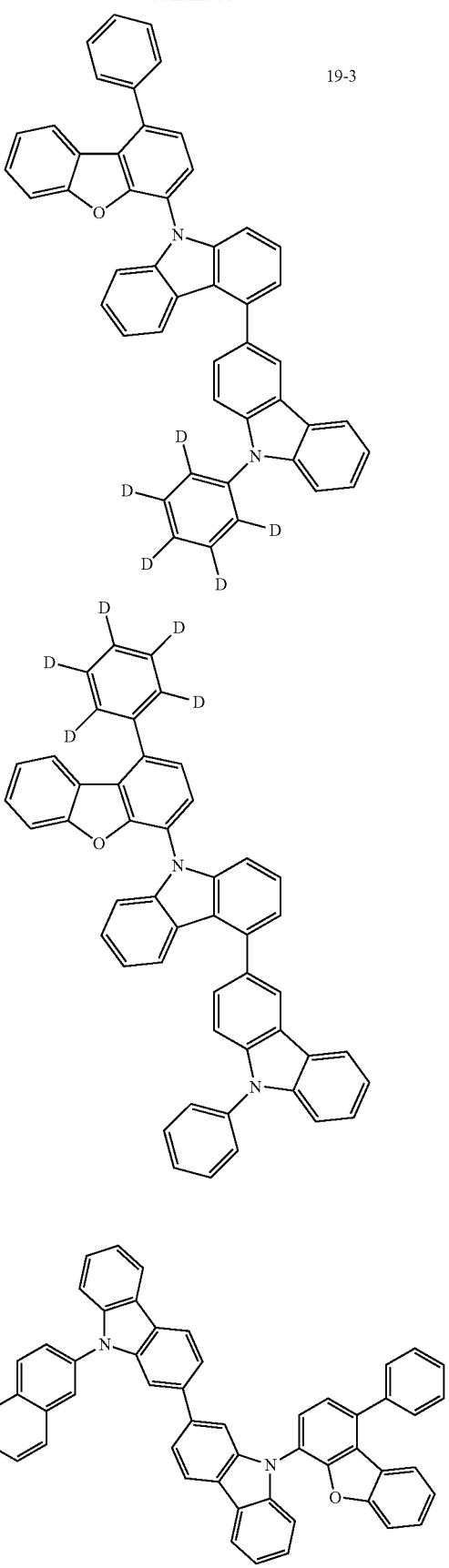
19-3

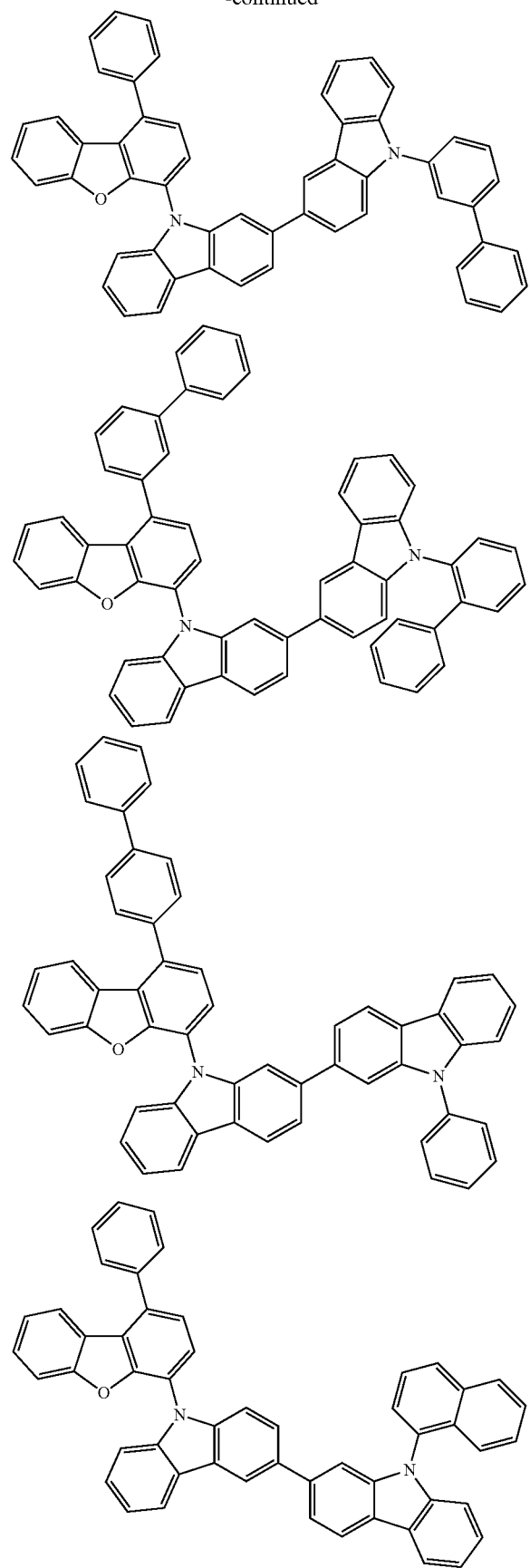
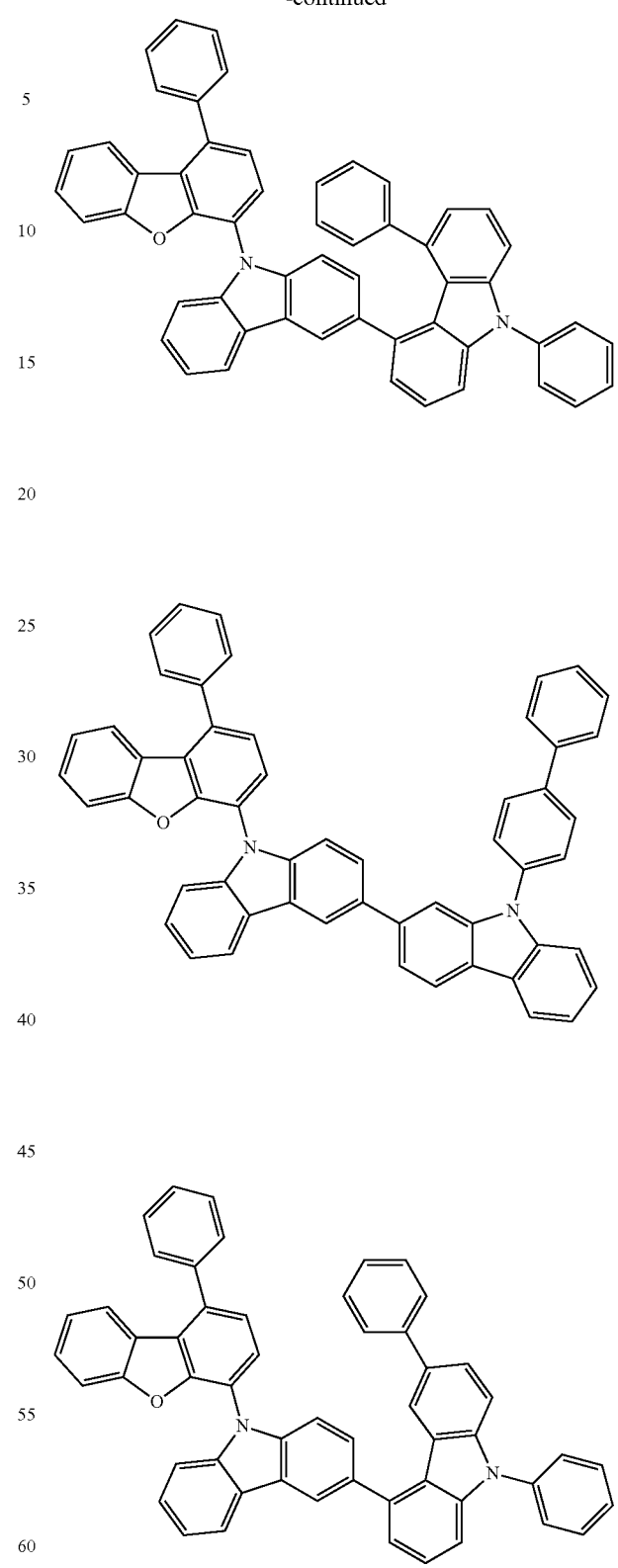

79
-continued
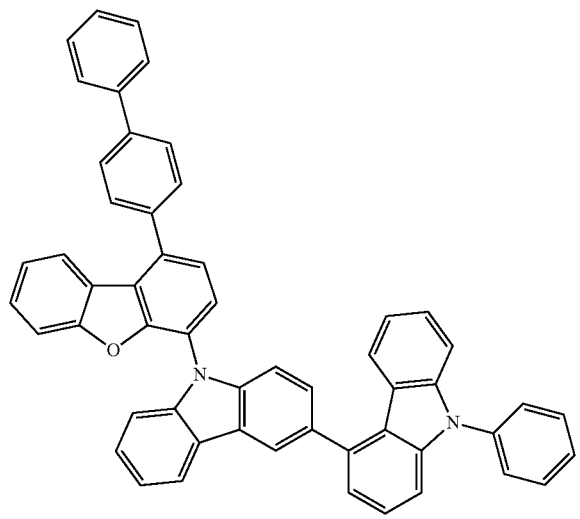
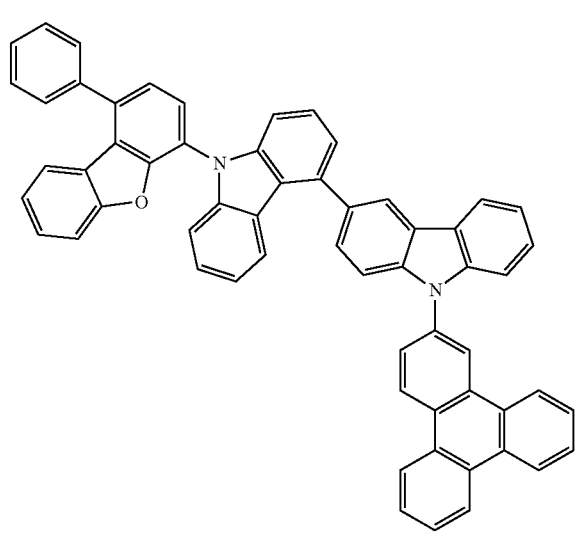 [SMILES: c1ccc(-c2ccc(-n3c4ccccc4c4c(-c5ccc6c(c5)c5ccccc5n6-c5ccc6c7ccccc7c7ccccc7c6c5)cccc43)c3oc4ccccc4c23)cc1]
80
-continued
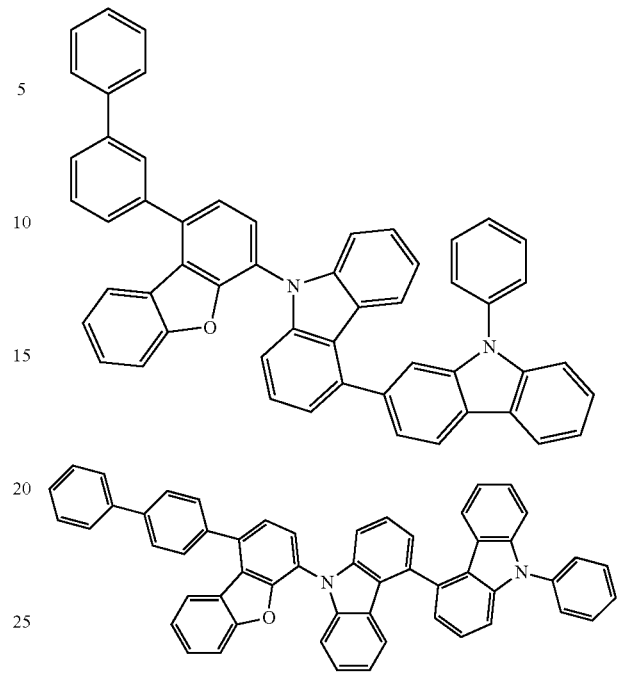
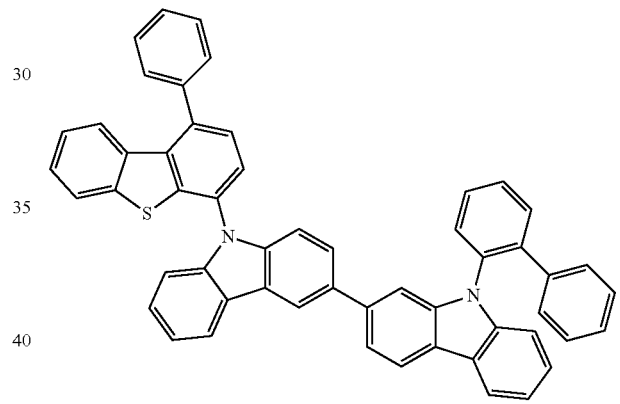

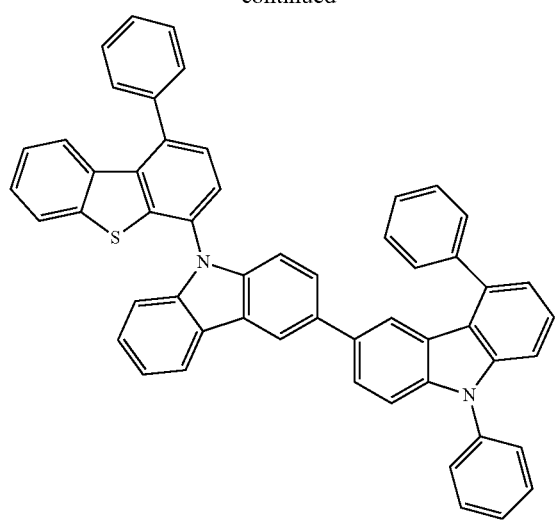

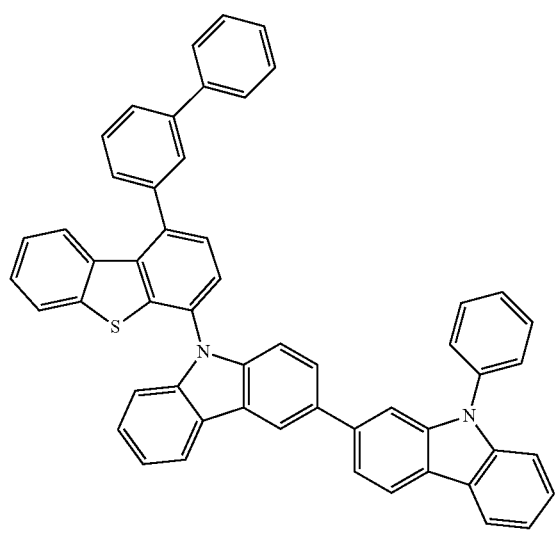 [SMILES: c1ccc(-c2cccc(-c3ccc(-n4c5ccccc5c5cc(-c6ccc7c8ccccc8n(-c8ccccc8)c7c6)ccc54)c4sc5ccccc5c34)c2)cc1]

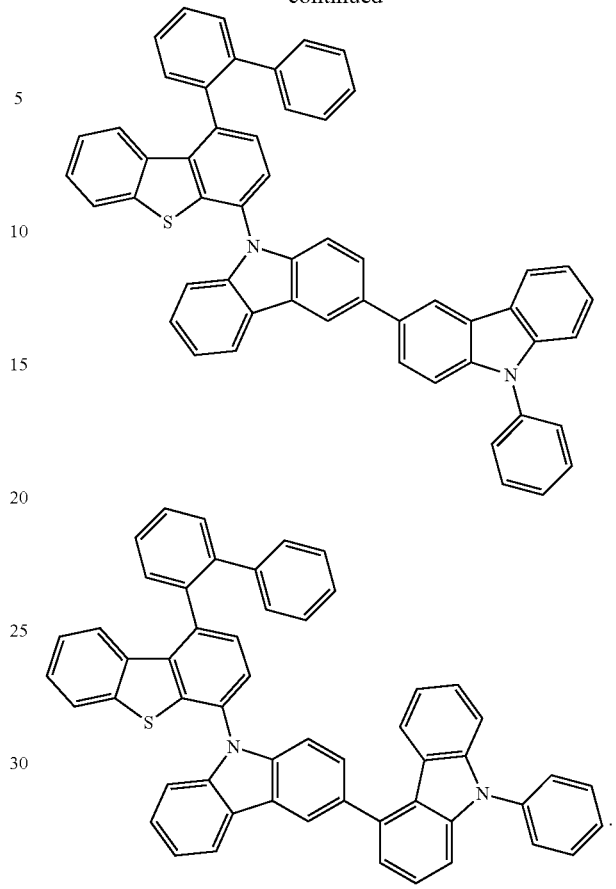

Another embodiment of the present specification provides an organic light emitting device including the compound described above.

The organic light emitting device provided in one embodiment of the present application includes a first electrode; a second electrode provided opposite to the first electrode; and one or more organic material layers provided between the first electrode and the second electrode, wherein one or more layers of the organic material layers include the compound.

In the present specification, a description of one member being placed "on" another member includes not only a case of the one member being in contact with the another member but a case of still another member being present between the two members.

In the present specification, a description of a certain part "including" certain constituents means capable of further including other constituents, and does not exclude other constituents unless particularly stated on the contrary.

The organic material layer of the organic light emitting device of the present application can be formed in a single layer structure, but can be formed in a multilayer structure in which two or more organic material layers are laminated. For example, as a representative example of the organic light emitting device of the present disclosure, the organic light emitting device can have a structure including a hole injection layer, a hole transfer layer, a light emitting layer, an electron transfer layer, an electron injection layer and the like as the organic material layer. However, the structure of the organic light emitting device is not limited thereto, and can include a smaller number of organic material layers.

In one embodiment of the present application, the organic material layer includes a light emitting layer, and the light emitting layer includes the compound.

In one embodiment of the present application, the organic material layer includes a light emitting layer, and the light emitting layer includes the compound as a host.

In one embodiment of the present application, the organic material layer includes a light emitting layer, and the light emitting layer includes the compound as a host, and further includes another host.

In one embodiment of the present application, the organic material layer includes a light emitting layer, and the light emitting layer includes the compound as a host, and further includes a host and a dopant.

In one embodiment of the present application, the organic material layer includes a light emitting layer, and the light emitting layer includes the compound as a second host, and further includes a first host.

In one embodiment of the present application, the light emitting layer includes a first host and a second host in a weight ratio of 2:8 to 8:2, and the second host is the compound of Chemical Formula 1.

In one embodiment of the present application, the light emitting layer includes a first host and a second host in a weight ratio of 1:1, and the second host is the compound of Chemical Formula 1.

In one embodiment of the present application, the light emitting layer further includes a dopant.

In one embodiment of the present application, the light emitting layer includes a first host and a second host, and further includes a dopant.

In one embodiment of the present application, the dopant is included in 1 parts by weight to 20 parts by weight with respect to 100 parts by weight of the host.

In one embodiment of the present application, the dopant is an iridium-based compound.

In one embodiment of the present application, the dopant compound can be selected from among the following compounds, but is not limited thereto:

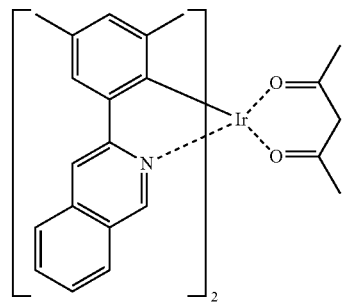

Dp-1

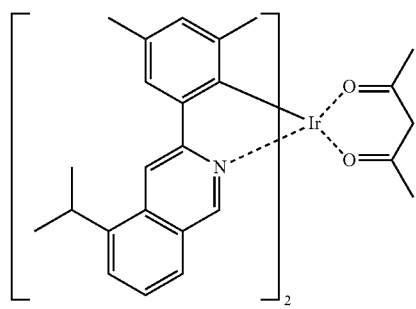

Dp-2

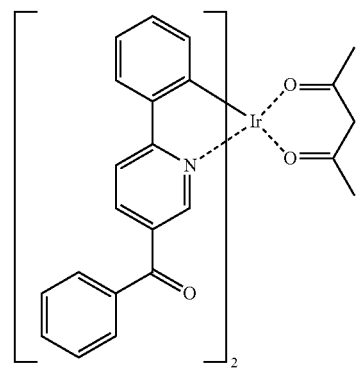

-continued

Dp-3

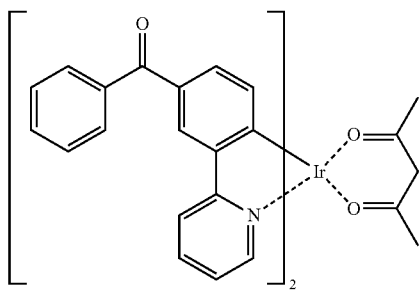

Dp-4

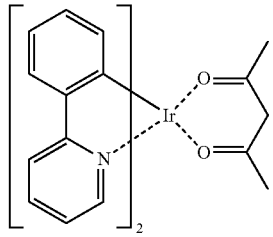

Dp-5

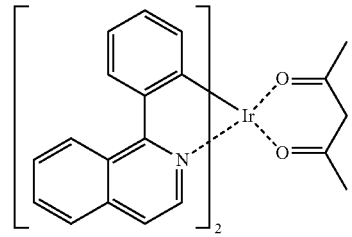

Dp-6

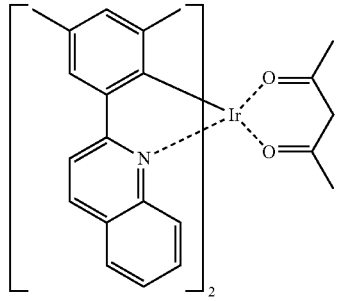

Dp-7

Dp-8
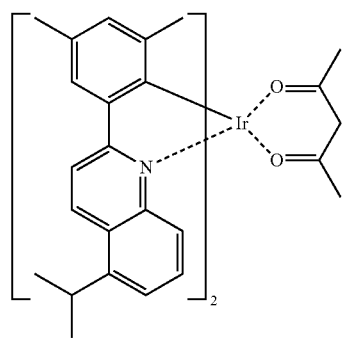
Dp-9
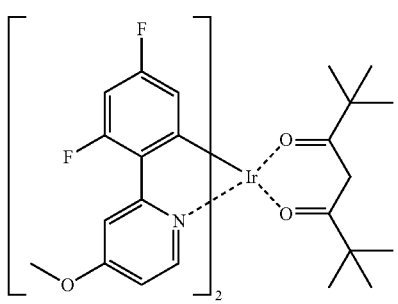
Dp-10
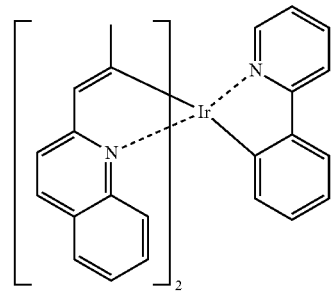
Dp-11
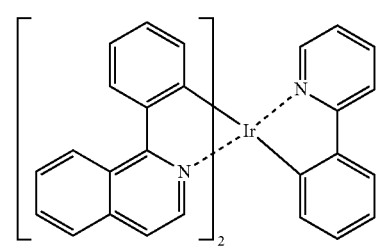
Dp-12
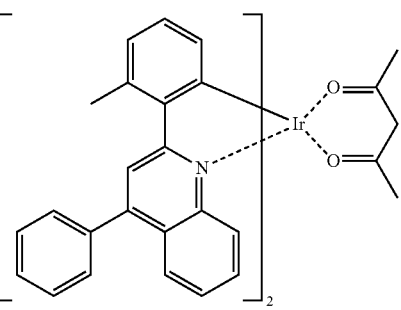
Dp-13
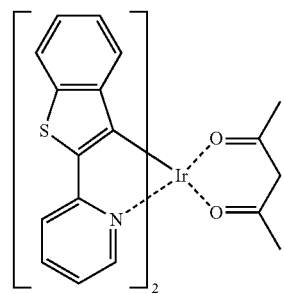
Dp-14
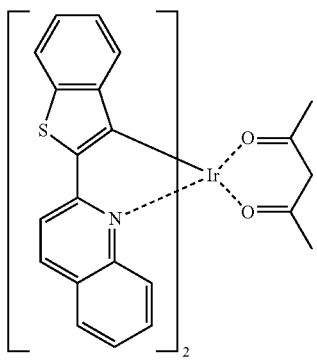
Dp-15
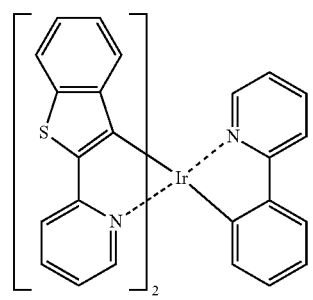
Dp-16
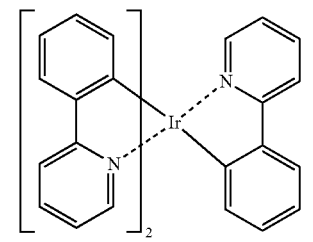
Dp-17
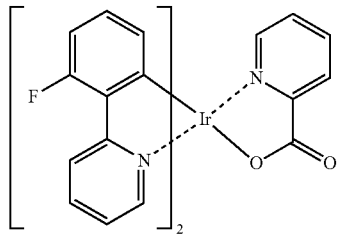

Dp-18
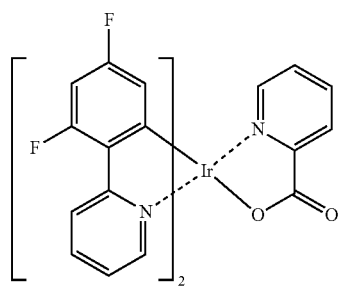
Dp-19
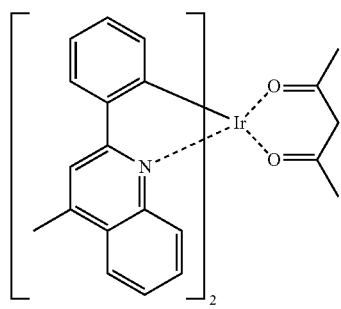
Dp-20
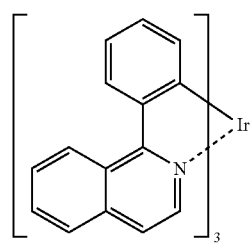
Dp-21
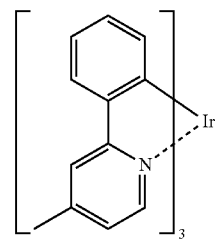
Dp-22
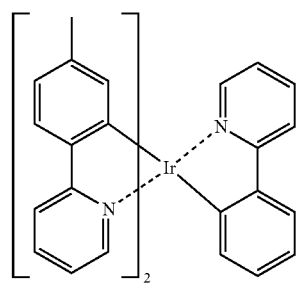
Dp-23
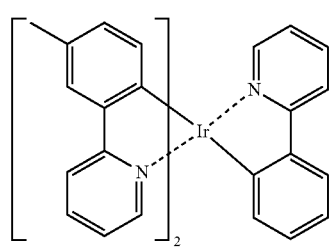
Dp-24
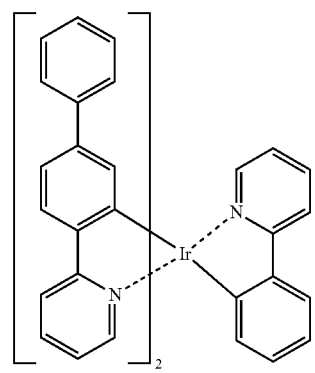
Dp-25
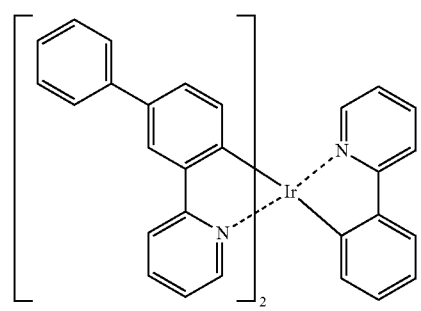
Dp-26
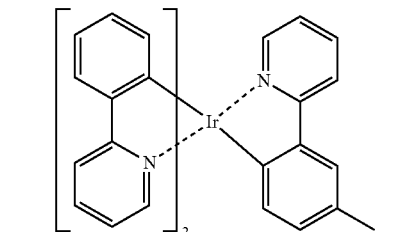
Dp-27
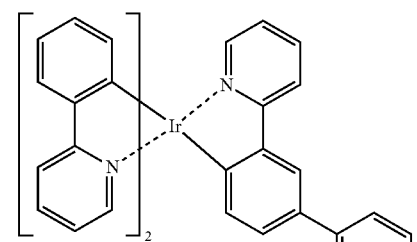
Dp-28
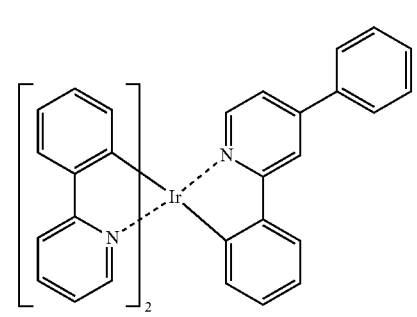

Dp-29
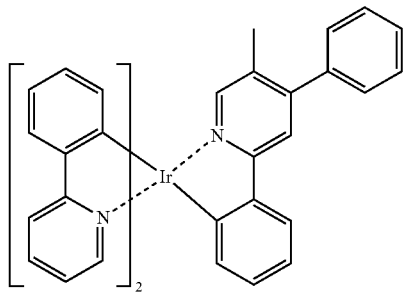
Dp-30
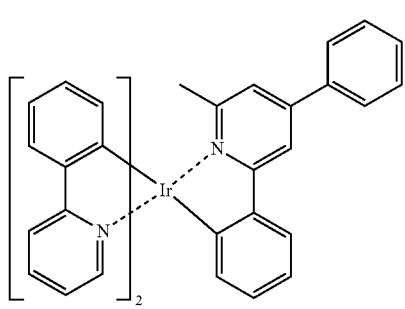
Dp-31
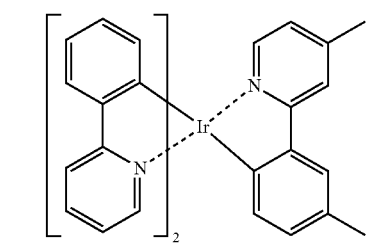
Dp-32
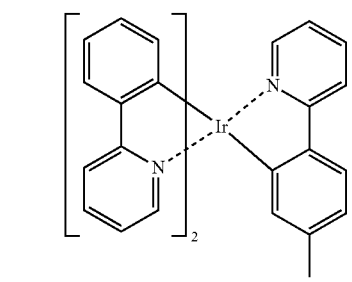
Dp-33
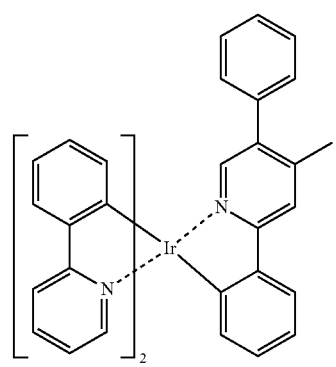
Dp-34
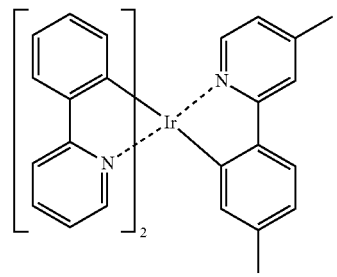
Dp-35
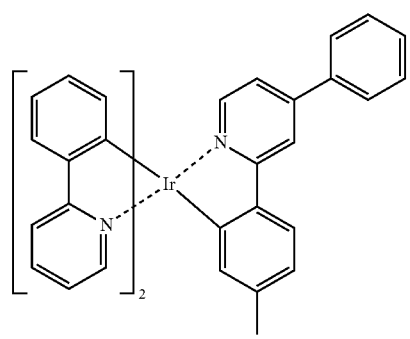
Dp-36
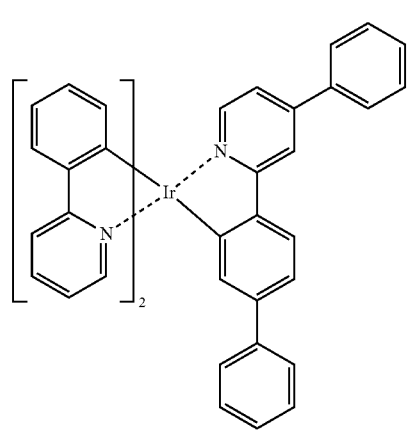
Dp-37
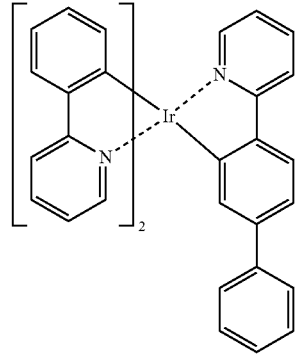

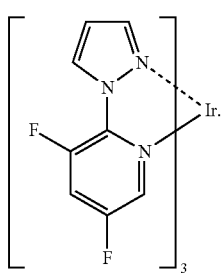

Dp-38

In one embodiment of the present application, the organic material layer includes a hole injection layer or a hole transfer layer.

In one embodiment of the present application, the organic material layer includes an electron blocking layer.

In one embodiment of the present application, the organic material layer includes a hole injection layer, a hole transfer layer, or an electron blocking layer.

In one embodiment of the present application, the organic material layer includes a hole injection layer, a hole transfer layer, and an electron blocking layer.

In one embodiment of the present application, the organic material layer includes a hole transfer layer, and the hole transfer layer includes two or more layers.

In one embodiment of the present application, the organic material layer includes a hole injection layer or a hole transfer layer, and the hole injection layer or the hole transfer layer includes the compound.

In one embodiment of the present application, the organic material layer includes a hole injection layer, a hole transfer layer, or a hole injection and transfer layer, and the hole injection layer, the hole transfer layer, or the hole injection and transfer layer includes the compound.

In one embodiment of the present application, the organic material layer includes an electron transfer layer or an electron injection layer, and the electron transfer layer or the electron injection layer includes the compound.

In one embodiment of the present application, the organic material layer includes an electron injection layer, an electron transfer layer, or an electron injection and transfer layer, and the electron injection layer, the electron transfer layer, or the electron injection and transfer layer includes the compound.

In one embodiment of the present application, the organic material layer includes a hole blocking layer.

In one embodiment of the present application, the organic material layer includes an electron transfer and injection layer.

In one embodiment of the present application, the organic material layer includes an electron transfer and injection layer, and the electron transfer and injection layer includes two or more layers.

In one embodiment of the present application, the organic light emitting device includes a first electrode; a second electrode provided opposite to the first electrode; a light emitting layer provided between the first electrode and the second electrode; and two or more organic material layers provided between the light emitting layer and the first electrode, or between the light emitting layer and the second electrode, wherein at least one of the two or more organic material layers includes the compound.

In another embodiment, the organic light emitting device can be an organic light emitting device having a structure in which an anode, one or more organic material layers and a cathode are consecutively laminated on a substrate (normal type).

In another embodiment, the organic light emitting device can be an organic light emitting device having a structure in a reverse direction in which a cathode, one or more organic material layers and an anode are consecutively laminated on a substrate (inverted type).

For example, a structure of the organic light emitting device according to one embodiment of the present application is illustrated in FIG. 1.

FIG. 1 illustrates a structure of the organic light emitting device in which a substrate (1), an anode (2), an organic material layer (3) and a cathode (4) are consecutively laminated.

FIG. 2 illustrates a structure of the organic light emitting device in which a substrate (1), an anode (2), a hole injection layer (5), a hole transfer layer (6), an electron blocking layer (7), a light emitting layer (8), a hole blocking layer (9) an electron transfer layer (10), an electron injection layer (11) and a cathode (4) are consecutively laminated. In such a structure, the compound can be included in the light emitting layer (8), however, the structure is not limited thereto.

The organic light emitting device of the present application can be manufactured using materials and methods known in the art, except that one or more layers of the organic material layers include the compound of the present application, that is, the above-described compound.

When the organic light emitting device includes a plurality of organic material layers, the organic material layers can be formed with materials the same as or different from each other.

For example, the organic light emitting device of the present application can be manufactured by consecutively laminating a first electrode, an organic material layer and a second electrode on a substrate. Herein, the organic light emitting device can be manufactured by forming an anode on a substrate by depositing a metal, a metal oxide having conductivity, or an alloy thereof using a physical vapor deposition (PVD) method such as sputtering or e-beam evaporation, and forming an organic material layer including a hole injection layer, a hole transfer layer, a light emitting layer and an electron transfer layer thereon, and then depositing a material capable of being used as a cathode thereon. In addition to such a method, the organic light emitting device can also be manufactured by consecutively depositing a cathode material, an organic material layer and an anode material on a substrate.

In addition, the compound of Chemical Formula 1 can be formed into an organic material layer using a solution coating method as well as a vacuum deposition method when manufacturing the organic light emitting device. Herein, the solution coating method means spin coating, dip coating, doctor blading, inkjet printing, screen printing, a spray method, roll coating and the like, but is not limited thereto.

In addition to such as method, the organic light emitting device can also be manufactured by consecutively laminating a cathode material, an organic material layer and an anode material on a substrate (International Patent Application Laid-Open Publication No. WO2003/012890). However, the manufacturing method is not limited thereto.

In one embodiment of the present application, the first electrode is an anode, and the second electrode is a cathode.

In another embodiment, the first electrode is a cathode, and the second electrode is an anode.

As the anode material, materials having large work function are normally preferred so that hole injection to an organic material layer is smooth. Specific examples of the anode material capable of being used in the present disclosure include metals such as vanadium, chromium, copper, zinc and gold, or alloys thereof; metal oxides such as zinc oxide, indium oxide, indium tin oxide (ITO) and indium zinc oxide (IZO); combinations of metals and oxides such as ZnO:Al or $SnO_2$:Sb; conductive polymers such as poly(3-methylthiophene), poly[3,4-(ethylene-1,2-dioxy)thiophene] (PEDOT), polypyrrole and polyaniline, but are not limited thereto.

As the cathode material, materials having small work function are normally preferred so that electron injection to an organic material layer is smooth. Specific examples of the cathode material include metals such as magnesium, calcium, sodium, potassium, titanium, indium, yttrium, lithium, gadolinium, aluminum, silver, tin and lead, or alloys thereof; multilayer structure materials such as LiF/Al or $LiO_2$/Al, and the like, but are not limited thereto.

The hole injection layer is a layer that injects holes from an electrode, and the hole injection material is preferably a compound that has an ability to transfer holes, therefore, has a hole injection effect in an anode, has an excellent hole injection effect for a light emitting layer or a light emitting material, prevents excitons generated in the light emitting layer from moving to an electron injection layer or an electron injection material, and in addition thereto, has an excellent thin film forming ability. The highest occupied molecular orbital (HOMO) of the hole injection material is preferably in between the work function of an anode material and the HOMO of surrounding organic material layers. Specific examples of the hole injection material include metal porphyrins, oligothiophene, arylamine-based organic materials, hexanitrile hexaazatriphenylene-based organic materials, quinacridone-based organic materials, perylene-based organic materials, anthraquinone, and polyaniline- and polythiophene-based conductive polymers, and the like, but are not limited thereto.

The hole transfer layer is a layer that receives holes from a hole injection layer and transfers the holes to a light emitting layer, and as the hole transfer material, materials capable of receiving holes from an anode or a hole injection layer, moving the holes to a light emitting layer, and having high mobility for the holes are suitable. Specific examples thereof include arylamine-based organic materials, conductive polymers, block copolymers having conjugated parts and non-conjugated parts together, and the like, but are not limited thereto.

The light emitting material is a material capable of emitting light in a visible light region by receiving holes and electrons from a hole transfer layer and an electron transfer layer, respectively, and binding the holes and the electrons, and is preferably a material having favorable quantum efficiency for fluorescence or phosphorescence. Specific examples thereof include 8-hydroxyquinoline aluminum complexes ($Alq_3$); carbazole-based compounds; dimerized styryl compounds; BAlq; 10-hydroxybenzoquinoline-metal compounds; benzoxazole-, benzothiazole- and benzimidazole-based compounds; poly (p-phenylenevinylene) (PPV)-based polymers; spiro compounds; polyfluorene, rubrene, and the like, but are not limited thereto.

The light emitting layer can include a host material and a dopant material. The host material includes fused aromatic ring derivatives, heteroring-containing compounds or the like. Specifically, the fused aromatic ring derivative includes anthracene derivatives, pyrene derivatives, naphthalene derivatives, pentacene derivatives, phenanthrene compounds, fluoranthene compounds and the like, and the heteroring-containing compound includes compounds, dibenzofuran derivatives, ladder-type furan compounds, pyrimidine derivatives and the like, however, the material is not limited thereto.

The electron transfer layer is a layer that receives electrons from an electron injection layer and transfers the electrons to a light emitting layer, and as the electron transfer material, materials capable of favorably receiving electrons from a cathode, moving the electrons to a light emitting layer, and having high mobility for the electrons are suitable. Specific examples thereof include Al complexes of 8-hydroxyquinoline; complexes including $Alq_3$; organic radical compounds; hydroxyflavon-metal complexes, and the like, but are not limited thereto. The electron transfer layer can be used together with any desired cathode material as used in the art. Particularly, examples of the suitable cathode material include common materials that have small work function, and in which an aluminum layer or a silver layer follows. Specifically, the cathode material includes cesium, barium, calcium, ytterbium and samarium, and in each case, an aluminum layer or a silver layer follows.

The electron injection layer is a layer that injects electrons from an electrode, and the electron injection material is preferably a compound that has an ability to transfer electrons, has an electron injection effect from a cathode, has an excellent electron injection effect for a light emitting layer or a light emitting material, prevents excitons generated in the light emitting layer from moving to a hole injection layer, and in addition, has an excellent thin film forming ability. Specific examples thereof include fluorenone, anthraquinodimethane, diphenoquinone, thiopyran dioxide, oxazole, oxadiazole, triazole, imidazole, perylene tetracarboxylic acid, fluorenylidene methane, anthrone or the like, and derivatives thereof, metal complex compounds, nitrogen-containing 5-membered ring derivatives, and the like, but are not limited thereto.

The metal complex compound includes 8-hydroxyquinolinato lithium, bis (8-hydroxyquinolinato) zinc, bis (8-hydroxy-quinolinato)copper, bis(8-hydroxyquinolinato)manganese, tris (8-hydroxyquinolinato) aluminum, tris (2-methyl-8-hydroxy-quinolinato) aluminum, tris (8-hydroxyquinolinato) gallium, bis (10-hydroxybenzo[h] quinolinato)beryllium, bis (10-hydroxy-benzo[h]quinolinato)zinc, bis(2-methyl-8-quinolinato)-chlorogallium, bis (2-methyl-8-quinolinato) (o-cresolato)-gallium, bis (2-methyl-8-quinolinato) (1-naphtholato) aluminum, bis (2-methyl-8-quinolinato) (2-naphtholato) gallium and the like, but is not limited thereto.

The hole blocking layer is a layer blocking holes from reaching a cathode and can be generally formed under the same condition as the hole injection layer. Specifically, oxadiazole derivatives, triazole derivatives, phenanthroline derivatives, BCP, aluminum complexes and the like are included, however, the hole blocking layer is not limited thereto.

The organic light emitting device according to the present specification can be a top-emission type, a bottom-emission type or a dual-emission type depending on the materials used.

EXAMPLES

Methods for preparing the compound of Chemical Formula 1 and manufacturing an organic light emitting device including the same will be specifically described in the following examples. However, the following examples are for illustrative purposes only, and the scope of the present specification is not limited thereby.

Preparation Example 1

Preparation Example 1-1: Synthesis of Compound A2

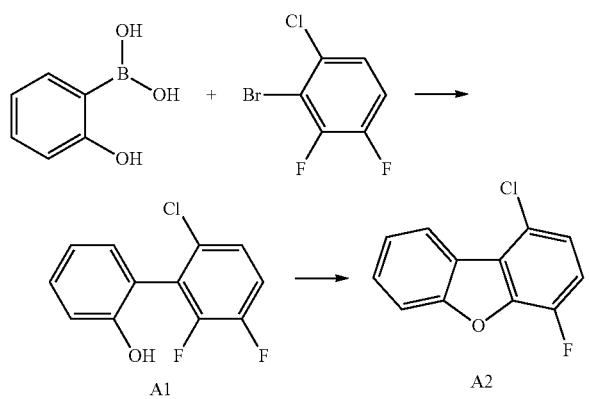

1) Preparation of Compound A1

(2-Hydroxyphenyl) boronic acid (50 g, 363 mmol) and 2-bromo-1-chloro-3,4-difluorobenzene (82.5 g, 363 mmol) were dissolved in tetrahydrofuran (1000 mL). A 1.5 M aqueous calcium carbonate solution (300 mL) and bis(tri-t-butyl-phosphine)palladium(0) (1.9 g, 3.6 mmol) were introduced thereto, and the result was refluxed for 1.5 hours. After the reaction was finished, the result was cooled to room temperature, the water layer was separated and removed, the result was dried using anhydrous magnesium sulfate, and a mixture obtained by vacuum concentrating the result was recrystallized using ethanol to obtain Compound A1. (74.9 g, yield 86%; MS: [M+H]$^+$=241)

2) Preparation of Compound A2

After dissolving Compound A1 (89.7 g, 297.5 mmol) and calcium carbonate (123.3 g, 892 mmol) in N-methyl-2-pyrrolidone (900 mL), the result was stirred for 2 hours while heating. The temperature was lowered to room temperature, and the result was reverse precipitated in water and filtered. The result was completely dissolved in dichloromethane, then washed with water, dried with anhydrous magnesium sulfate, then vacuum concentrated, recrystallized using ethanol, and dried to obtain Compound A2. (53.8 g, yield 78%; MS: [M+H]$^+$=221)

Preparation Example 1-2: Synthesis of Compound A3

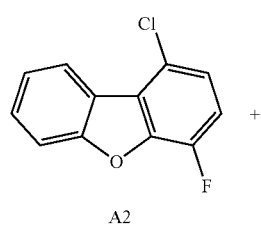

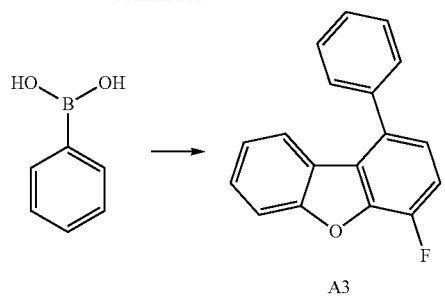

Compound A2 (30 g, 136 mmol) and phenylboronic acid (18.2 g, 150 mmol) were dissolved in tetrahydrofuran (300 mL). A 1.5 M aqueous calcium carbonate solution (150 mL) and bis (tri-t-butylphosphine)palladium(0) (0.7 g, 1.4 mmol) were introduced thereto, and the result was refluxed for 5 hours. After the reaction was finished, the result was cooled to room temperature, the water layer was separated and removed, the result was dried using anhydrous magnesium sulfate, and a mixture obtained by vacuum concentrating the result was recrystallized using ethanol to obtain Compound A3. (31.3 g, yield 88%; MS: [M+H]$^+$=263)

Preparation Example 1-3: Synthesis of Compound A4

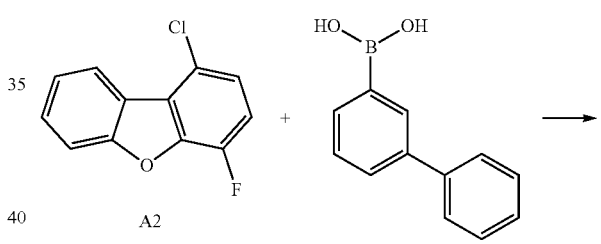

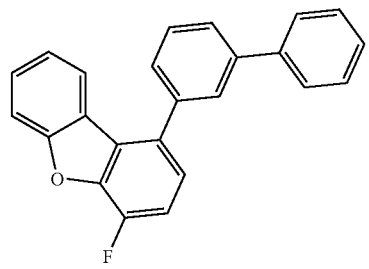

Compound A4 (26.0 g, yield 85%, MS:[M+H]$^+$=339) was prepared in the same manner as in the method for preparing Compound A3 in Preparation Example 1-2 except that [1,1'-biphenyl]-3-ylboronic acid was used instead of phenylboronic acid.

Preparation Example 1-4: Synthesis of Compound A5

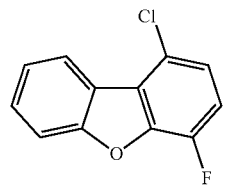

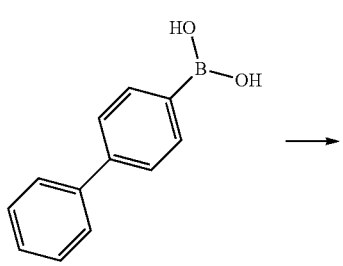

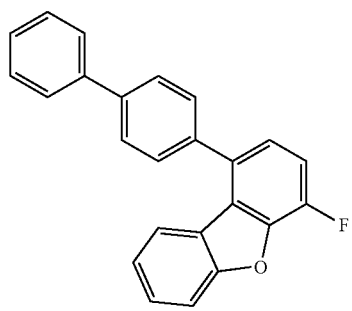

Compound A5 (27.4 g, yield 89%, MS:[M+H]$^+$=339) was prepared in the same manner as in the method for preparing Compound A3 in Preparation Example 1-2 except that [1,1'-biphenyl]-4-ylboronic acid was used instead of phenylboronic acid.

Preparation Example 1-5: Synthesis of Compound A6

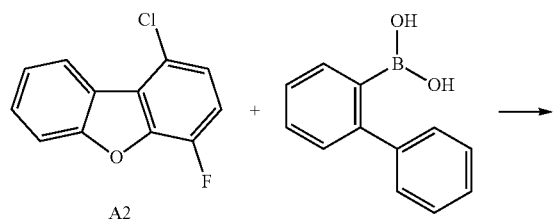

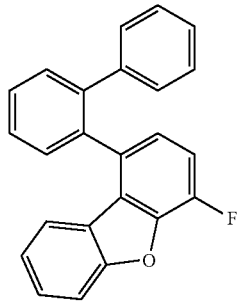

Compound A6 (20.6 g, yield 67%, MS: [M+H]$^+$=339) was prepared in the same manner as in the method for preparing Compound A3 in Preparation Example 1-2 except that [1,1'-biphenyl]-2-ylboronic acid was used instead of phenylboronic acid.

Preparation Example 1-6: Synthesis of Compound A8

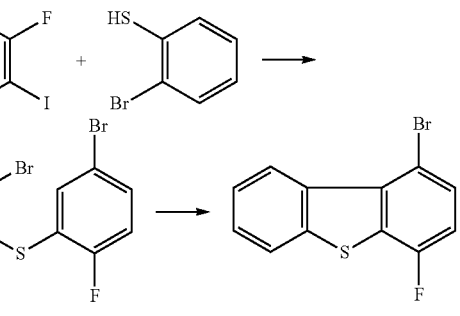

1) Preparation of Compound A7

4-Bromo-1-fluoro-2-iodobenzene (50 g, 166.2 mmol) and 2-bromothiophenol (37.7 g, 199.4 mmol) were dispersed into ethanol (500 ml), and after introducing sodium hydroxide (8.6 g, 216.0 mmol) thereto, the result was refluxed for 6 hours. After the reaction was finished, the result was cooled to room temperature, extracted by introducing water thereto, and a mixture obtained by vacuum distilling the obtained organic layer was filtered using silica gel to prepare Compound A7 (47.5 g, yield 79%; MS:[M+H]$^+$=361).

2) Preparation of Compound A8

After dissolving Compound A7 (47.5 g, 131.2 mmol) in dichloromethane (500 ml), 2,3-dichloro-5,6-dicyano-1,4-benzoquinone (35.7 g, 157.4 mmol) was introduced thereto, and the result was stirred for 24 hours at room temperature. After the reaction was finished, the result was extracted three times using an excess amount of water. The organic layer was dried using magnesium sulfate, and a mixture obtained by vacuum distilling the result was purified using a short column to prepare Compound A8 (27.9 g, yield 76%; MS: [M+H]$^+$=281).

Preparation Example 1-7: Synthesis of Compound A9

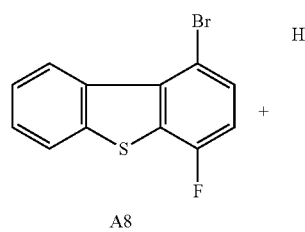

Compound A9 (17.0 g, yield 86%, MS:[M+H]$^+$=279) was prepared in the same manner as in the method for preparing Compound A3 in Preparation Example 1-2 except that Compound A8 was used instead of Compound A2.

Preparation Example 1-8: Synthesis of Compound A10

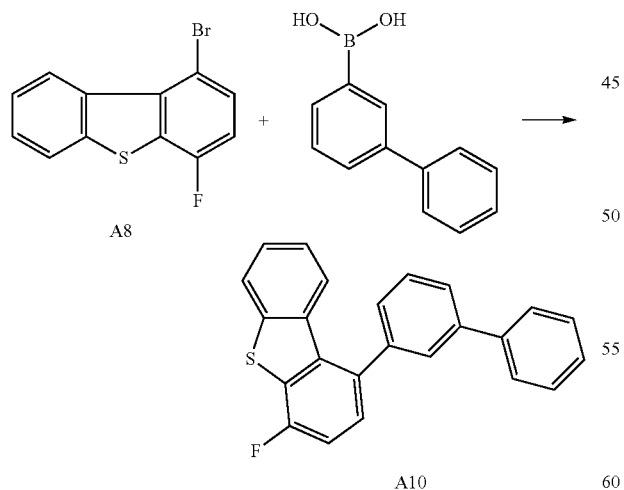

Compound A10 (19.9 g, yield 79%, MS:[M+H]$^+$=355) was prepared in the same manner as in the method for preparing Compound A3 in Preparation Example 1-2 except that Compound A8 and [1,1'-biphenyl]-3-ylboronic acid were used instead of Compound A2 and phenylboronic acid.

Preparation Example 1-9: Synthesis of Compound A11

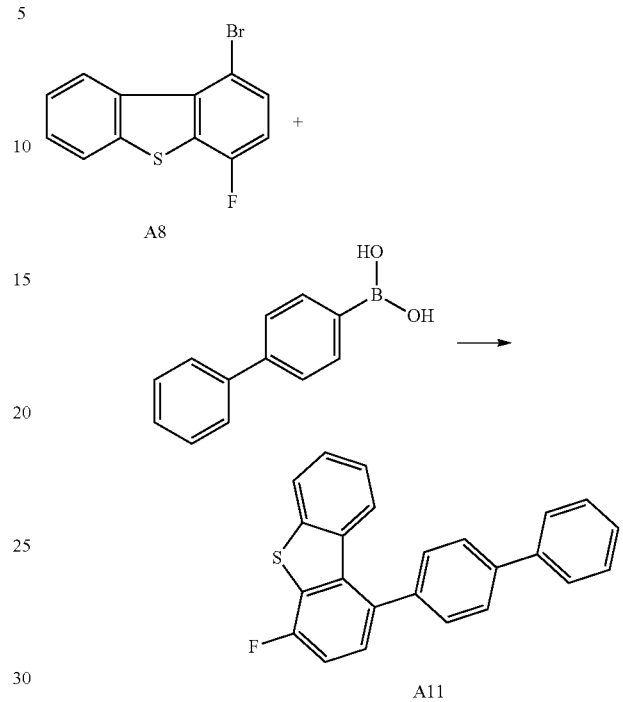

Compound A11 (21.0 g, yield 83%, MS:[M+H]$^+$=355) was prepared in the same manner as in the method for preparing Compound A3 in Preparation Example 1-2 except that Compound A8 and [1,1'-biphenyl]-4-ylboronic acid were used instead of Compound A2 and phenylboronic acid.

Preparation Example 1-10: Synthesis of Compound A12

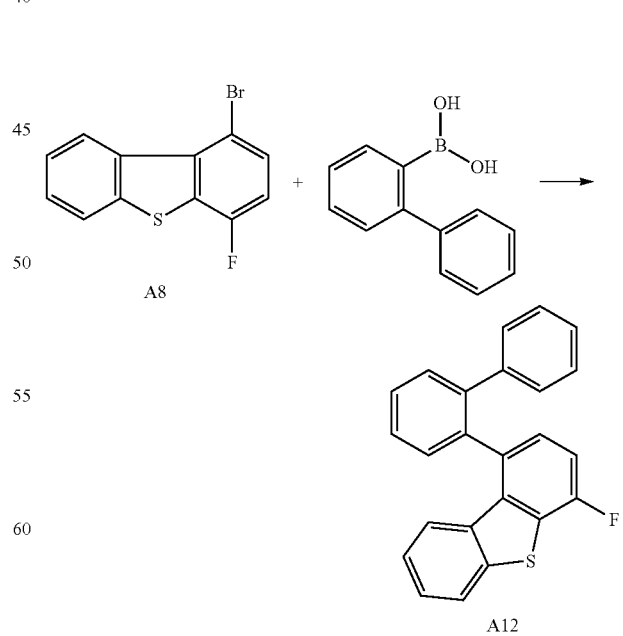

Compound A12 (17.3 g, yield 69%, MS:[M+H]$^+$=355) was prepared in the same manner as in the method for preparing Compound A3 in Preparation Example 1-2 except that Compound A8 and [1,1'-biphenyl]-2-ylboronic acid were used instead of Compound A2 and phenylboronic acid.

Preparation Example 2-1: Synthesis of Compound B1

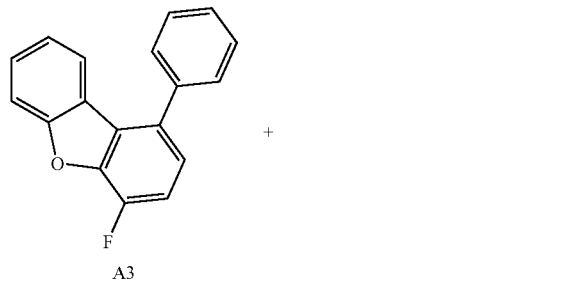

2-Bromo-9H-carbazole (20 g, 81.2 mmol) and potassium-tert-butoxide (18.2 g, 163 mmol) were introduced to dimethylformamide (300 mL), and the result was heated while stirring. When the result started to reflux, Compound A3 (21.3 g, 81.2 mmol) was introduced thereto, and the result was refluxed for 4 hours. The temperature was lowered to room temperature, and the result was reverse precipitated in water and filtered. The filtered material was dissolved in chloroform, washed with water, the water layer was separated and removed, the result was dried using anhydrous magnesium sulfate, and a mixture obtained by vacuum concentrating the result was recrystallized using tetrahydrofuran to obtain Compound B1. (34.7 g, yield 87%; MS: $[M+H]^+=488$)

Preparation Example 2-2: Synthesis of Compound B2

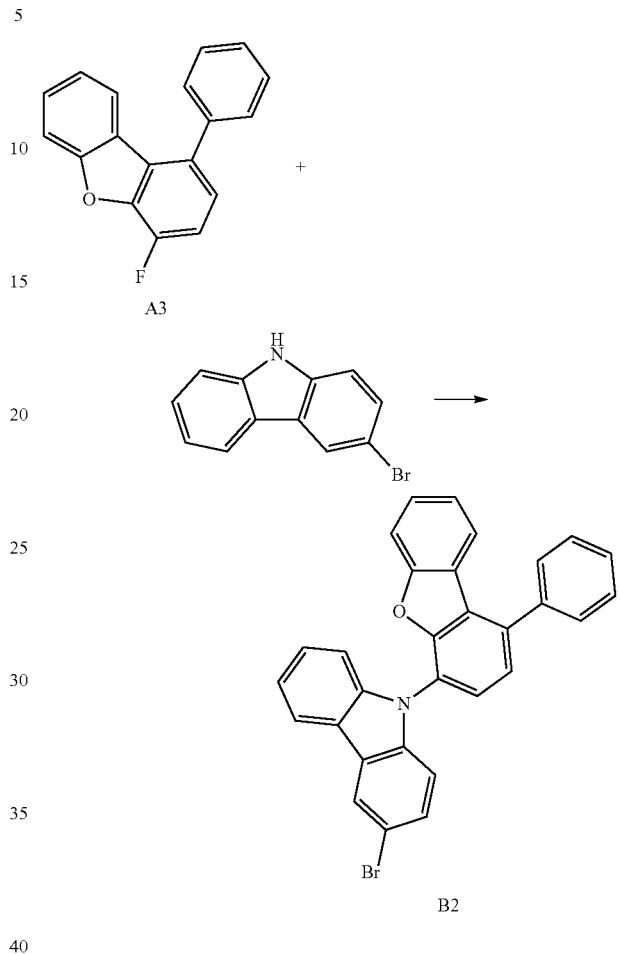

Compound B2 (33.5 g, yield 84%; MS:$[M+H]^+=488$) was prepared in the same manner as in the method for preparing Compound B1 in Preparation Example 2-1 except that 3-bromo-9H-carbazole was used instead of 2-bromo-9H-carbazole.

Preparation Example 2-3: Synthesis of Compound B3

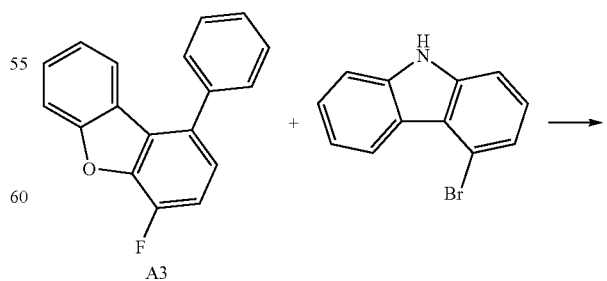

-continued

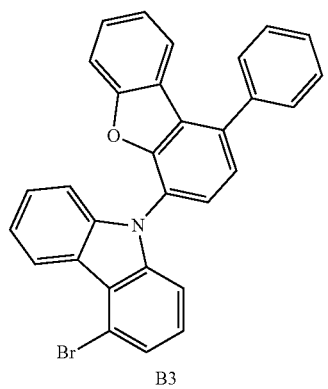

B3

Compound B3 (33.0 g, yield 83%; MS:[M+H]$^+$=488) was prepared in the same manner as in the method for preparing Compound B1 in Preparation Example 2-1 except that 4-bromo-9H-carbazole was used instead of 2-bromo-9H-carbazole.

Preparation Example 2-4: Synthesis of Compound B4

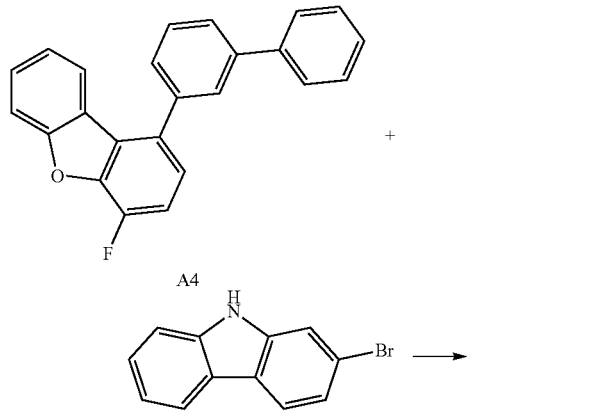

B4

Compound B4 (29.7 g, yield 89%; MS:[M+H]$^+$=564) was prepared in the same manner as in the method for preparing Compound B1 in Preparation Example 2-1 except that Compound A4 was used instead of Compound A3.

Preparation Example 2-5: Synthesis of Compound B5

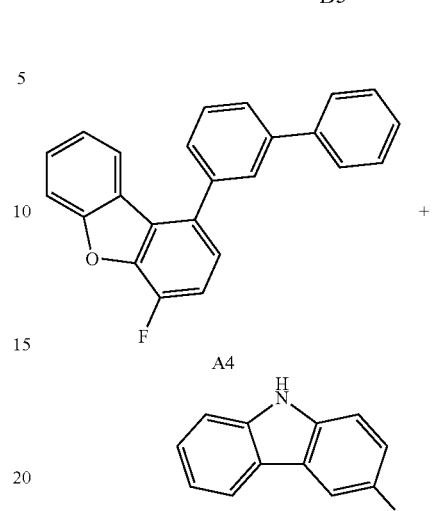

B5

Compound B5 (29.2 g, yield 87%; MS: [M+H]$^+$=564) was prepared in the same manner as in the method for preparing Compound B1 in Preparation Example 2-1 except that Compound A4 and 3-bromo-9H-carbazole were used instead of Compound A3 and 2-bromo-9H-carbazole.

Preparation Example 2-6: Synthesis of Compound B6

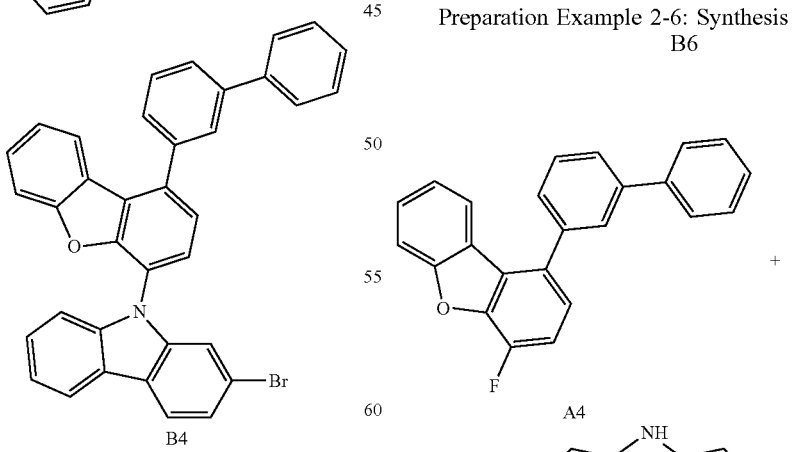

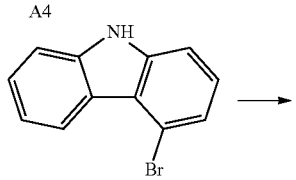

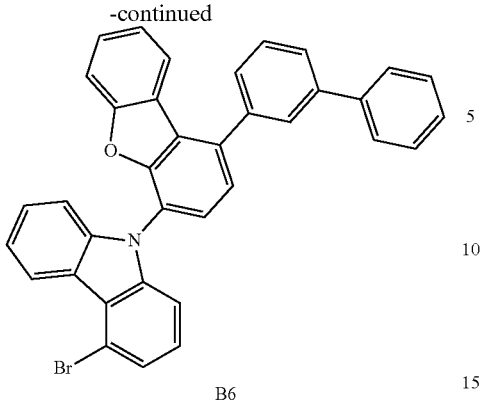

B6

Compound B6 (28.6 g, yield 86%; MS: [M+H]⁺=564) was prepared in the same manner as in the method for preparing Compound B1 in Preparation Example 2-1 except that Compound A4 and 4-bromo-9H-carbazole were used instead of Compound A3 and 2-bromo-9H-carbazole.

Preparation Example 2-7: Synthesis of Compound B7

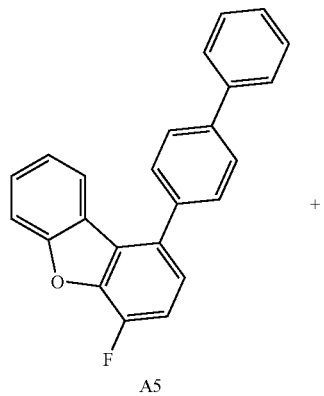

B7

Compound B7 (28.0 g, yield 84%; MS:[M+H]⁺=564) was prepared in the same manner as in the method for preparing Compound B1 in Preparation Example 2-1 except that Compound A5 was used instead of Compound A3.

Preparation Example 2-8: Synthesis of Compound B8

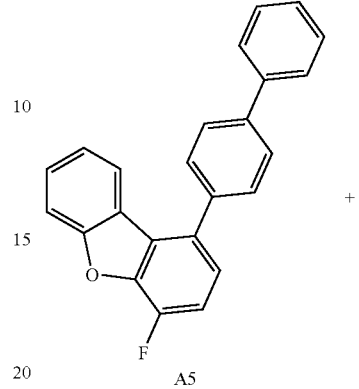

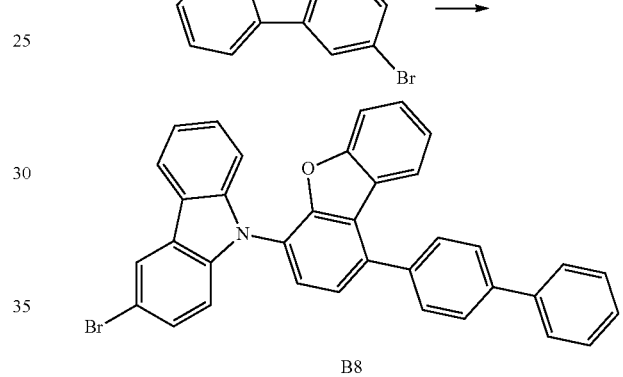

B8

Compound B8 (29.3 g, yield 88%; MS:[M+H]⁺=564) was prepared in the same manner as in the method for preparing Compound B1 in Preparation Example 2-1 except that Compound A5 and 3-bromo-9H-carbazole were used instead of Compound A3 and 2-bromo-9H-carbazole.

Preparation Example 2-9: Synthesis of Compound B9

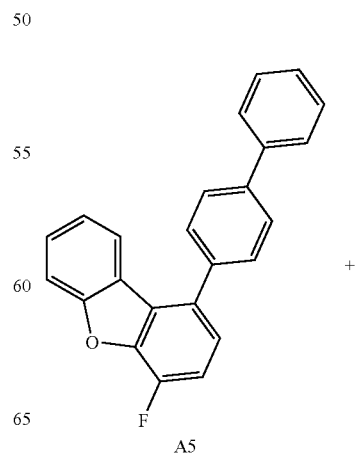

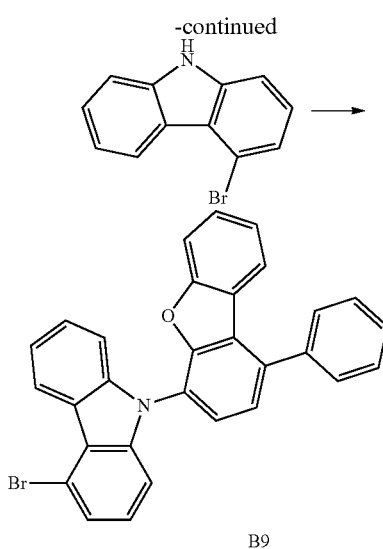

B9

Compound B9 (28.5 g, yield 86%; MS: [M+H]⁺=564) was prepared in the same manner as in the method for preparing Compound B1 in Preparation Example 2-1 except that Compound A5 and 4-bromo-9H-carbazole were used instead of Compound A3 and 2-bromo-9H-carbazole.

Preparation Example 2-10: Synthesis of Compound B10

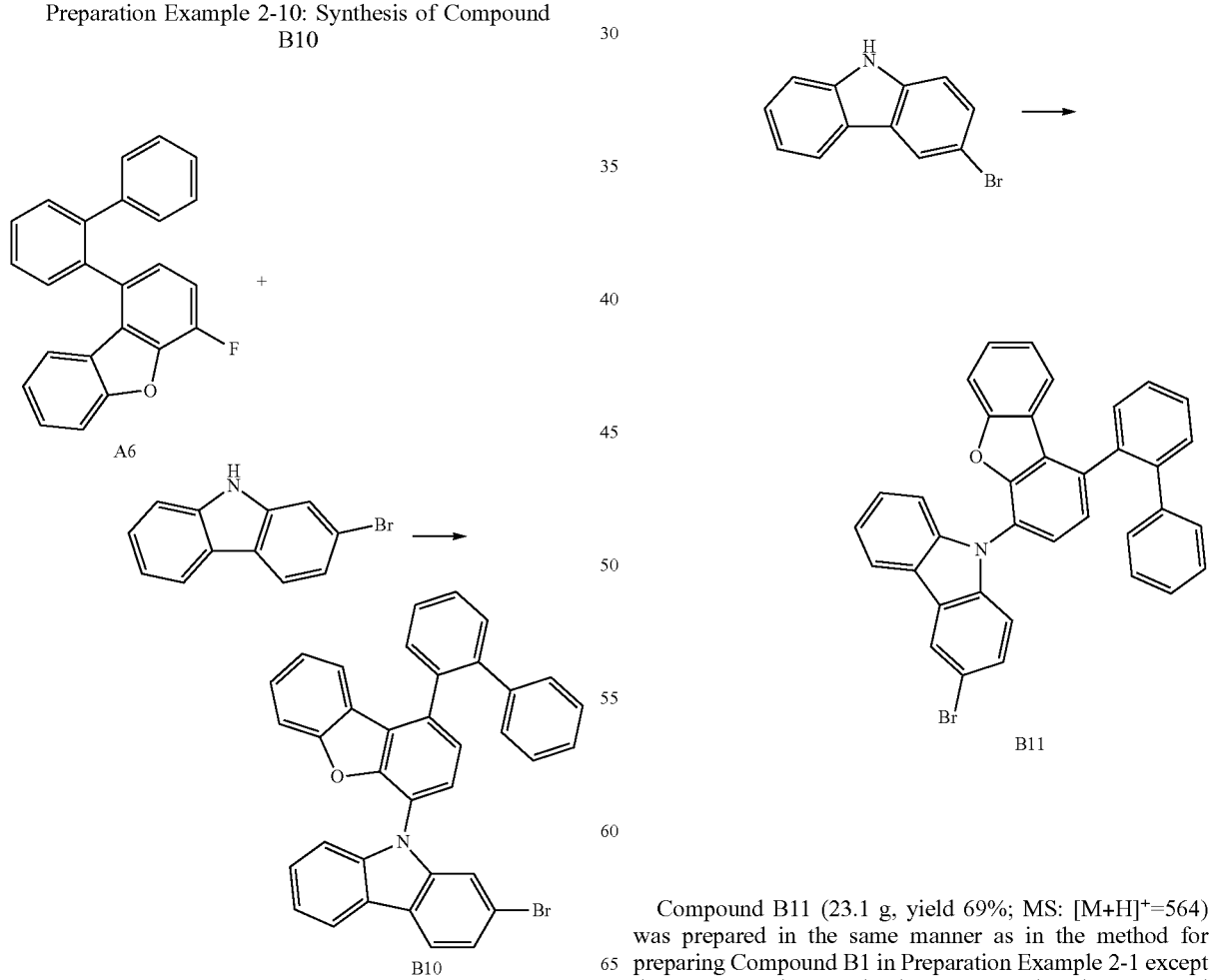

Compound B10 (22.6 g, yield 68%; MS: [M+H]⁺=564) was prepared in the same manner as in the method for preparing Compound B1 in Preparation Example 2-1 except that Compound A6 was used instead of Compound A3.

Preparation Example 2-11: Synthesis of Compound B11

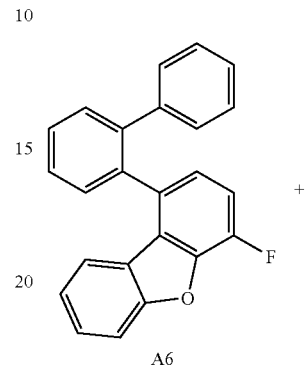

Compound B11 (23.1 g, yield 69%; MS: [M+H]⁺=564) was prepared in the same manner as in the method for preparing Compound B1 in Preparation Example 2-1 except that Compound A6 and 3-bromo-9H-carbazole were used instead of Compound A3 and 2-bromo-9H-carbazole.

Preparation Example 2-12: Synthesis of Compound B12

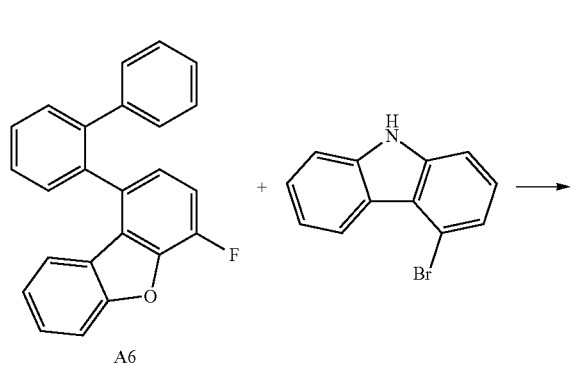

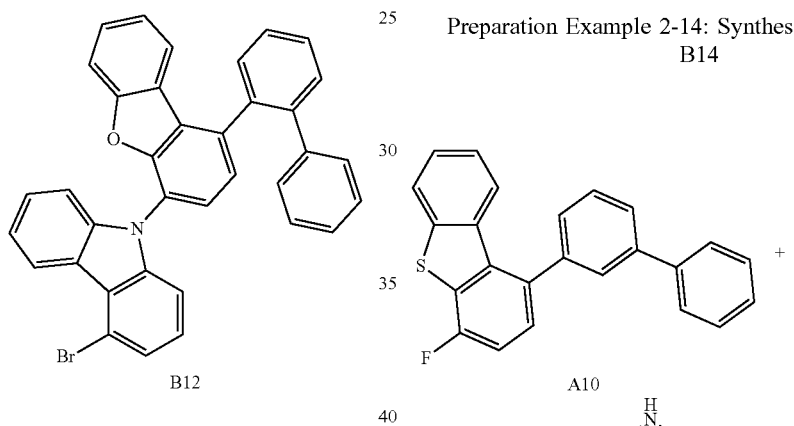

Compound B12 (20.7 g, yield 62%; MS: [M+H]$^+$=564) was prepared in the same manner as in the method for preparing Compound B1 in Preparation Example 2-1 except that Compound A6 and 4-bromo-9H-carbazole were used instead of Compound A3 and 2-bromo-9H-carbazole.

Preparation Example 2-13: Synthesis of Compound B13

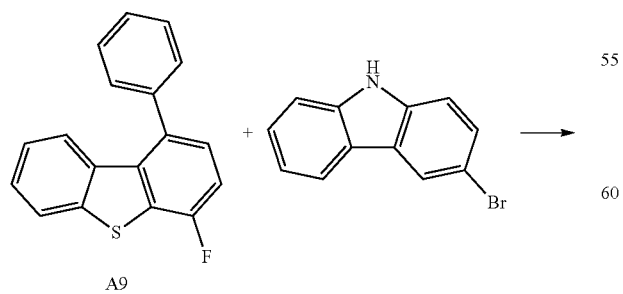

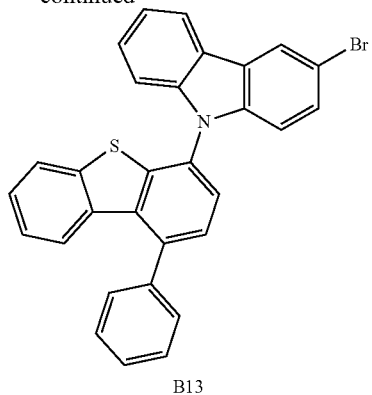

Compound B13 (23.0 g, yield 85%; MS:[M+H]$^+$=504) was prepared in the same manner as in the method for preparing Compound B1 in Preparation Example 2-1 except that Compound A9 and 3-bromo-9H-carbazole were used instead of Compound A3 and 2-bromo-9H-carbazole.

Preparation Example 2-14: Synthesis of Compound B14

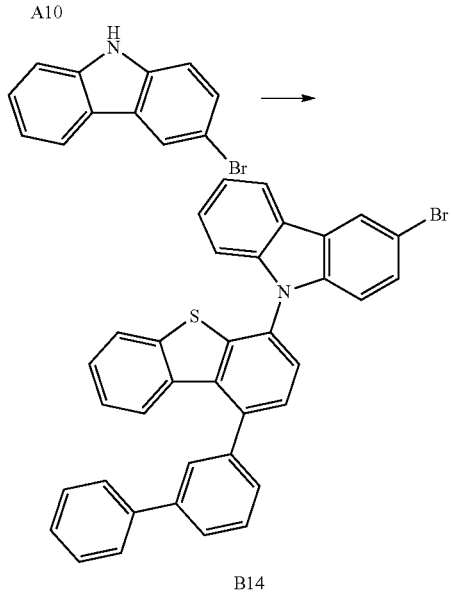

Compound B14 (26.3 g, yield 84%; MS: [M+H]$^+$=580) was prepared in the same manner as in the method for preparing Compound B1 in Preparation Example 2-1 except that Compound A10 and 3-bromo-9H-carbazole were used instead of Compound A3 and 2-bromo-9H-carbazole.

Preparation Example 2-15: Synthesis of Compound B15

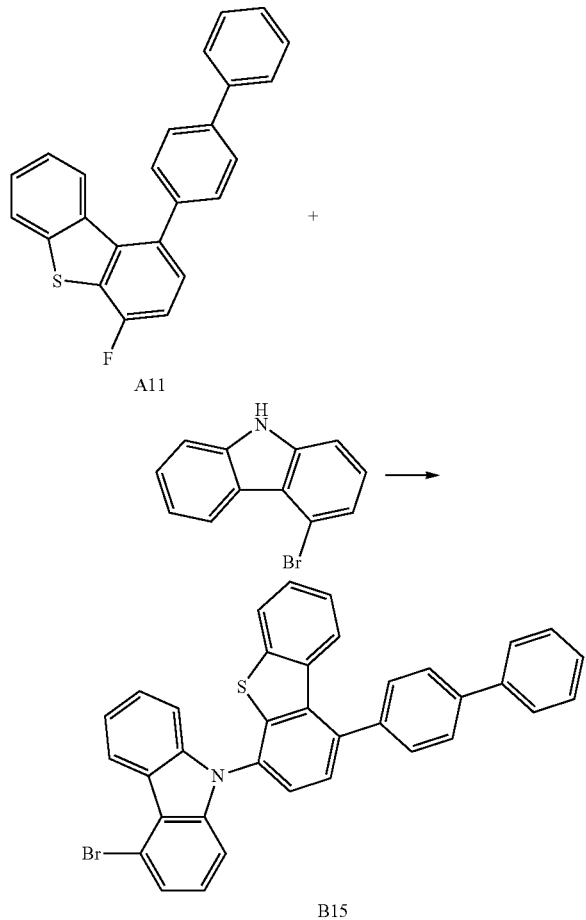

B15

Compound B15 (27.7 g, yield 88%; MS:[M+H]$^+$=580) was prepared in the same manner as in the method for preparing Compound B1 in Preparation Example 2-1 except that Compound A11 and 4-bromo-9H-carbazole were used instead of Compound A3 and 2-bromo-9H-carbazole.

Preparation Example 2-16: Synthesis of Compound B16

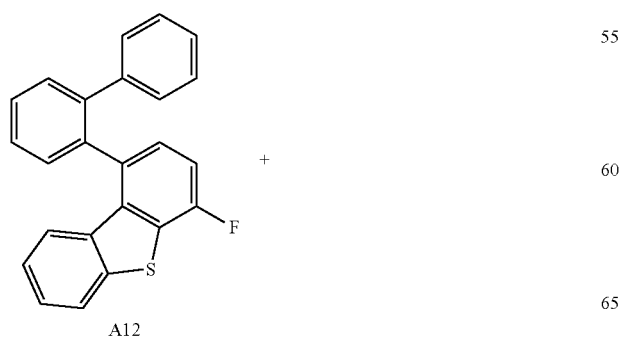

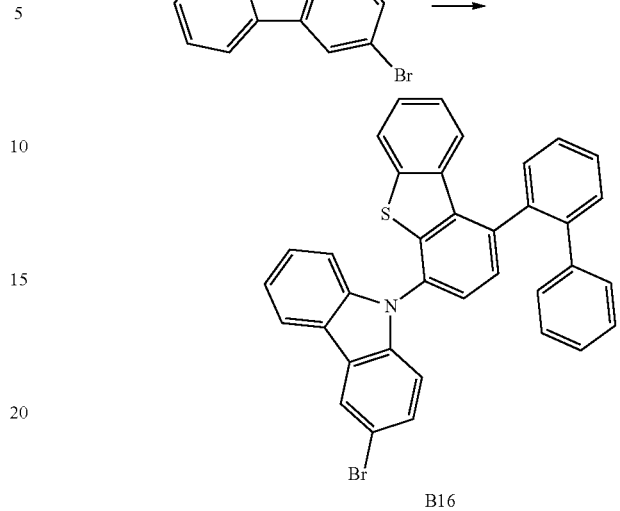

B16

Compound B16 (20.9 g, yield 67%; MS:[M+H]$^+$=580) was prepared in the same manner as in the method for preparing Compound B1 in Preparation Example 2-1 except that Compound A12 and 3-bromo-9H-carbazole were used instead of Compound A3 and 2-bromo-9H-carbazole.

EXAMPLE

Example 1: Preparation of Compound 1

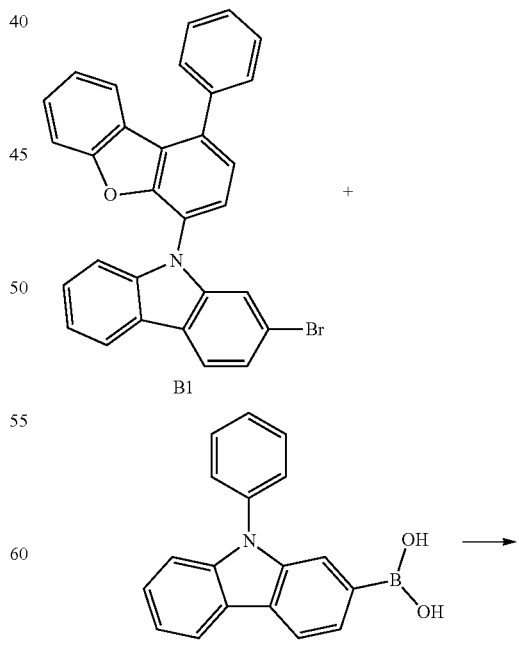

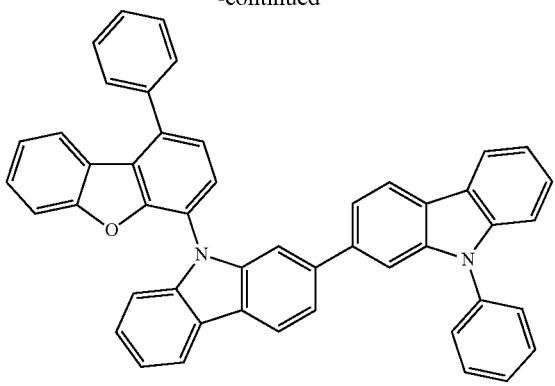

1

Compound B1 (10.0 g, 14.3 mmol) and (9-phenyl-9H-carbazol-2-yl)boronic acid (4.1 g, 14.3 mmol) were dissolved in tetrahydrofuran (150 mL). A 1.5 M aqueous calcium carbonate solution (70 mL) and bis(tri-t-butylphosphine)-palladium(0) (0.07 g, 0.1 mmol) were introduced thereto, and the result was refluxed for 4 hours. After the reaction was finished, the result was cooled to room temperature, and filtered. The filtered material was dissolved in chloroform, washed with water, the water layer was separated and removed, and the result was dried using anhydrous magnesium sulfate, and then vacuum concentrated. After that, the result was recrystallized using a mixed solution of tetrahydrofuran and ethyl acetate. Produced solids were filtered and then dried to prepare Compound 1 (6.3 g, 67%, MS: $[M+H]^+=651$).

Compounds 2 to 51 were prepared using the preparation method of Example 1. Structures, forms, yields and MS thereof are summarized in the following Table 1.

TABLE 1

| Example X | Intermediate 1 | Intermediate 2 | Compound (X) | Form | Yield (%) | MS [M + H]+ |
|---|---|---|---|---|---|---|
| Example 2 | B1 | (9-phenyl-9H-carbazol-2-yl)boronic acid | | Ivory Color | 69 | 651 |
| Example 3 | B1 | (9-phenyl-9H-carbazol-4-yl)boronic acid | | Ivory Color | 63 | 651 |

TABLE 1-continued

| Example X | Intermediate 1 | Intermediate 2 | Compound (X) | Form | Yield (%) | MS [M + H]+ |
|---|---|---|---|---|---|---|
| Example 4 | B1 | | | Ivory Color | 57 | 651 |
| Example 5 | B1 | | | Ivory Color | 70 | 751 |

TABLE 1-continued

| Example X | Intermediate 1 | Intermediate 2 | Compound (X) | Form | Yield (%) | MS [M + H]+ |
|---|---|---|---|---|---|---|
| Example 6 | B1 | | | Ivory Color | 66 | 727 |
| Example 7 | B4 | | | Ivory Color | 65 | 727 |

TABLE 1-continued

| Example X | Intermediate 1 | Intermediate 2 | Compound (X) | Form | Yield (%) | MS [M + H]+ |
|---|---|---|---|---|---|---|
| Example 8 | B4 | (boronic acid intermediate) | (compound structure) | Ivory Color | 59 | 727 |
| Example 9 | B7 | (boronic acid intermediate) | (compound structure) | Ivory Color | 73 | 727 |

TABLE 1-continued
| Example X | Intermediate 1 | Intermediate 2 | Compound (X) | Form | Yield (%) | MS [M + H]+ |
|---|---|---|---|---|---|---|
| Example 10 | B10 | 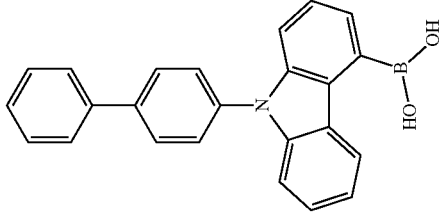 | 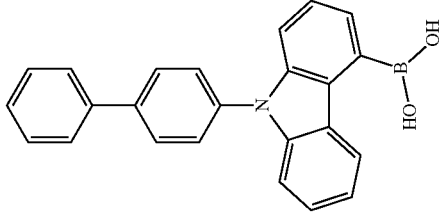 | Ivory Color | 65 | 803 |
| Example 11 | B10 | 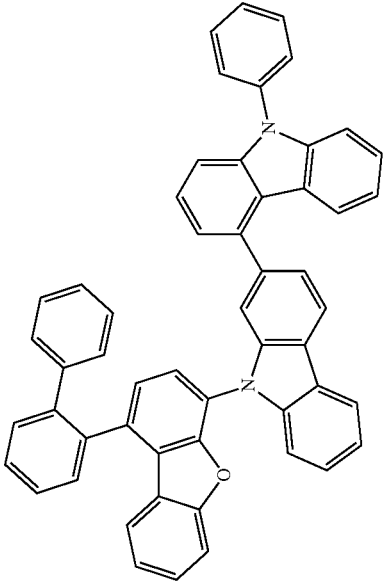 | 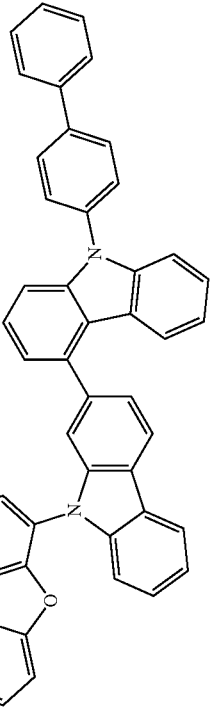 | Ivory Color | 60 | 727 |

TABLE 1-continued

| Example X | Intermediate 1 | Intermediate 2 | Compound (X) | Form | Yield (%) | MS [M + H]$^+$ |
|---|---|---|---|---|---|---|
| Example 12 | B2 | (structure) | (structure) | Ivory Color | 66 | 651 |
| Example 13 | B2 | (structure) | (structure) | Ivory Color | 65 | 651 |

TABLE 1-continued
| Example X | Intermediate 1 | Intermediate 2 | Compound (X) | Form | Yield (%) | MS [M + H]⁺ |
|---|---|---|---|---|---|---|
| Example 14 | B2 | 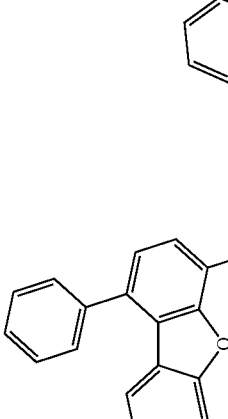 | 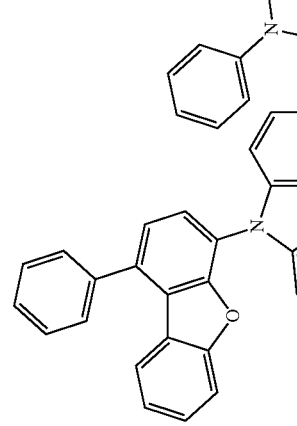 | Ivory Color | 65 | 651 |
| Example 15 | B2 | 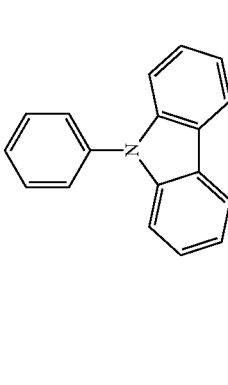 | 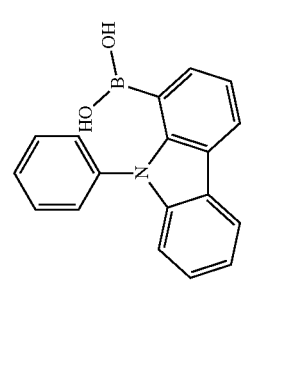 | Ivory Color | 60 | 651 |

TABLE 1-continued

| Example X | Intermediate 1 | Intermediate 2 | Compound (X) | Form | Yield (%) | MS [M + H]+ |
|---|---|---|---|---|---|---|
| Example 16 | B2 | (structure) | (structure) | Ivory Color | 64 | 701 |
| Example 17 | B2 | (structure) | (structure) | Ivory Color | 62 | 767 |

TABLE 1-continued
| Example X | Intermediate 1 | Intermediate 2 | Compound (X) | Form | Yield (%) | MS [M + H]+ |
|---|---|---|---|---|---|---|
| Example 18 | B2 | 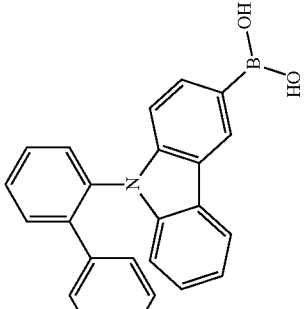 | 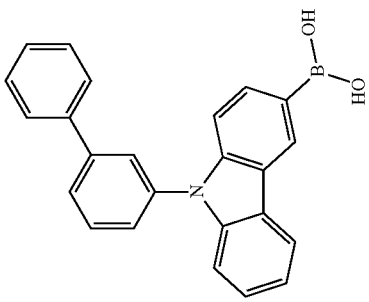 | Ivory Color | 63 | 727 |
| Example 19 | B2 | 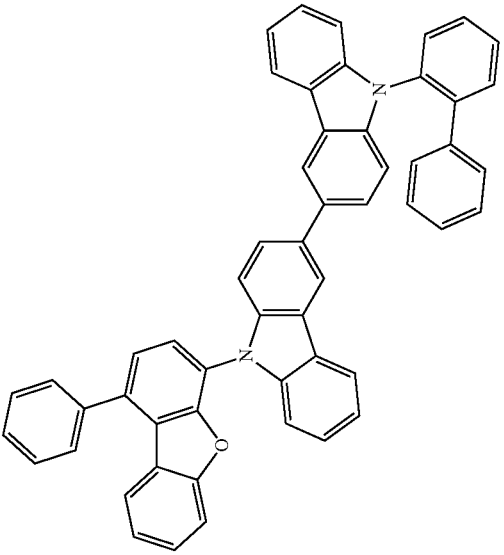 | 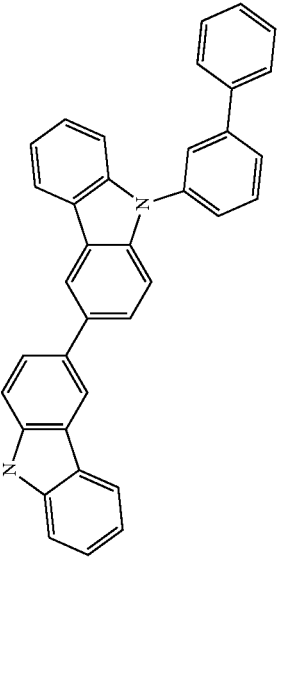 | Ivory Color | 59 | 727 |

TABLE 1-continued

| Example X | Intermediate 1 | Intermediate 2 | Compound (X) | Form | Yield (%) | MS [M + H]+ |
|---|---|---|---|---|---|---|
| Example 20 | B2 | | | Ivory Color | 58 | 727 |
| Example 21 | B2 | | | Ivory Color | 62 | 727 |

TABLE 1-continued

| Example X | Intermediate 1 | Intermediate 2 | Compound (X) | Form | Yield (%) | MS [M + H]+ |
|---|---|---|---|---|---|---|
| Example 22 | B2 | | | Ivory Color | 67 | 727 |
| Example 23 | B2 | | | Ivory Color | 65 | 727 |

TABLE 1-continued

| Example X | Intermediate 1 | Intermediate 2 | Compound (X) | Form | Yield (%) | MS [M + H]+ |
|---|---|---|---|---|---|---|
| Example 24 | B8 | | | Ivory Color | 68 | 727 |

TABLE 1-continued
| Example X | Intermediate 1 | Intermediate 2 | Compound (X) | Form | Yield (%) | MS [M + H]+ |
|---|---|---|---|---|---|---|
| Example 25 | B5 | 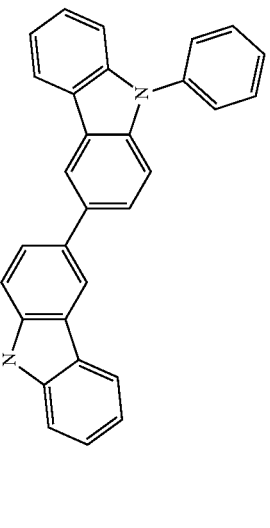 | | Ivory Color | 65 | 727 |

TABLE 1-continued

| Example X | Intermediate 1 | Intermediate 2 | Compound (X) | Form | Yield (%) | MS [M + H]$^+$ |
|---|---|---|---|---|---|---|
| Example 26 | B11 | | | Ivory Color | 61 | 727 |
| Example 27 | B3 | | | Ivory Color | 60 | 727 |

TABLE 1-continued

| Example X | Intermediate 1 | Intermediate 2 | Compound (X) | Form | Yield (%) | MS [M + H]+ |
|---|---|---|---|---|---|---|
| Example 28 | B3 | | | Ivory Color | 65 | 651 |
| Example 29 | B3 | | | Ivory Color | 63 | 651 |
| Example 30 | B3 | | | Ivory Color | 63 | 651 |

TABLE 1-continued

| Example X | Intermediate 1 | Intermediate 2 | Compound (X) | Form | Yield (%) | MS [M + H]+ |
|---|---|---|---|---|---|---|
| Example 31 | B3 | | | Ivory Color | 61 | 651 |
| Example 32 | B3 | | | Ivory Color | 65 | 701 |

TABLE 1-continued

| Example X | Intermediate 1 | Intermediate 2 | Compound (X) | Form | Yield (%) | MS [M + H]+ |
|---|---|---|---|---|---|---|
| Example 33 | B3 | | | Ivory Color | 70 | 801 |
| Example 34 | B3 | | | Ivory Color | 64 | 727 |

TABLE 1-continued

| Example X | Intermediate 1 | Intermediate 2 | Compound (X) | Form | Yield (%) | MS [M + H]+ |
|---|---|---|---|---|---|---|
| Example 35 | B12 | | | Ivory Color | 59 | 727 |
| Example 36 | B6 | | | Ivory Color | 64 | 727 |

TABLE 1-continued
| Example X | Intermediate 1 | Intermediate 2 | Compound (X) | Form | Yield (%) | MS [M + H]+ |
|---|---|---|---|---|---|---|
| Example 37 | B9 | 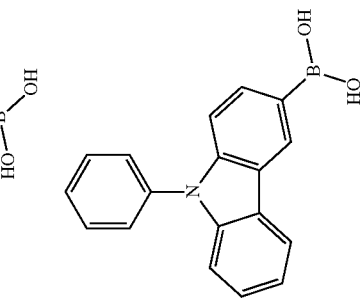 | 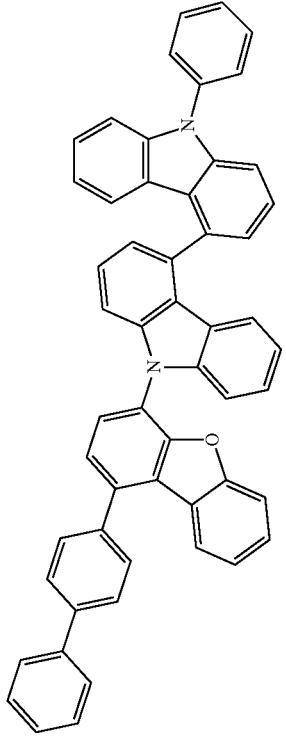 | Ivory Color | 67 | 727 |
| Example 38 | B12 | 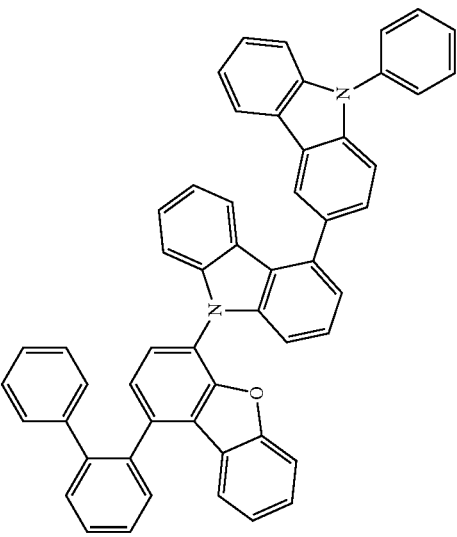 | 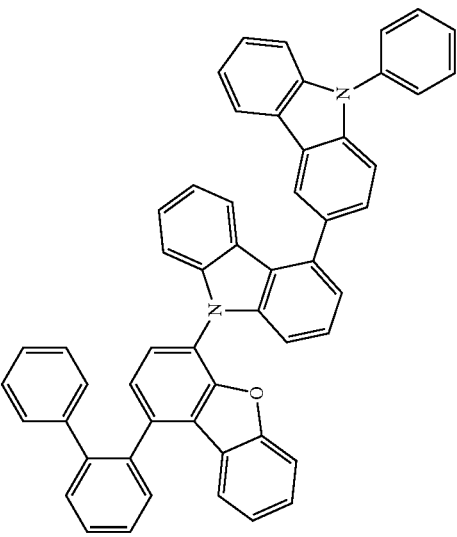 | Ivory Color | 60 | 727 |

TABLE 1-continued
| Example X | Intermediate 1 | Intermediate 2 | Compound (X) | Form | Yield (%) | MS [M + H]+ |
|---|---|---|---|---|---|---|
| Example 39 | B13 | 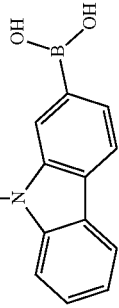 | 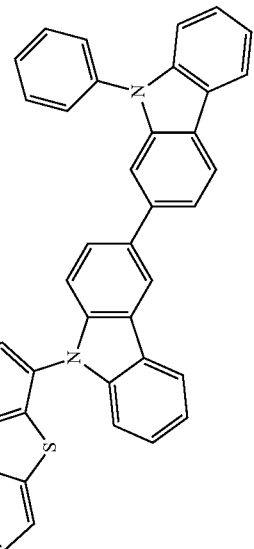 | Ivory Color | 69 | 667 |
| Example 40 | B13 | 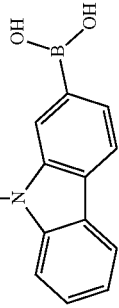 | 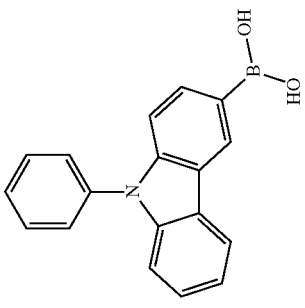 | Ivory Color | 71 | 667 |

TABLE 1-continued

| Example X | Intermediate 1 | Intermediate 2 | Compound (X) | Form | Yield (%) | MS [M + H]+ |
|---|---|---|---|---|---|---|
| Example 41 | B13 | | | Ivory Color | 68 | 667 |
| Example 42 | B13 | | | Ivory Color | 63 | 667 |

TABLE 1-continued
| Example X | Intermediate 1 | Intermediate 2 | Compound (X) | Form | Yield (%) | MS [M + H]+ |
|---|---|---|---|---|---|---|
| Example 43 | B13 | 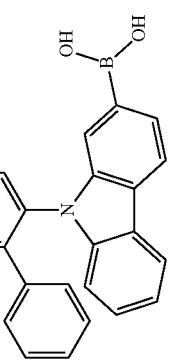 | 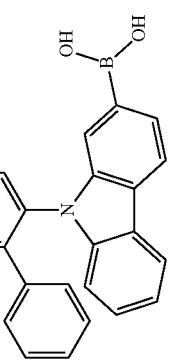 | Ivory Color | 62 | 743 |
| Example 44 | B13 | 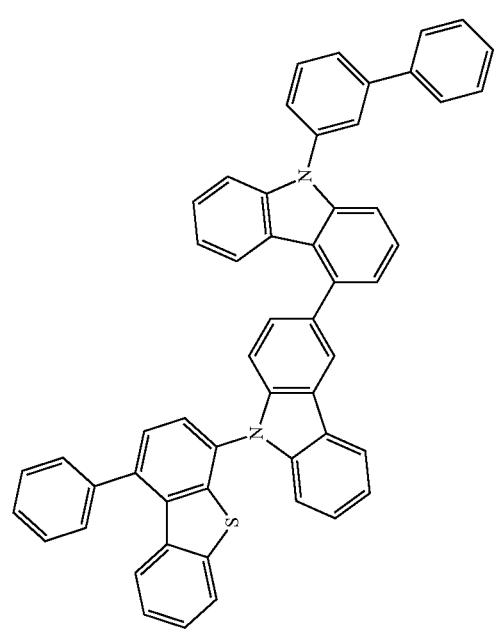 | 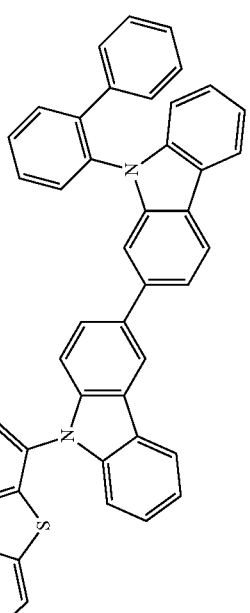 | Ivory Color | 67 | 743 |

TABLE 1-continued

| Example X | Intermediate 1 | Intermediate 2 | Compound (X) | Form | Yield (%) | MS [M + H]+ |
|---|---|---|---|---|---|---|
| Example 45 | B13 | | | Ivory Color | 66 | 743 |
| Example 46 | B14 | | | Ivory Color | 66 | 743 |

TABLE 1-continued

| Example X | Intermediate 1 | Intermediate 2 | Compound (X) | Form | Yield (%) | MS [M + H]+ |
|---|---|---|---|---|---|---|
| Example 47 | B14 | | | Ivory Color | 68 | 743 |

TABLE 1-continued

| Example X | Intermediate 1 | Intermediate 2 | Compound (X) | Form | Yield (%) | MS [M + H]⁺ |
|---|---|---|---|---|---|---|
| Example 48 | B15 | | | Ivory Color | 71 | 743 |

TABLE 1-continued

| Example X | Intermediate 1 | Intermediate 2 | Compound (X) | Form | Yield (%) | MS [M + H]+ |
|---|---|---|---|---|---|---|
| Example 49 | B16 | | | Ivory Color | 63 | 743 |
| Example 50 | B16 | | | Ivory Color | 62 | 743 |

TABLE 1-continued

| Example X | Intermediate 1 | Intermediate 2 | Compound (X) | Form | Yield (%) | MS [M + H]+ |
|---|---|---|---|---|---|---|
| Example 51 | B2 | | | Ivory Color | 66 | 656 |

EXPERIMENTAL EXAMPLE

Experimental Example 1

A glass substrate on which indium tin oxide (ITO) was coated as a thin film to a thickness of 1,300 Å was placed in distilled water containing dissolved detergent and ultrasonically cleaned. A product of Fischer Co. was used as the detergent, and as the distilled water, distilled water filtered twice with a filter manufactured by Millipore Co. was used. After the ITO was cleaned for 30 minutes, ultrasonic cleaning was repeated twice using distilled water for 10 minutes. After the cleaning with distilled water was finished, the substrate was ultrasonically cleaned with solvents of isopropyl alcohol, acetone and methanol, then dried, and then transferred to a plasma cleaner. The substrate was cleaned for 5 minutes using oxygen plasma, and then transferred to a vacuum depositor.

On the transparent ITO electrode prepared as above, a hole injection layer was formed by thermal vacuum depositing the following compound HI-A to a thickness of 100 Å. Subsequently, only a HT-A material was thermal vacuum deposited to a thickness of 800 Å to form a hole transfer layer, and a compound HT-B was consecutively vacuum deposited to a thickness of 500 Å to form an electron blocking layer. Then, as a light emitting layer, compound H1 as a first host and Compound 1 as a second host in a weight ratio of 50:50 and 6% by weight of GD with respect to a sum of the weight of the two hosts were vacuum deposited to a thickness of 350 Å. Subsequently, the following compound ET-A was vacuum deposited to a thickness of 50 Å as a hole blocking layer. Then, the following compounds ET-B and Liq in a ratio of 1:1 were thermal vacuum deposited to a thickness of 250 Å as an electron transfer layer, and then LiF was vacuum deposited to a thickness of 30 Å as an electron injection layer. Subsequently, aluminum was deposited to a thickness of 1000 Å to form a cathode, and as a result, an organic light emitting device was manufactured.

HI-A

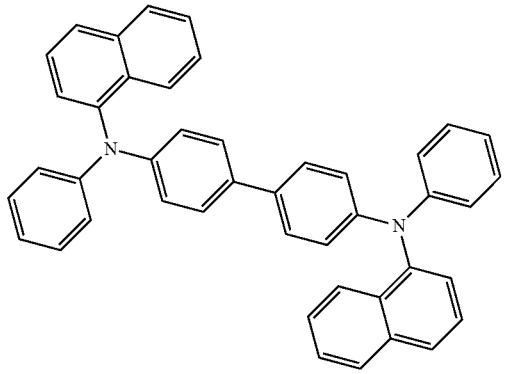

HT-A

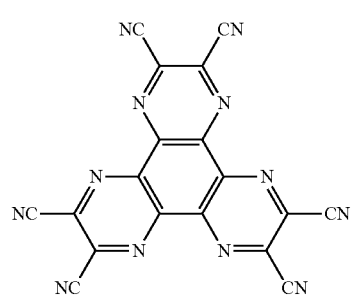

HT-B

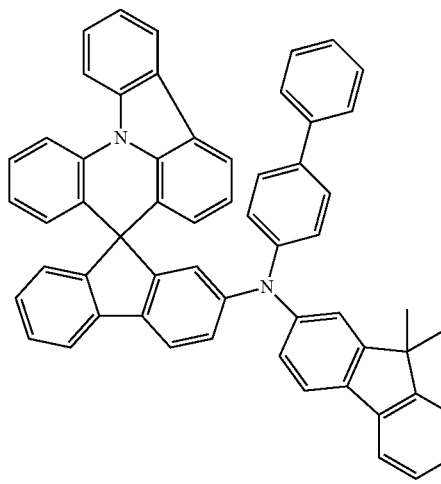

H1

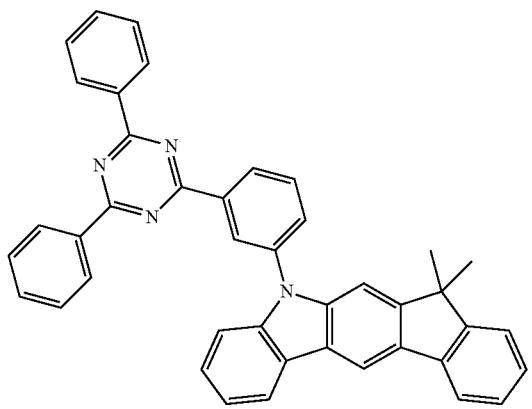

GD

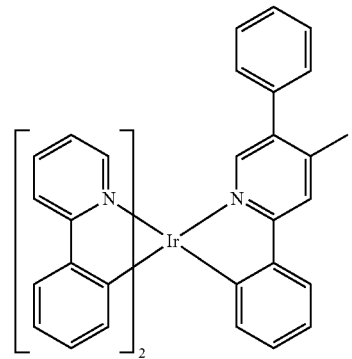

ET-A

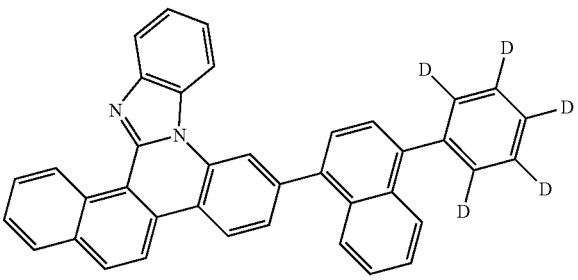

ET-B

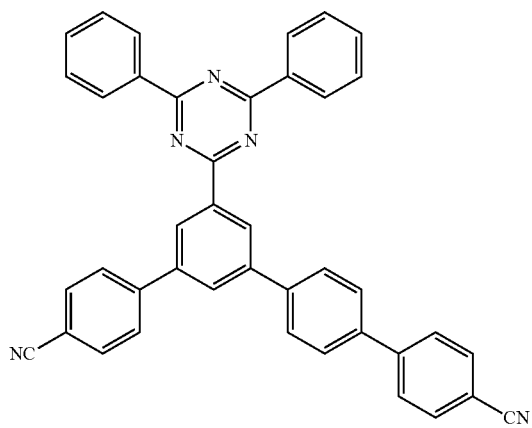

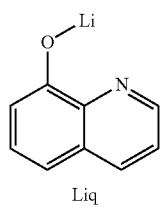

Liq

Experimental Example 2 to Experimental Example 20 and Comparative Example 1 to Comparative Example 4

Organic light emitting devices of Experimental Example 2 to Experimental Example 20 and Comparative Example 1 to Comparative Example 4 were each manufactured in the same manner as in Experimental Example 1 except that each compound specified in the following Table 2 was used instead of Compound 1.

C1

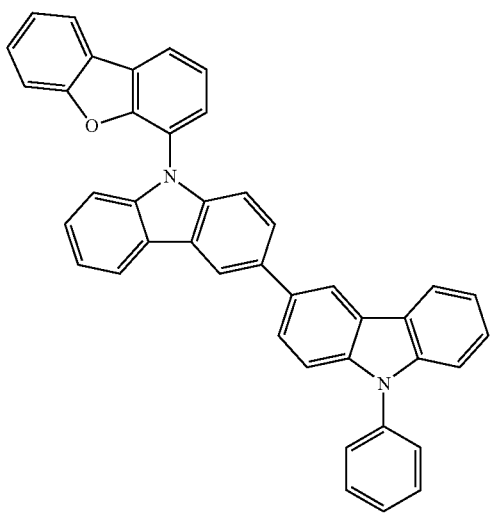

C2

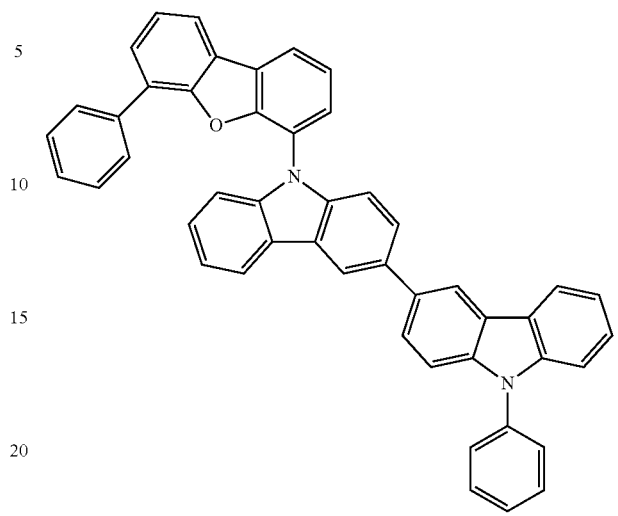

C3

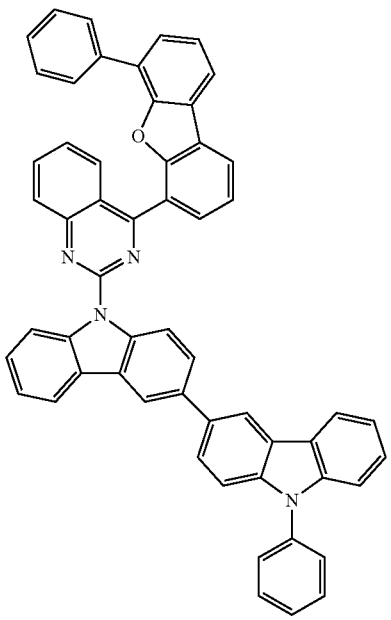

C4

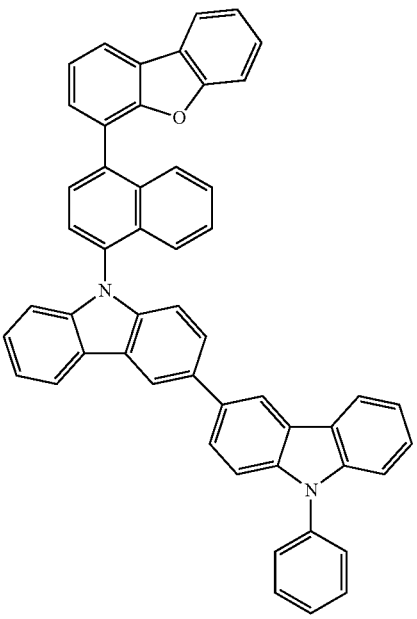

A voltage, efficiency and a lifetime (T95) were measured by applying a current to each of the organic light emitting devices manufactured in Experimental Example 1 to Experimental Example 20 and Comparative Example 1 to Comparative Example 4, and the results are shown in the following Table 2. Herein, the voltage and the efficiency were measured by applying current density of 10 mA/cm$^2$, and T95 means time taken for initial luminance decreasing to 95% at current density of 50 mA/cm$^2$.

TABLE 2

|  | | @10 mA/cm$^2$ | | @50 mA/cm$^2$ |
|---|---|---|---|---|
|  | Second Host Material | Voltage (V) | Efficiency (cd/A) | Lifetime (T95, hr) |
| Experimental Example 1 | Compound 1 | 4.2 | 57.9 | 125 |
| Experimental Example 2 | Compound 5 | 4.3 | 58.2 | 135 |
| Experimental Example 3 | Compound 7 | 4.2 | 58.0 | 130 |
| Experimental Example 4 | Compound 9 | 4.2 | 58.9 | 140 |
| Experimental Example 5 | Compound 13 | 4.0 | 59.3 | 150 |
| Experimental Example 6 | Compound 14 | 4.1 | 58.6 | 145 |
| Experimental Example 7 | Compound 15 | 4.0 | 57.9 | 135 |
| Experimental Example 8 | Compound 16 | 4.2 | 57.2 | 125 |
| Experimental Example 9 | Compound 17 | 4.1 | 58.9 | 135 |
| Experimental Example 10 | Compound 23 | 4.0 | 59.0 | 145 |
| Experimental Example 11 | Compound 26 | 4.0 | 58.4 | 150 |
| Experimental Example 12 | Compound 30 | 4.1 | 57.2 | 125 |
| Experimental Example 13 | Compound 33 | 4.1 | 57.0 | 130 |
| Experimental Example 14 | Compound 34 | 4.2 | 57.9 | 135 |
| Experimental Example 15 | Compound 38 | 4.1 | 57.1 | 130 |

TABLE 2-continued

|  | | @10 mA/cm$^2$ | | @50 mA/cm$^2$ |
|---|---|---|---|---|
|  | Second Host Material | Voltage (V) | Efficiency (cd/A) | Lifetime (T95, hr) |
| Experimental Example 16 | Compound 40 | 3.9 | 56.3 | 135 |
| Experimental Example 17 | Compound 44 | 3.9 | 56.0 | 140 |
| Experimental Example 18 | Compound 45 | 3.8 | 55.9 | 140 |
| Experimental Example 19 | Compound 47 | 3.9 | 56.4 | 140 |
| Experimental Example 20 | Compound 51 | 4.0 | 59.0 | 165 |
| Comparative Example 1 | Compound C1 | 4.5 | 53.2 | 100 |
| Comparative Example 2 | Compound C2 | 4.3 | 45.0 | 120 |
| Comparative Example 3 | Compound C3 | 5.4 | 30.1 | 25 |
| Comparative Example 4 | Compound C4 | 5.0 | 36.6 | 80 |

As shown in Table 2, it was seen that properties of low voltage, high efficiency and long lifetime were obtained when using the compound of Chemical Formula 1 according to the present disclosure as a host of a light emitting layer.

Particularly, it was identified that device properties were different depending on Ar2 of Chemical Formula 1. Specifically, Experimental Examples 5 and 19 using Compounds 13 and 47 in which Ar2 is a phenyl group or a biphenyl group exhibited properties of low voltage and long lifetime when compared to Comparative Examples 1 and 4 using the compounds (C1 and C4) in which Ar2 is hydrogen. When comparing the position of the Ar2 substituent, it was identified that the experimental examples using the compound of Chemical Formula 1 had efficiency enhanced by approximately 30% or greater compared to Comparative Examples 2 and 3 using Compounds C2 and C3. Particularly, from the results of Comparative Examples 1 to 4 using Compounds C3 and C4 in which L includes a linker instead of being a direct bond and Compounds C1 and C2 in which L is a direct bond, it was identified that the compound in which L is a direct bond was effective in obtaining a long lifetime.

The invention claimed is:

1. A compound of Chemical Formula 1:

Chemical Formula 1

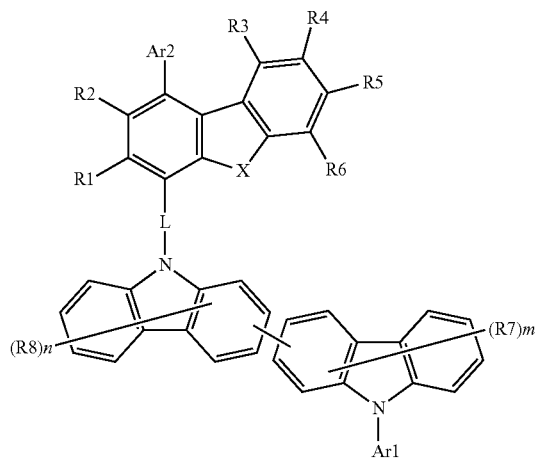

wherein, in Chemical Formula 1:
X is O or S;
L is a direct bond;
Ar1 is a substituted or unsubstituted aryl group or a substituted or unsubstituted heteroaryl group;
Ar2 is a substituted or unsubstituted aryl group having 6 to 30 carbon atoms;
R1 to R8 are the same as or different from each other, and each independently is hydrogen, a substituted or unsubstituted aryl group, or a substituted or unsubstituted heteroaryl group; and
m and n are each an integer of 0 to 7, and when m is 2 or greater, the R7s are the same as or different from each other, and when n is 2 or greater, the R8s are the same as or different from each other.

2. The compound of claim 1, wherein Chemical Formula 1 is any one of the following Chemical Formulae 4 to 7:

Chemical Formula 4

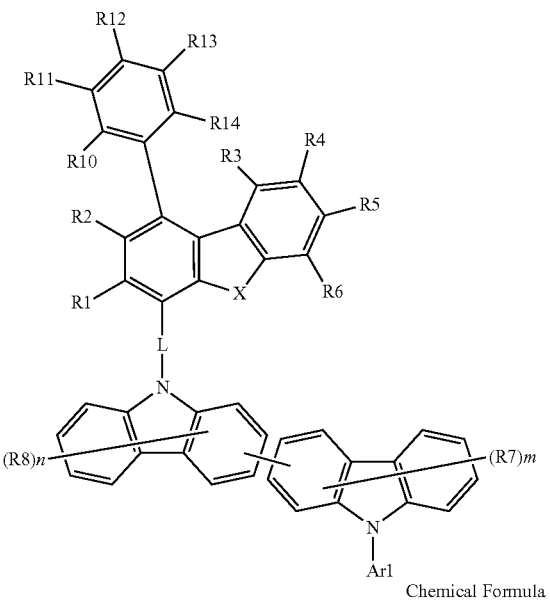

Chemical Formula 5

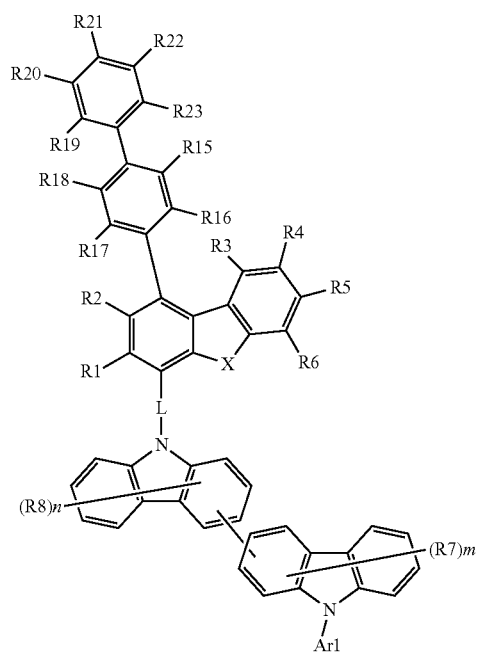

Chemical Formula 6

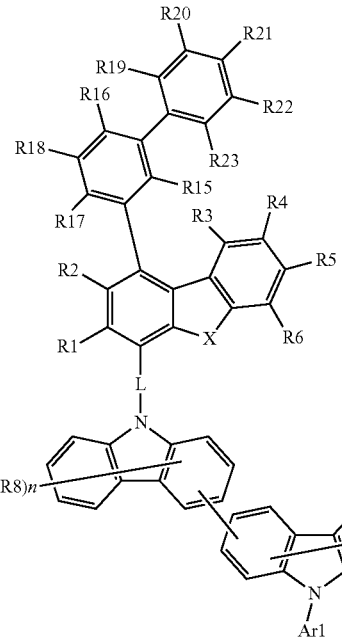

Chemical Formula 7

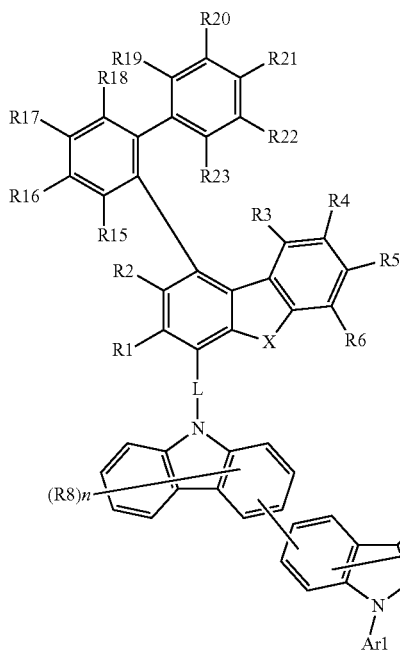

wherein in Chemical Formulae 4 to 7:
Ar1, X, L, m, n and R1 to R8 have the same definitions as in Chemical Formula 1; and
R10 to R23 are the same as or different from each other, and each independently is hydrogen, deuterium, or a substituted or unsubstituted aryl group.

3. The compound of claim 1, wherein Chemical Formula 1 is any one of the following Chemical Formulae 1-1 to 1-12:

Chemical Formula 1-1
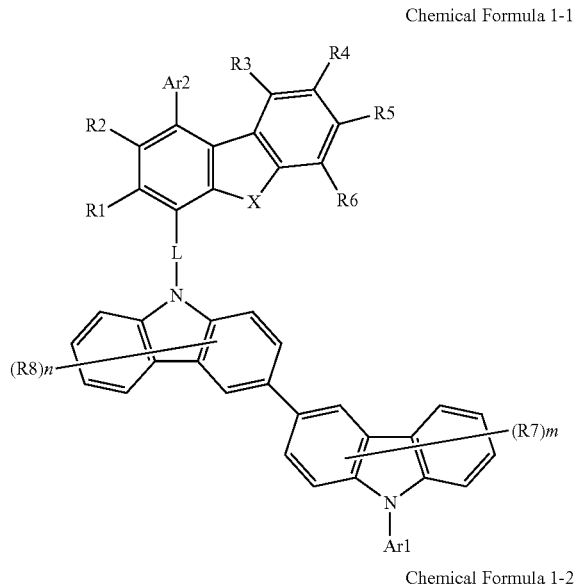
Chemical Formula 1-2
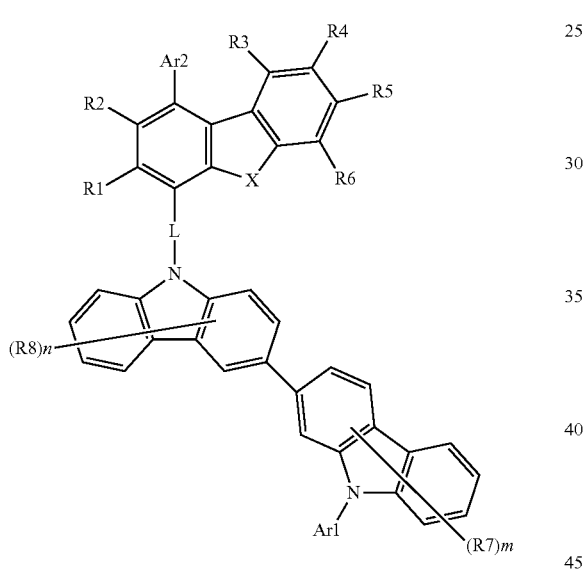
Chemical Formula 1-3
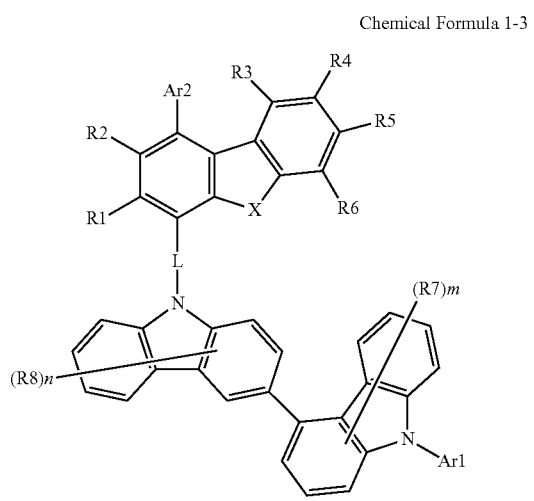
-continued
Chemical Formula 1-4
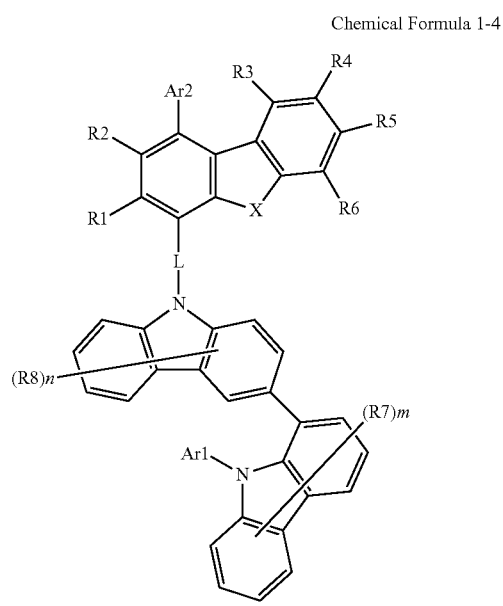
Chemical Formula 1-5
Chemical Formula 1-6
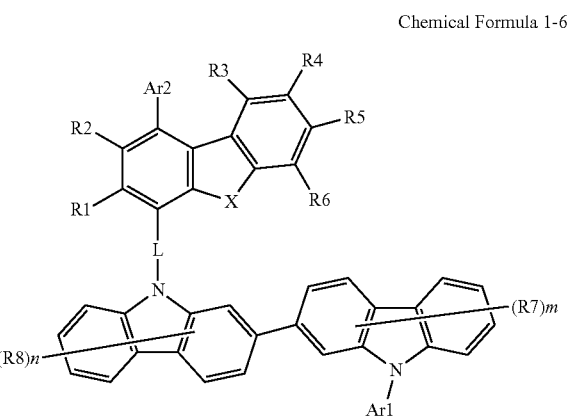

Chemical Formula 1-7
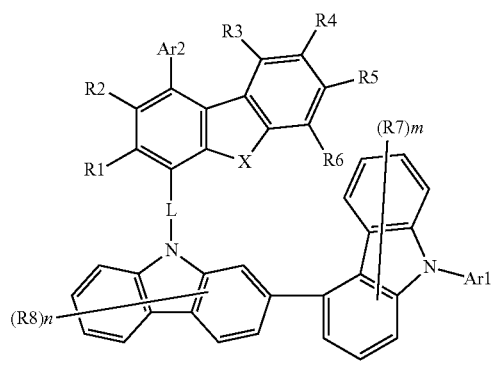
Chemical Formula 1-8
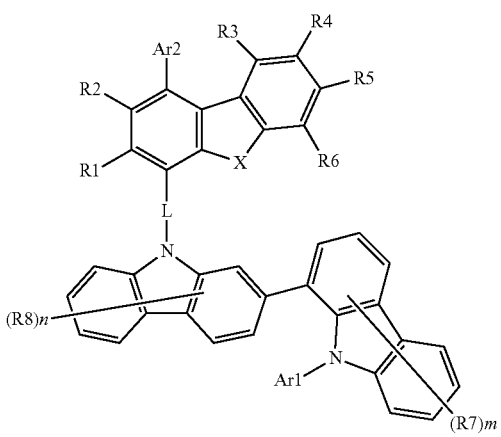
Chemical Formula 1-9
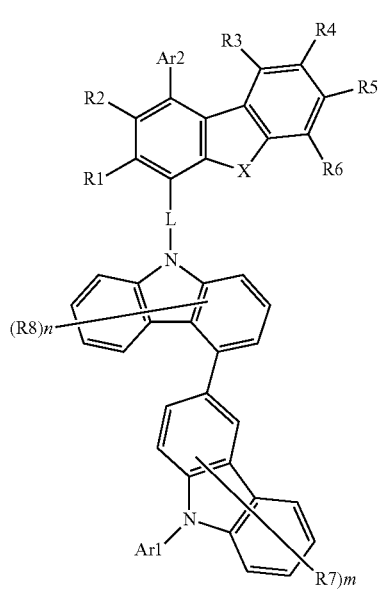
Chemical Formula 1-10
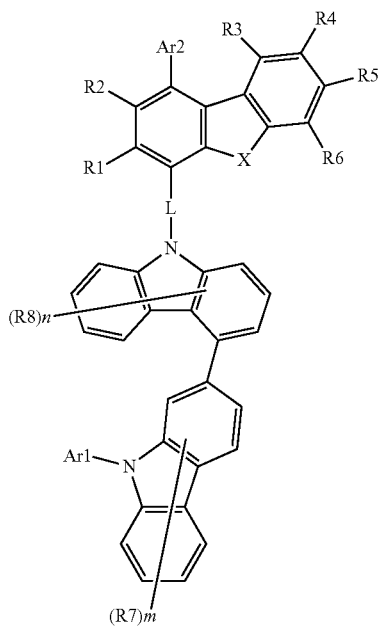
Chemical Formula 1-11
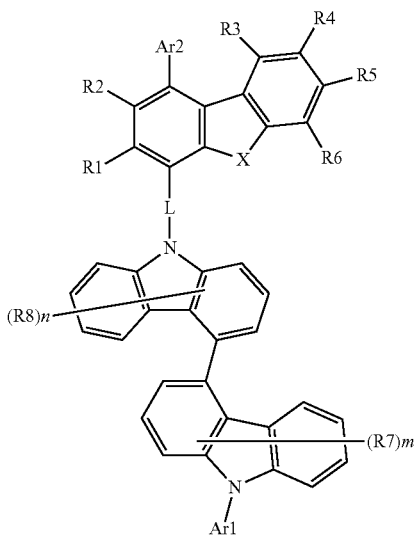

-continued

Chemical Formula 1-12

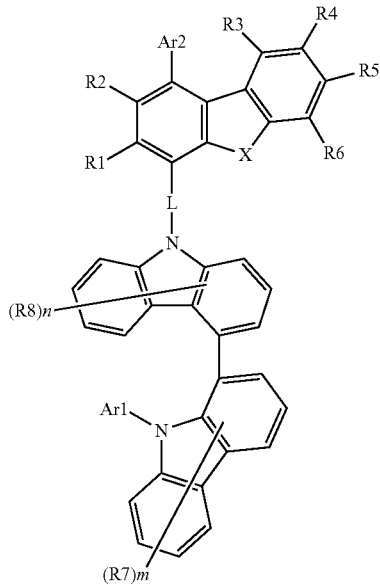

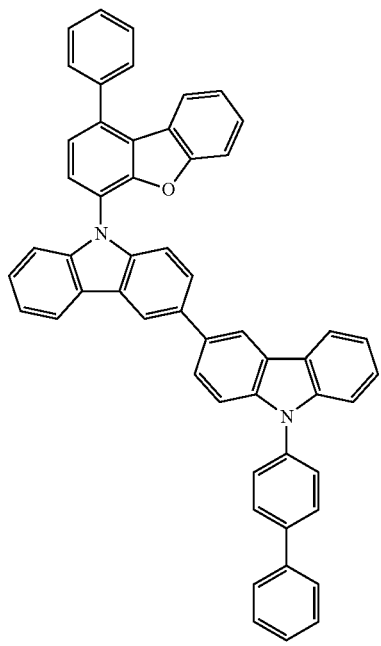

wherein in Chemical Formulae 1-1 to 1-12:
Ar1, Ar2, X, L, m, n and R1 to R8 have the same definitions as in Chemical Formula 1.

4. The compound of claim 1, wherein Ar1 and Ar2 are the same as or different from each other, and each independently is a substituted or unsubstituted phenyl group, a substituted or unsubstituted biphenyl group, a substituted or unsubstituted naphthyl group, a substituted or unsubstituted triphenylene group, a substituted or unsubstituted phenanthrene group, or a substituted or unsubstituted fluorene group.

5. The compound of claim 1, wherein R1 to R6 are hydrogen.

6. The compound of claim 1, wherein the compound of Chemical Formula 1 is any one selected from among the following compounds:

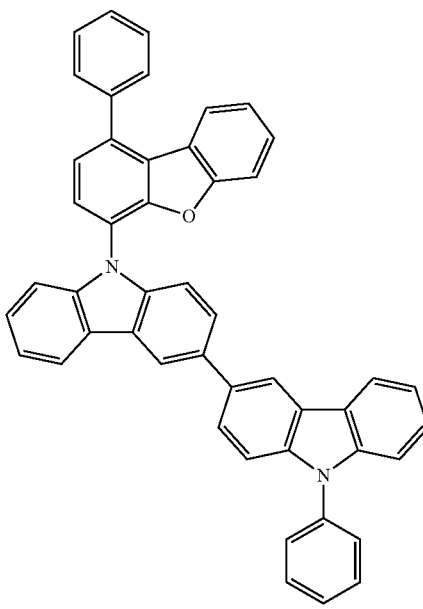

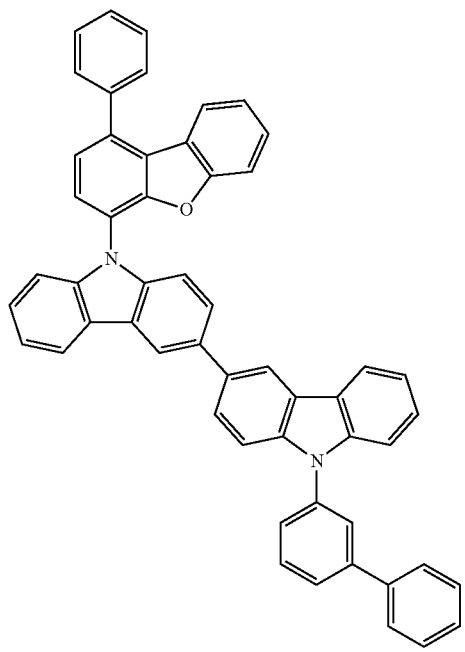

183
-continued
184
-continued
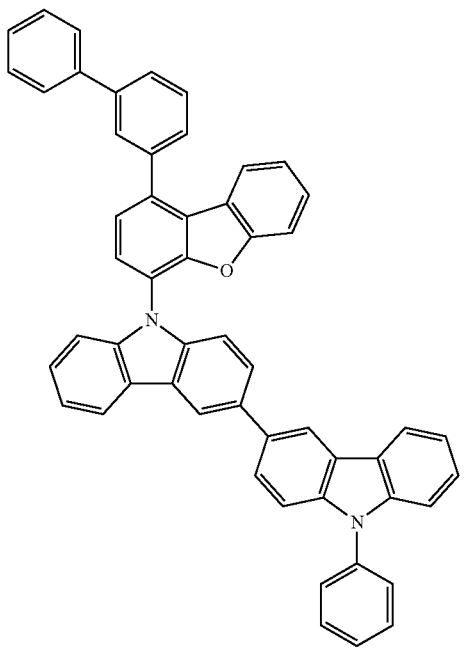
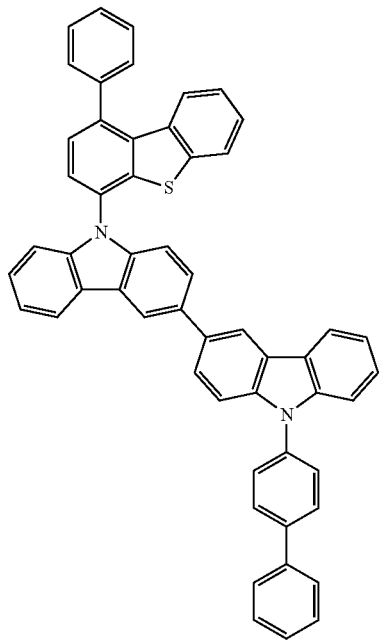
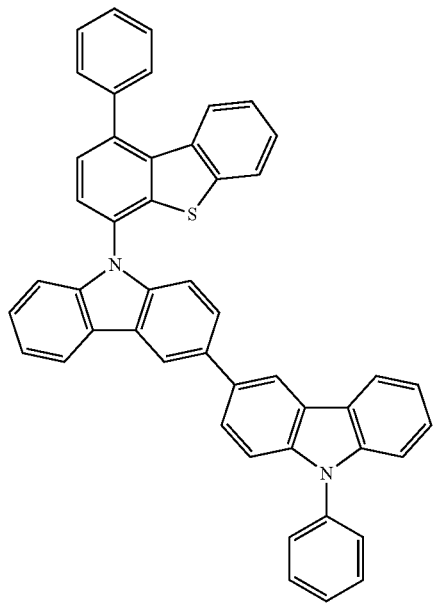

185
-continued
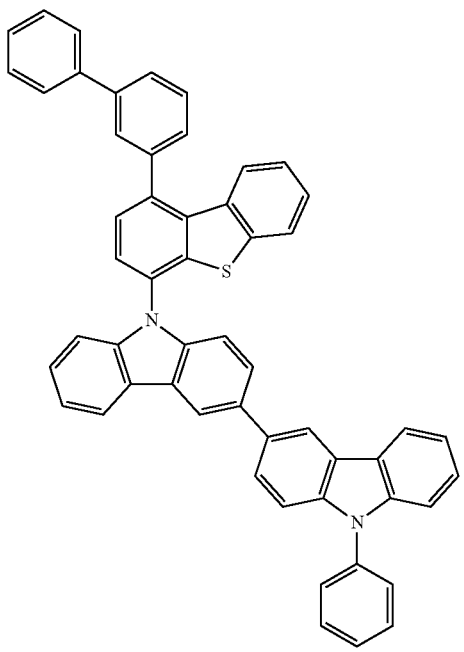
186
-continued
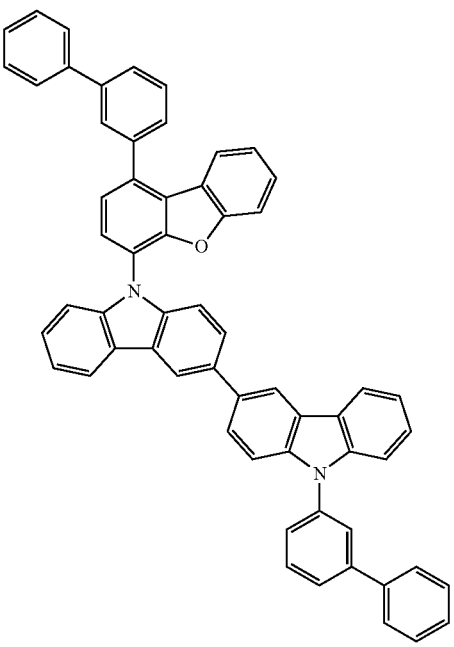
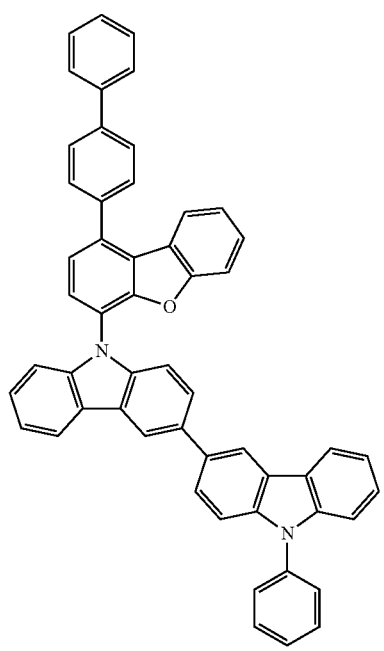
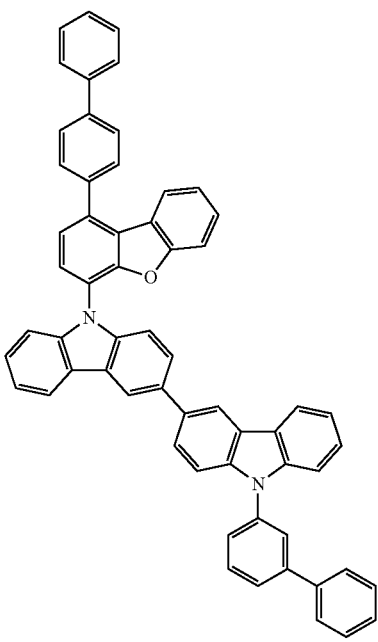

187
-continued
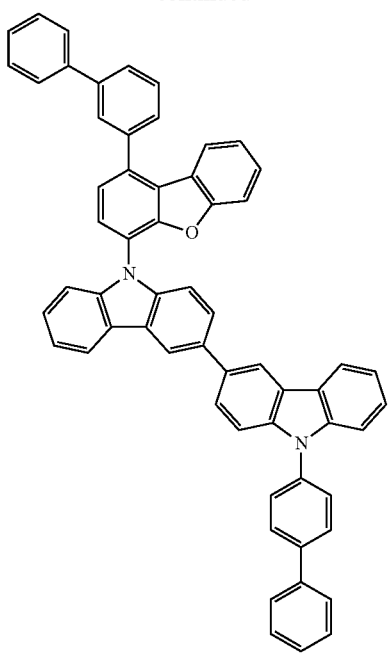
188
-continued
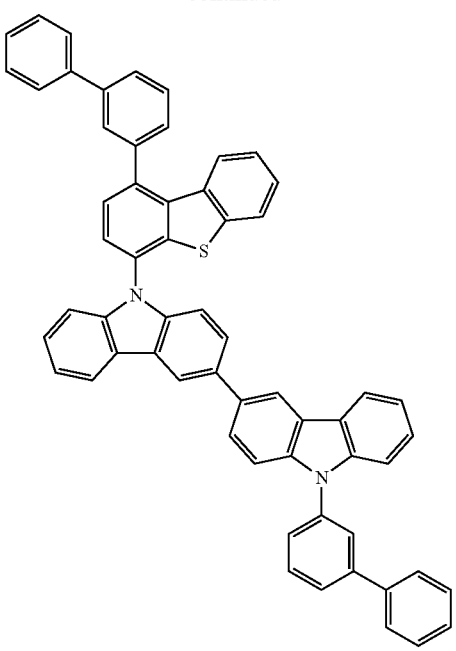
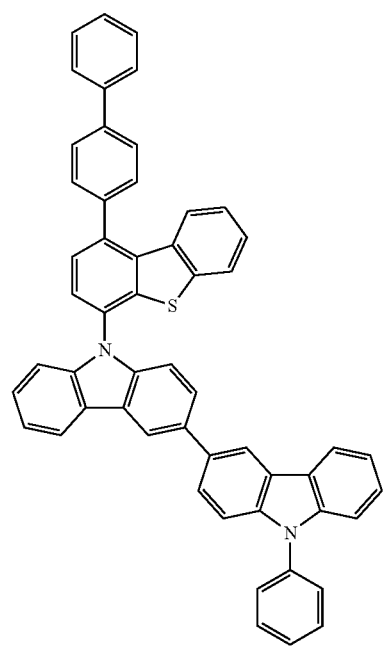
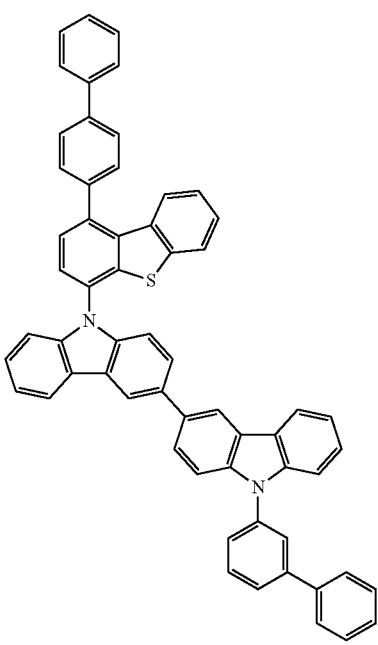

189
-continued
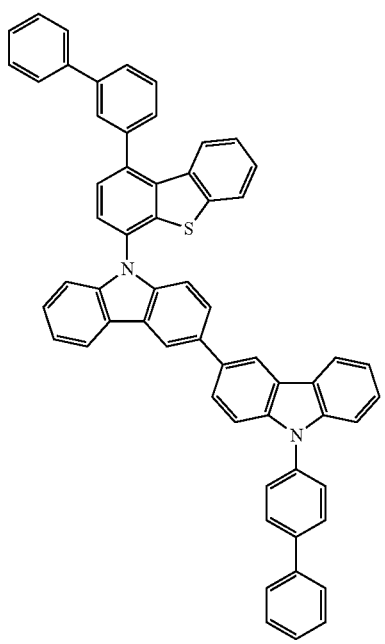
190
-continued
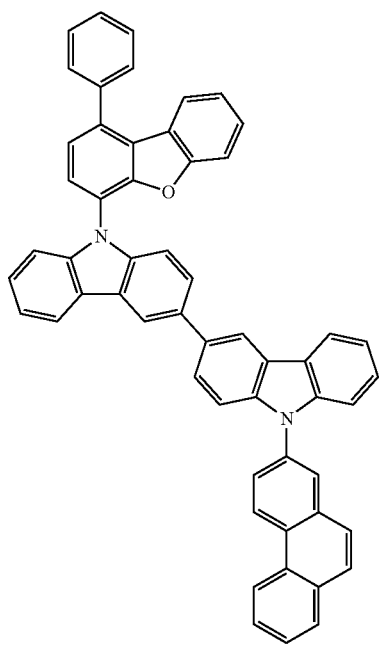
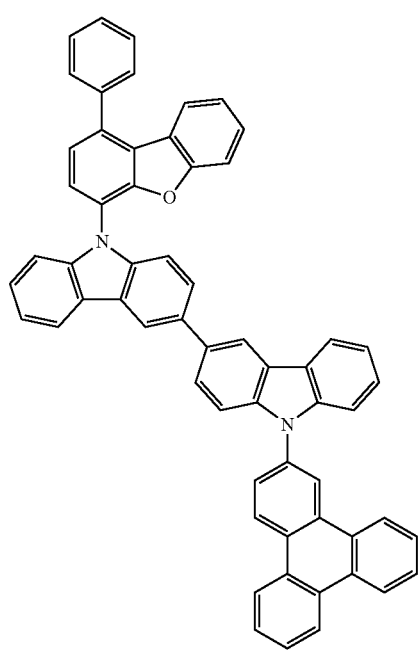
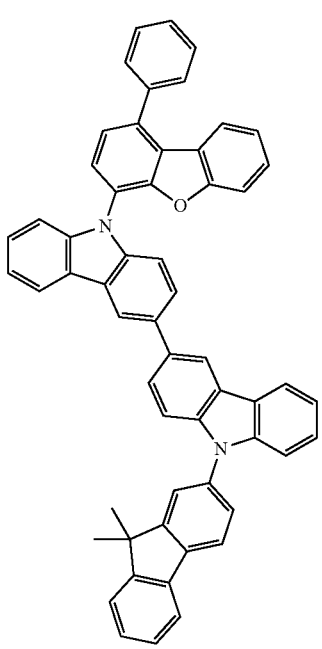

191
-continued
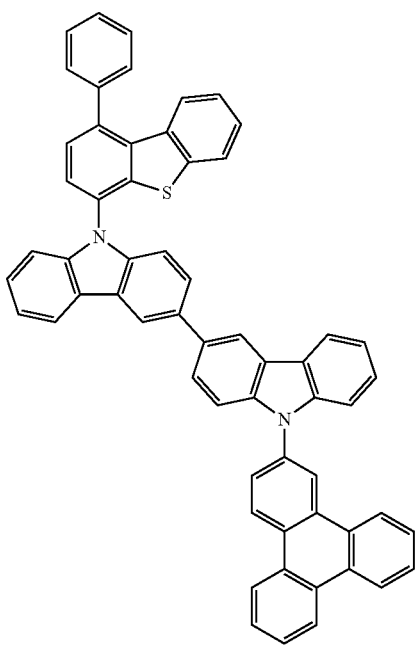
192
-continued
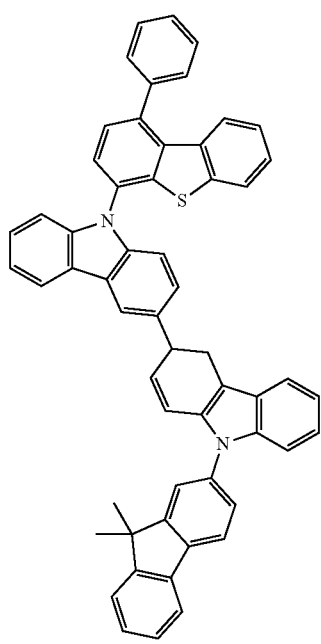
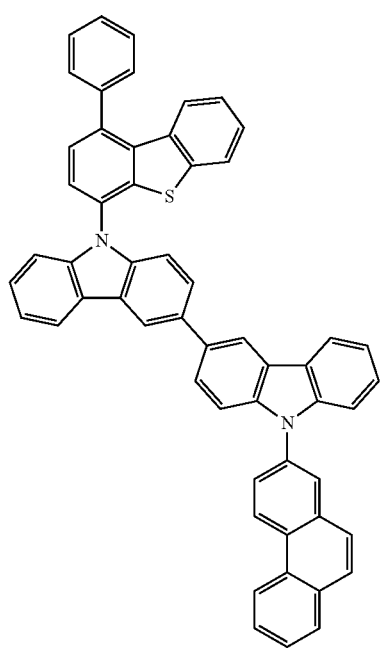
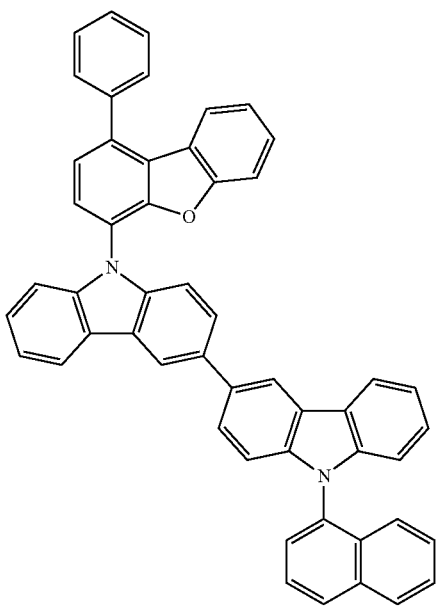

193
-continued
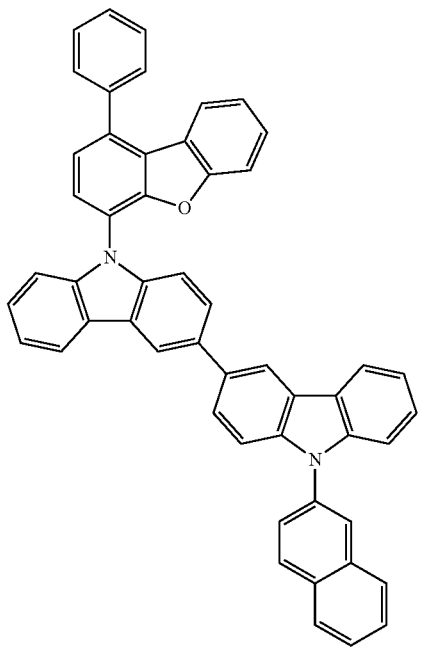
194
-continued
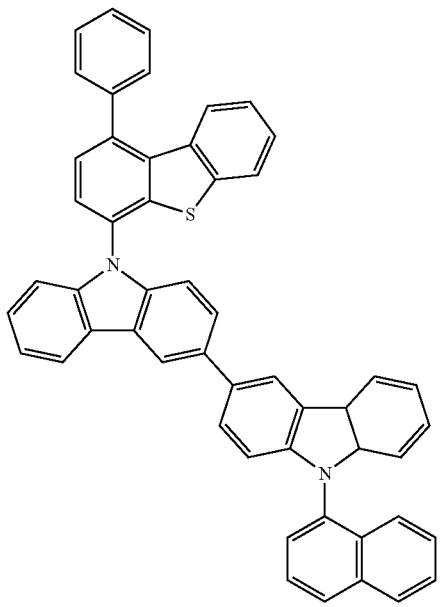
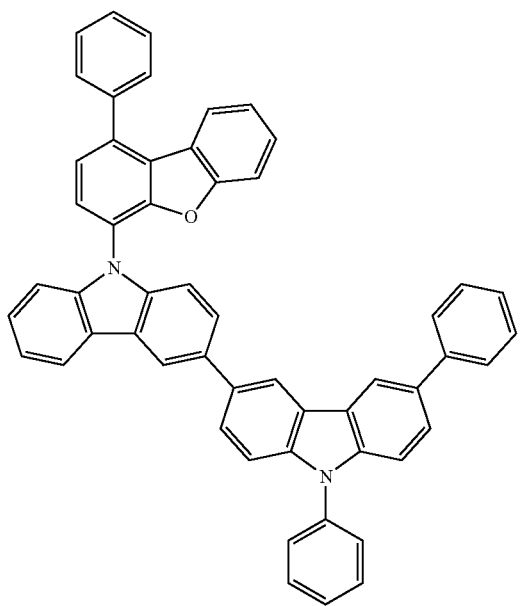
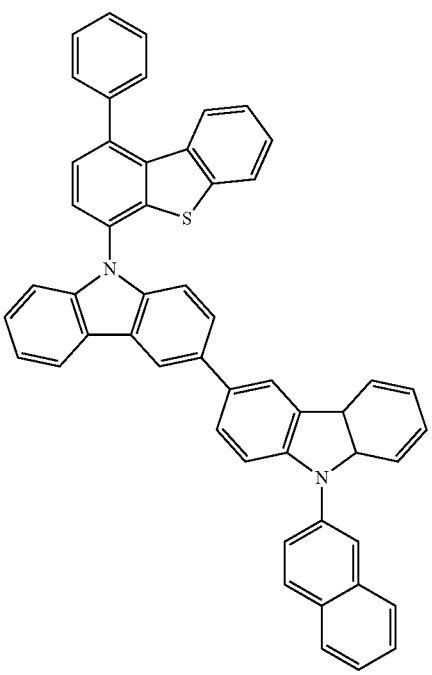

195
-continued
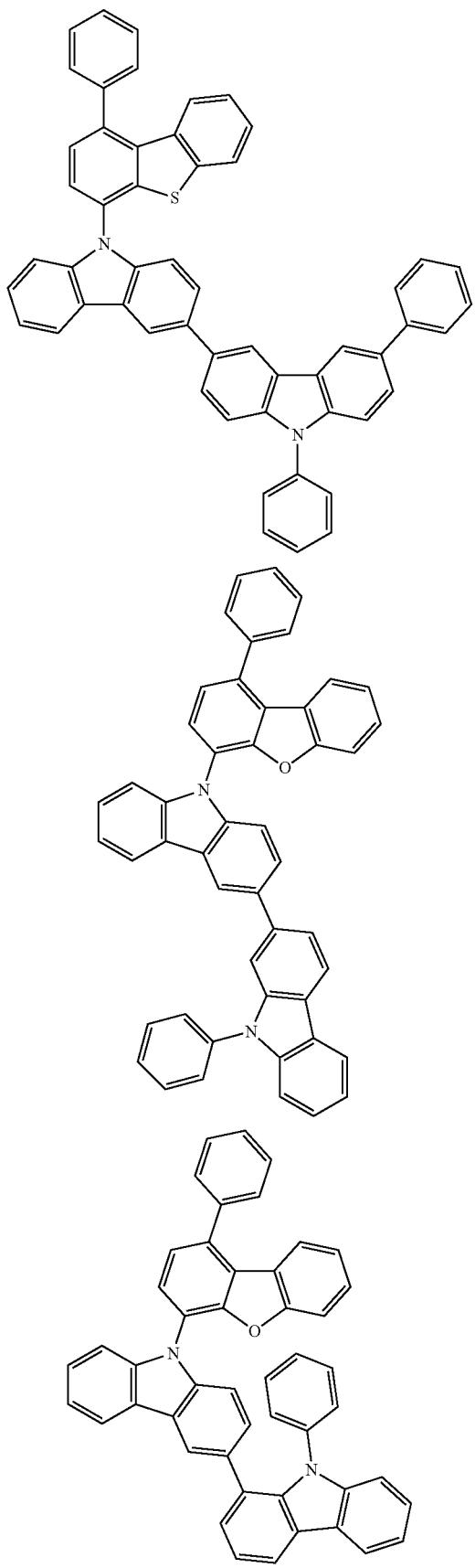
196
-continued
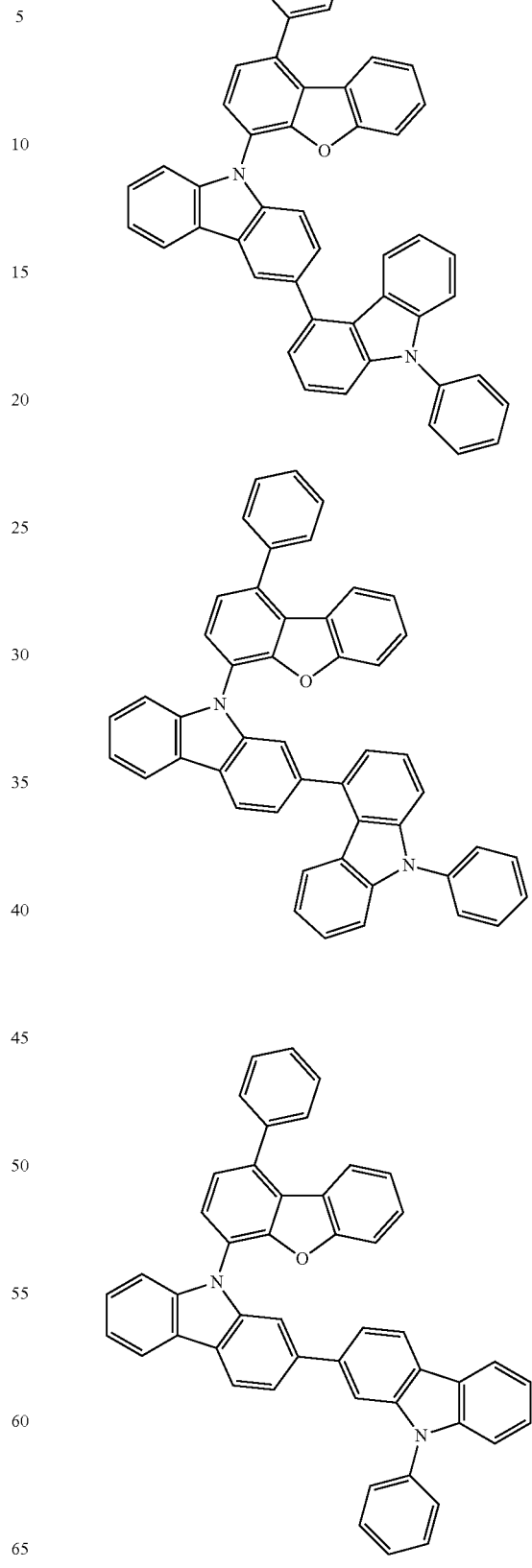

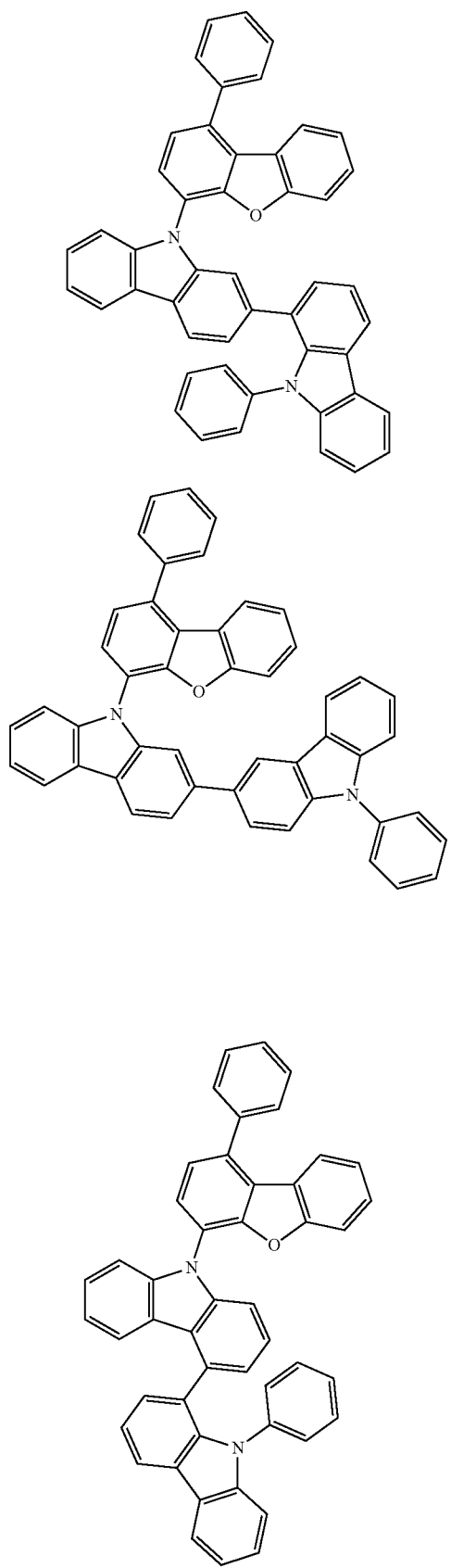
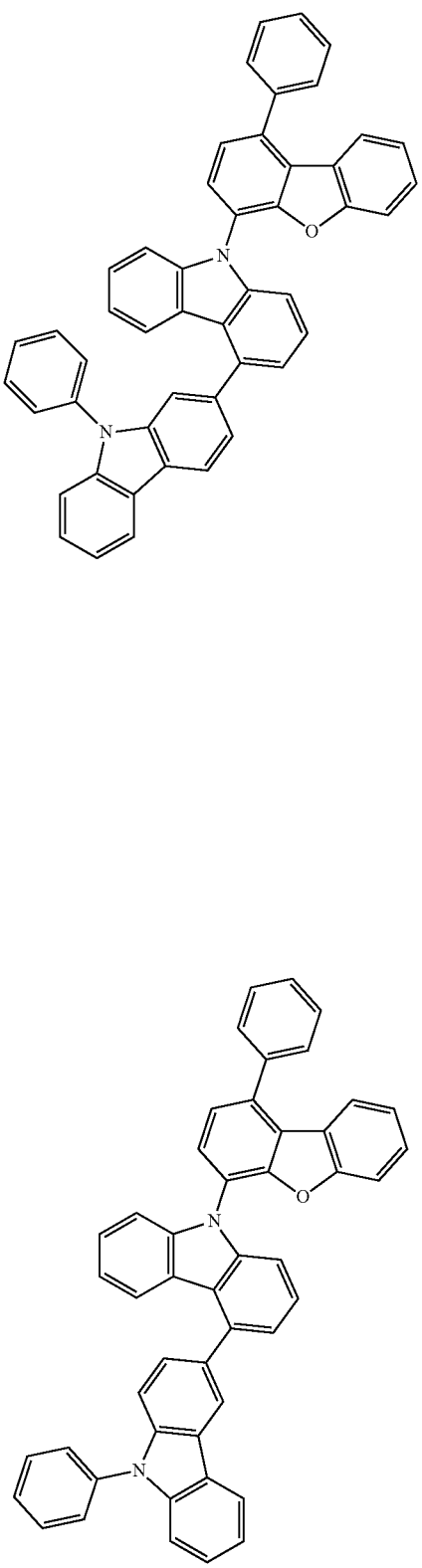

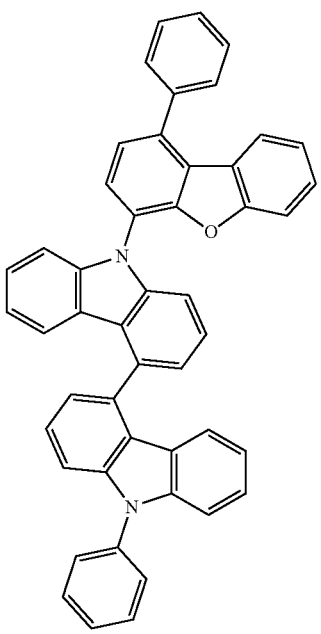
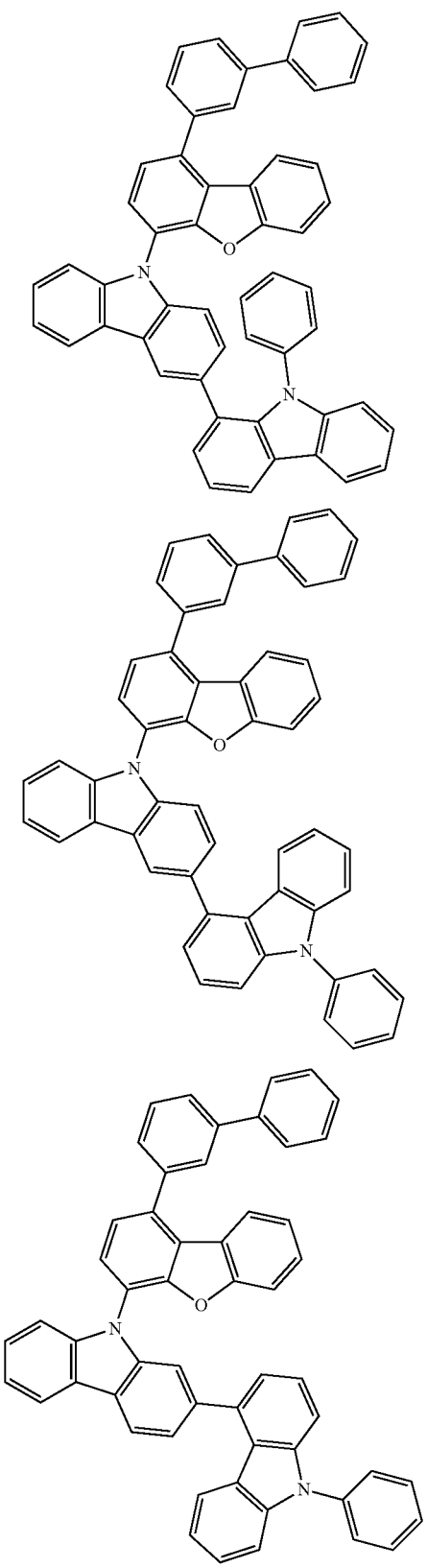

201
-continued
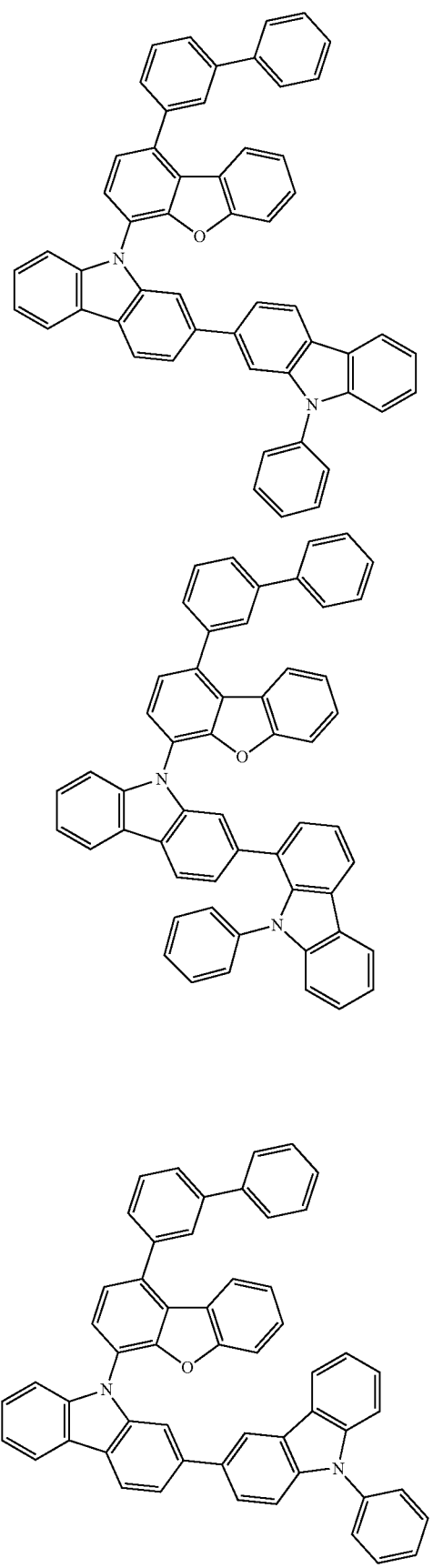
202
-continued
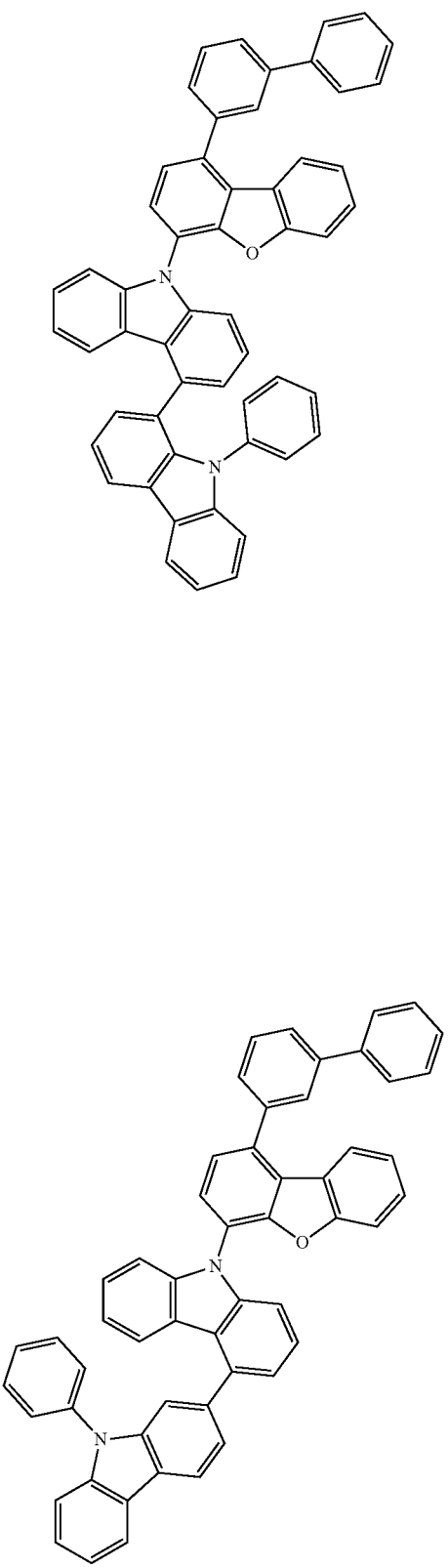

203
-continued
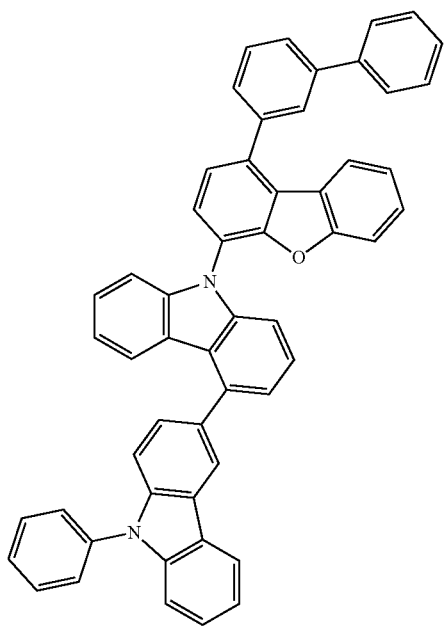
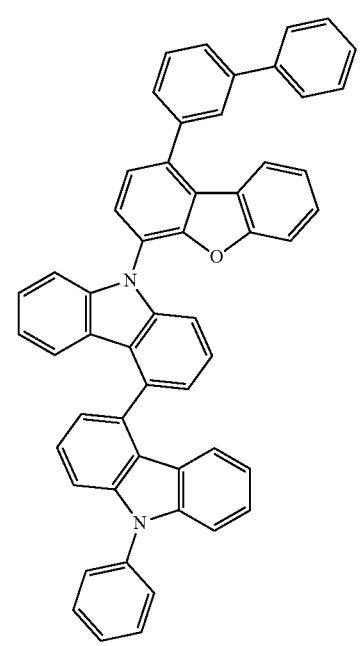
204
-continued
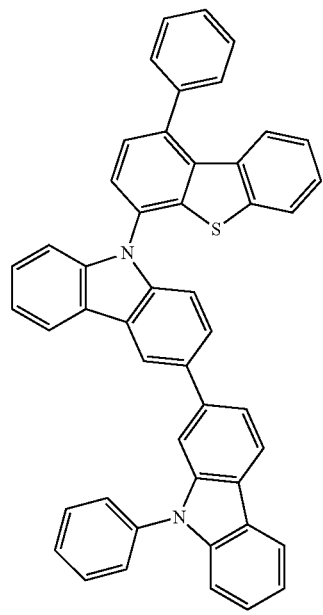
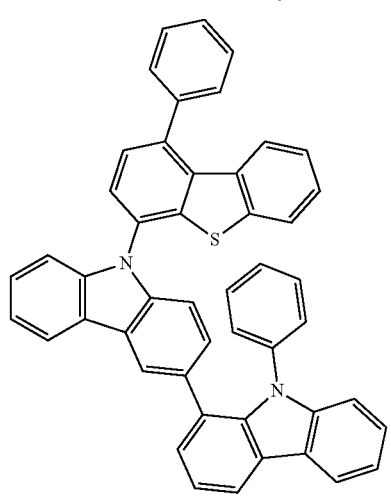
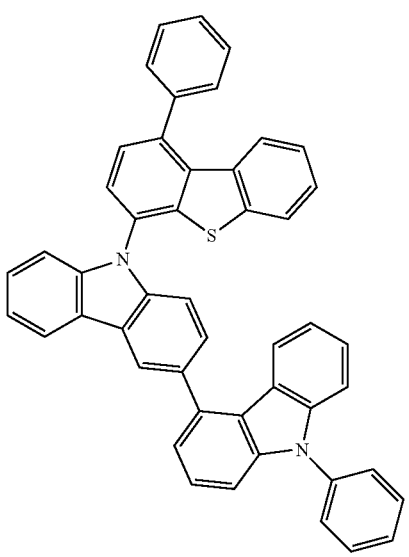

205
-continued
206
-continued
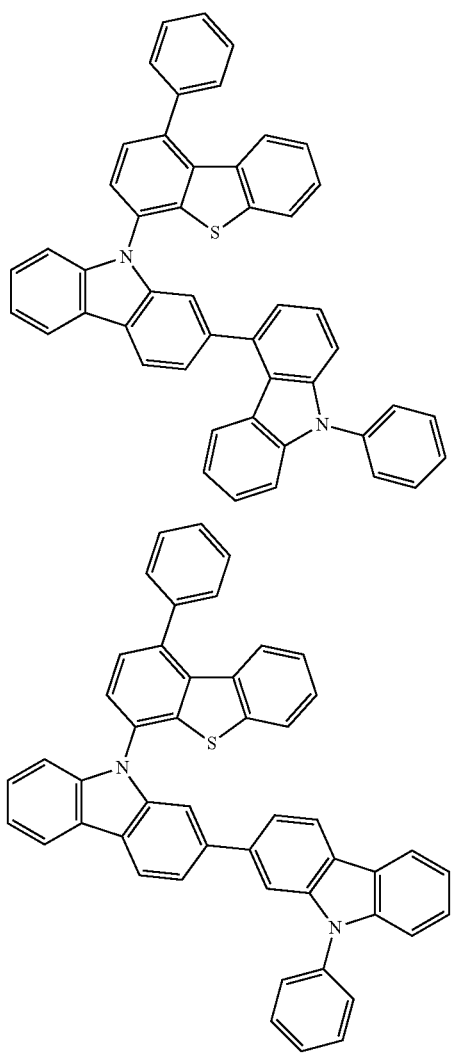
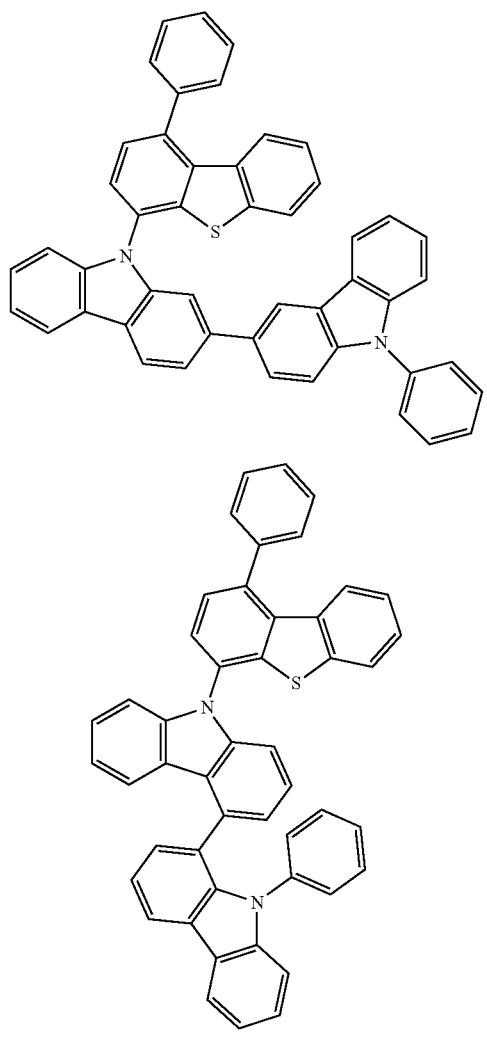
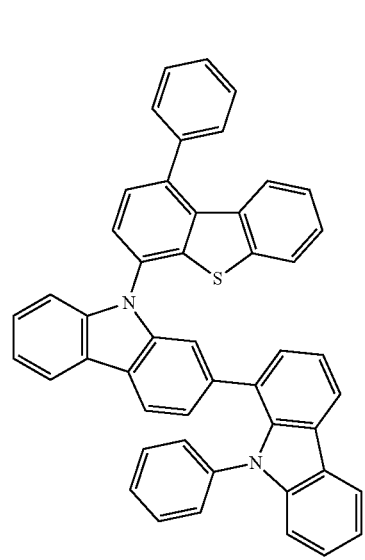

207
-continued
208
-continued
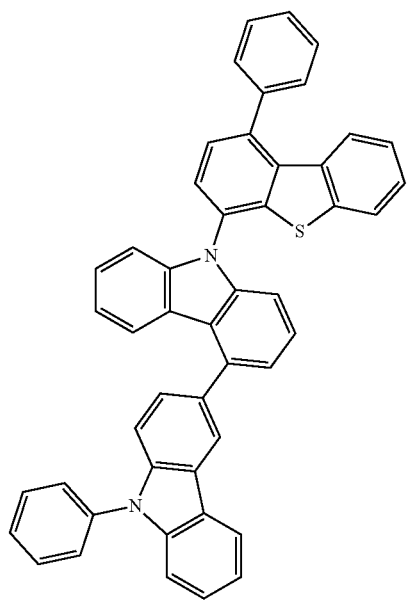
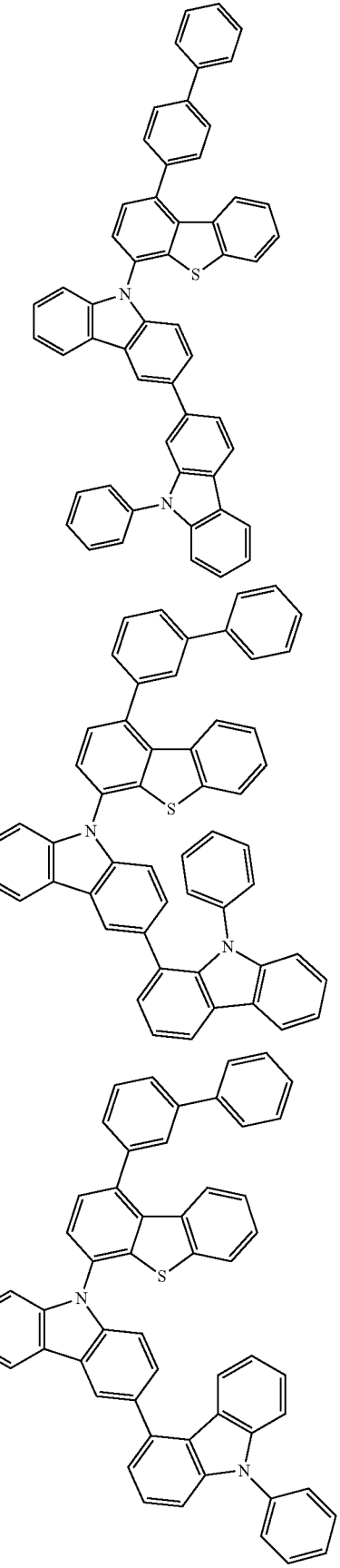

209
-continued
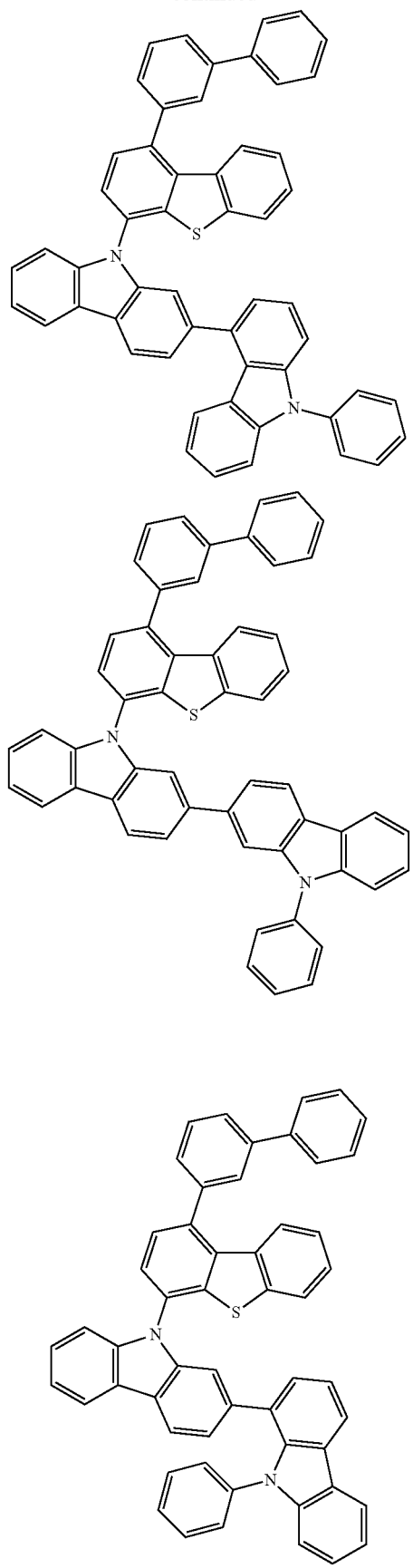
210
-continued
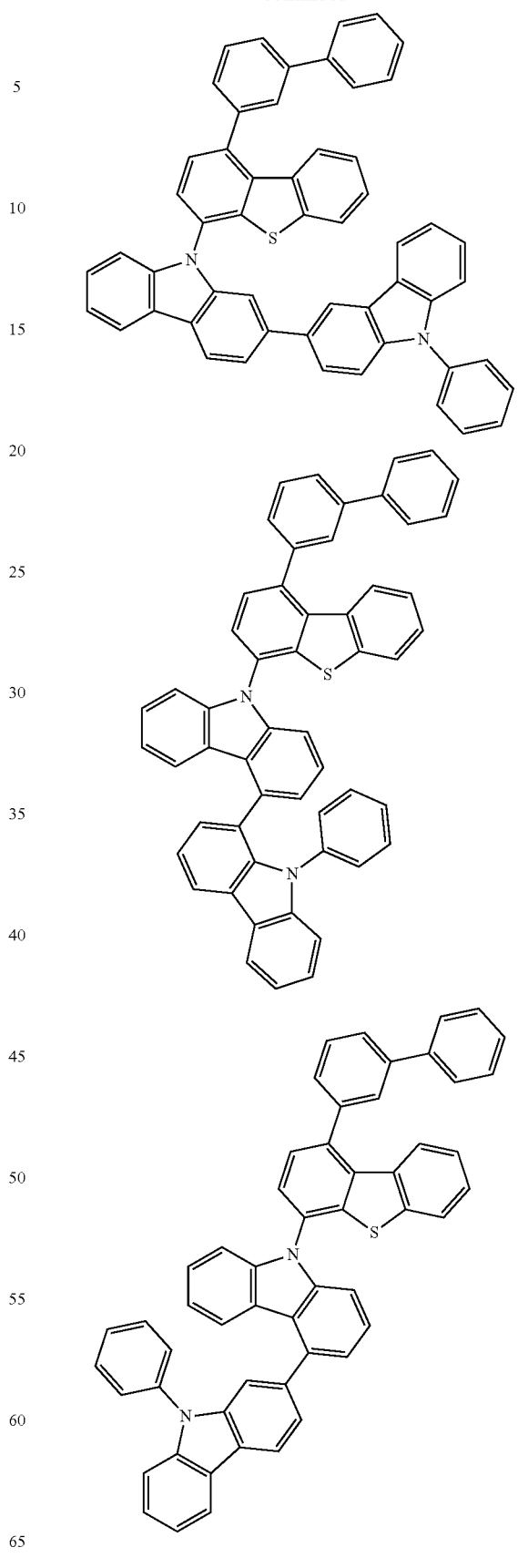

211
-continued
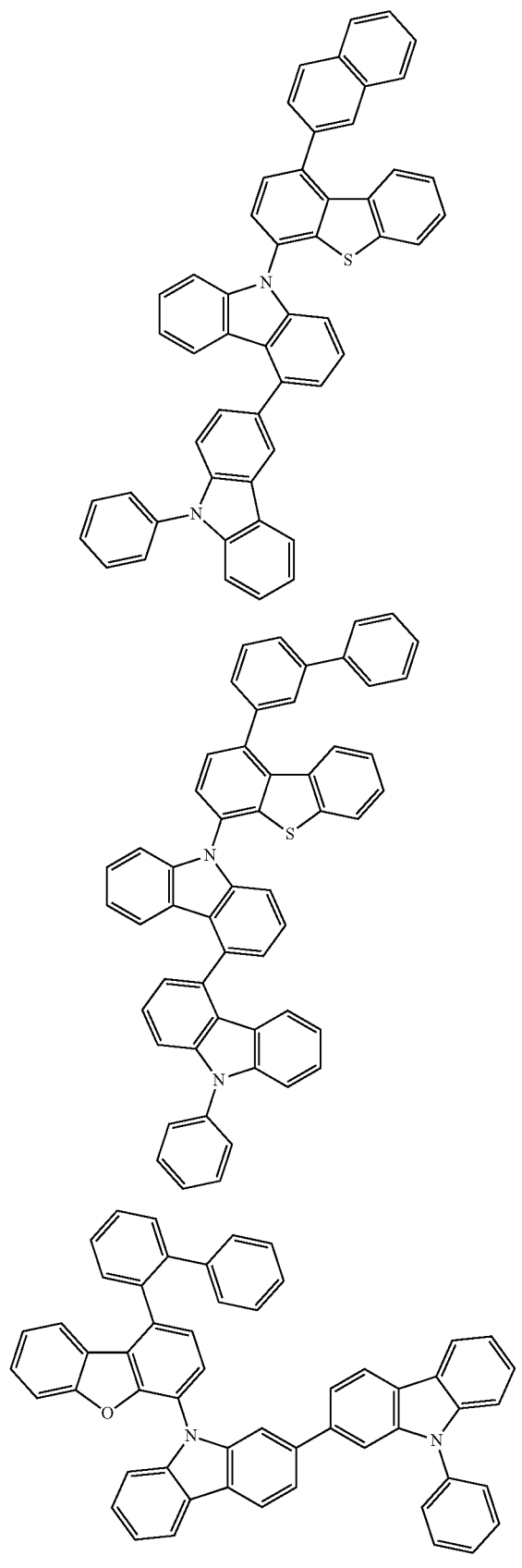
212
-continued
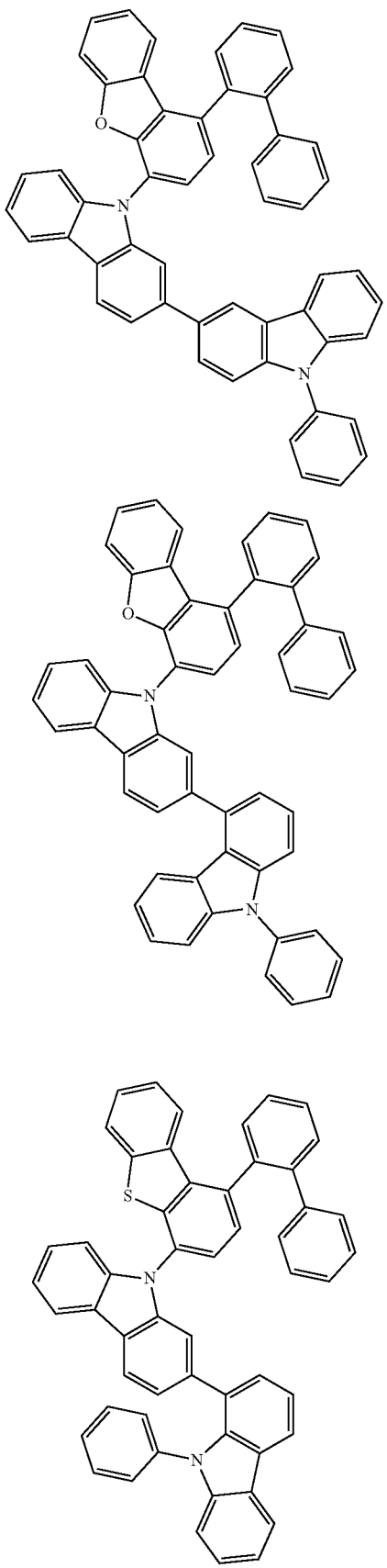

213
-continued
214
-continued
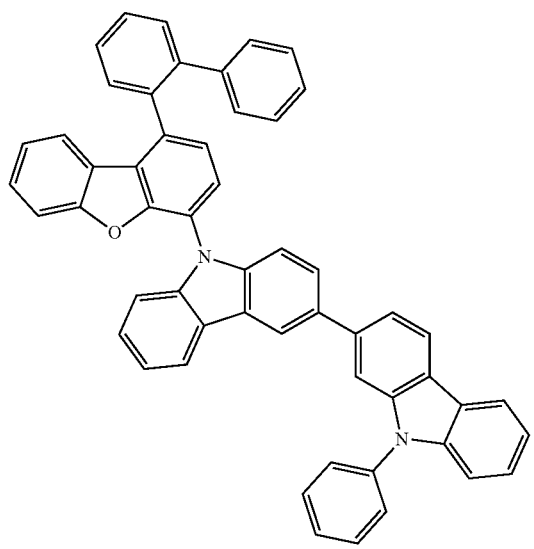
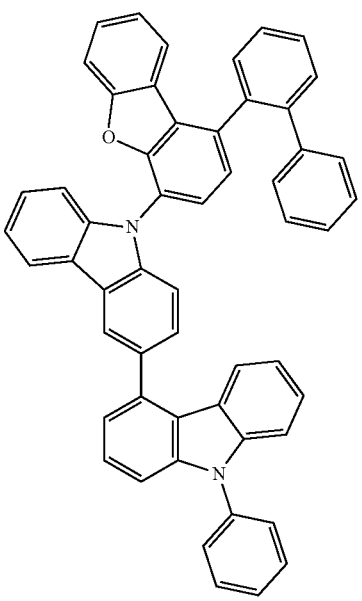
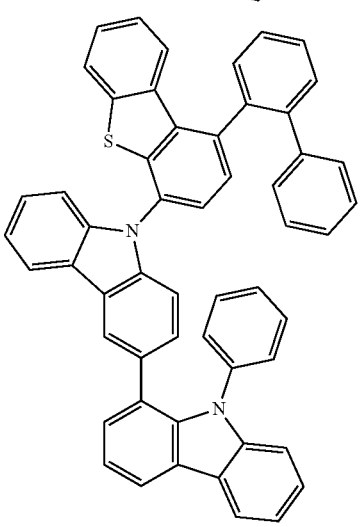
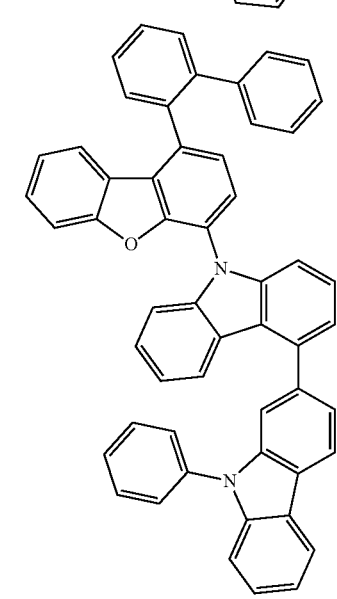

215
-continued
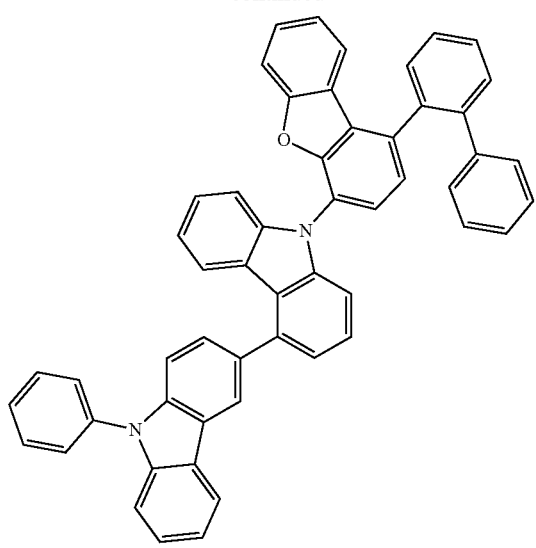
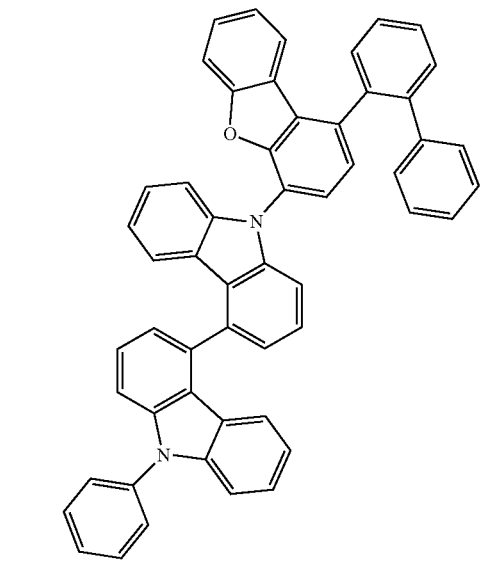
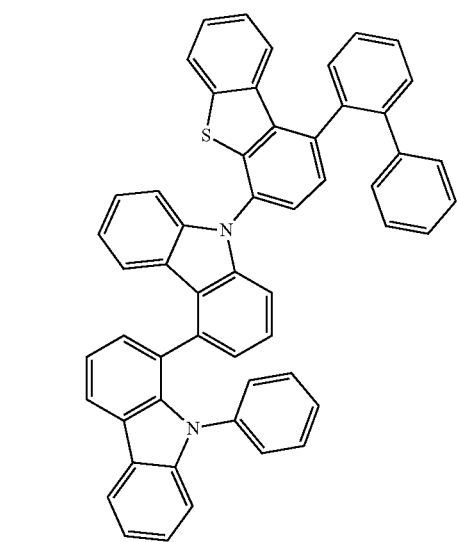
216
-continued
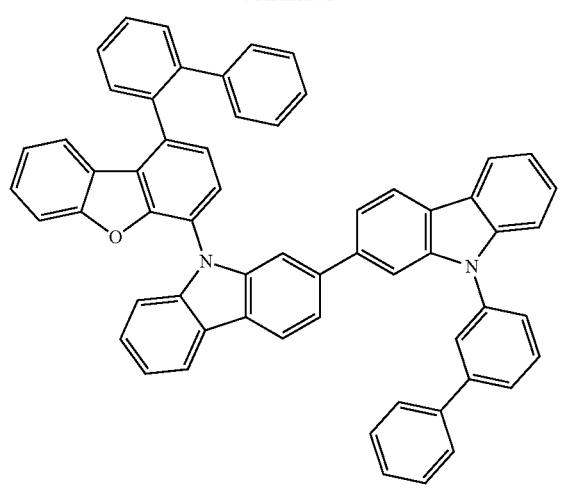
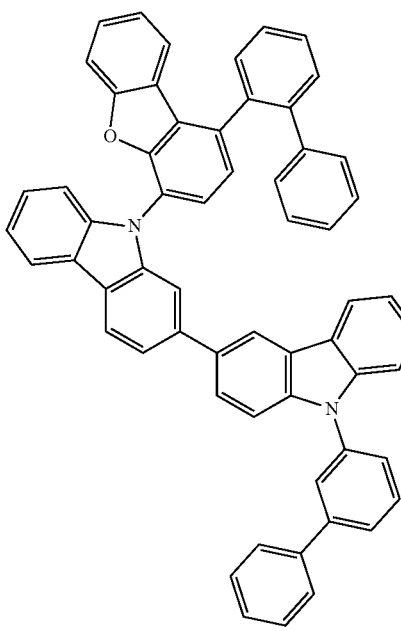

217
-continued
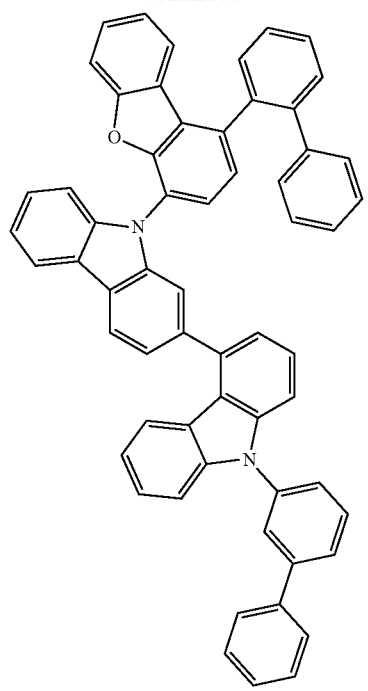
218
-continued
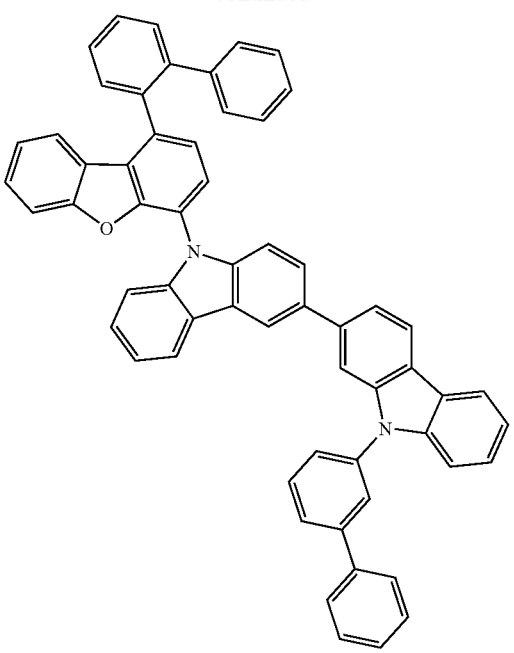
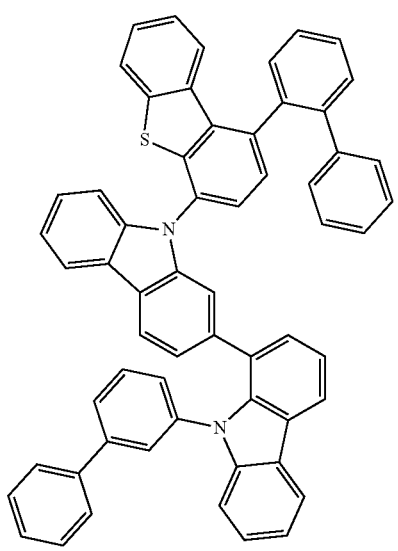
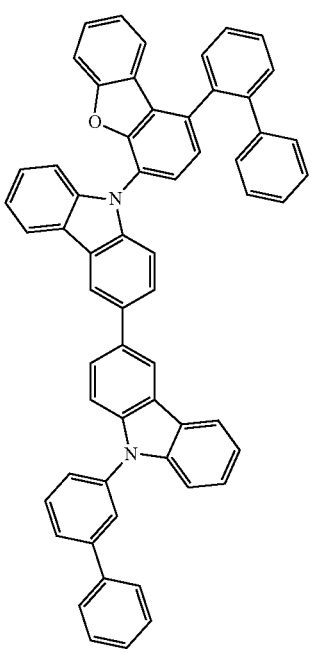

219
-continued
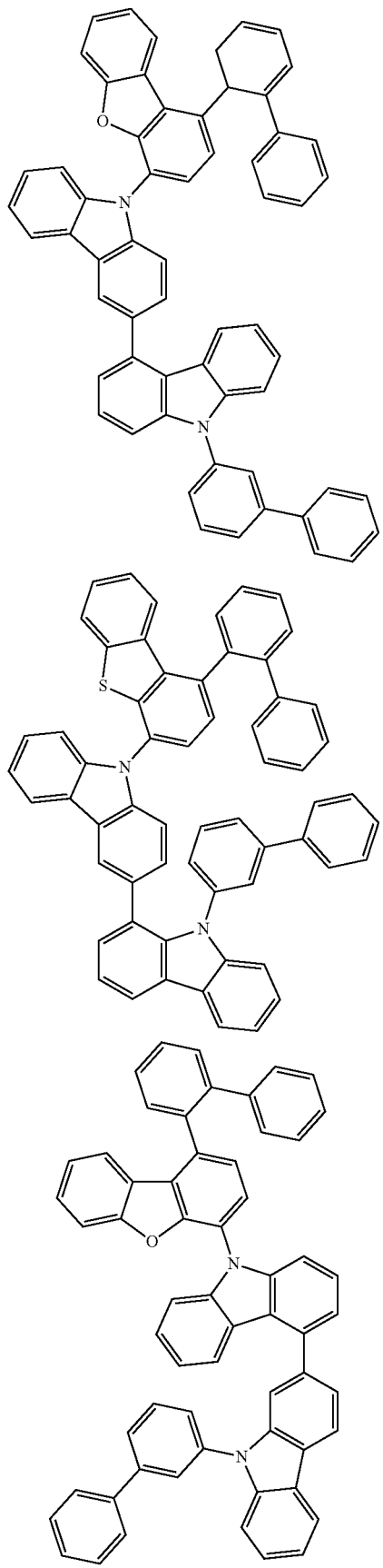
220
-continued
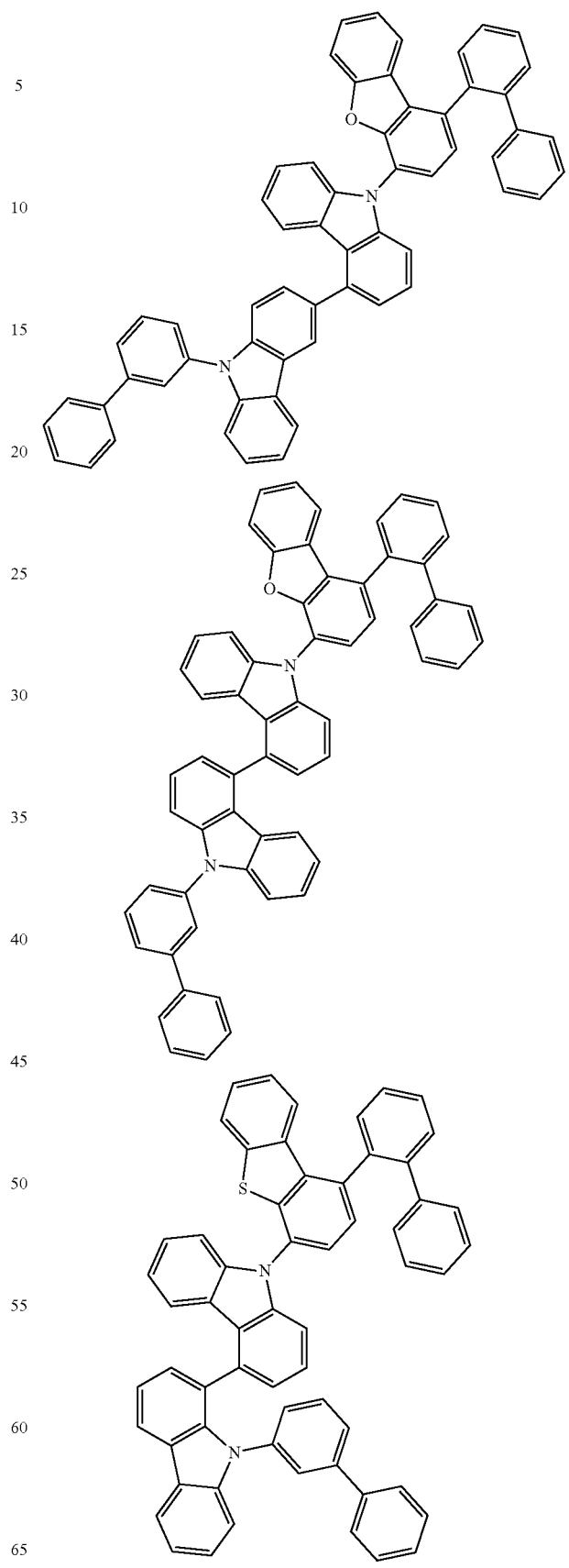

221
-continued
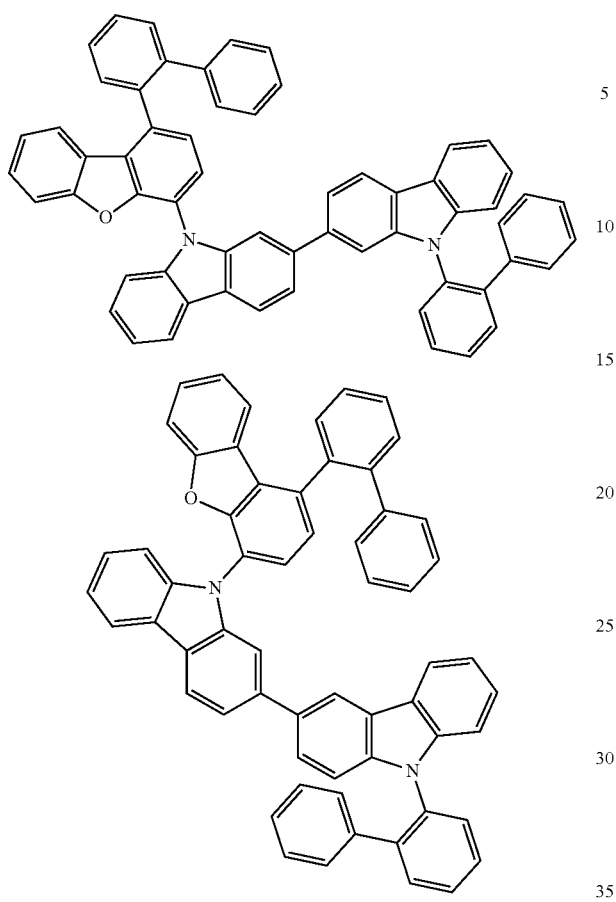
222
-continued
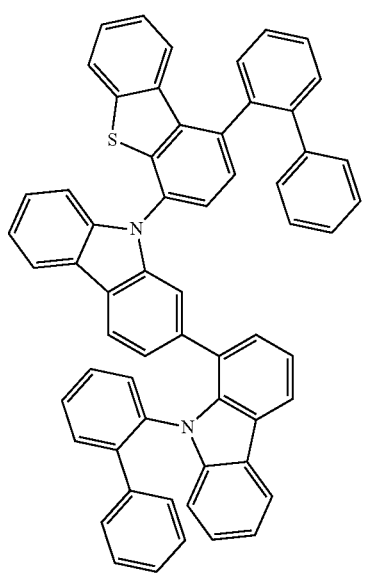
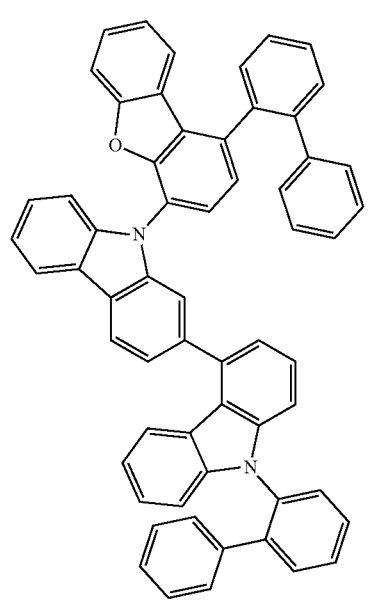
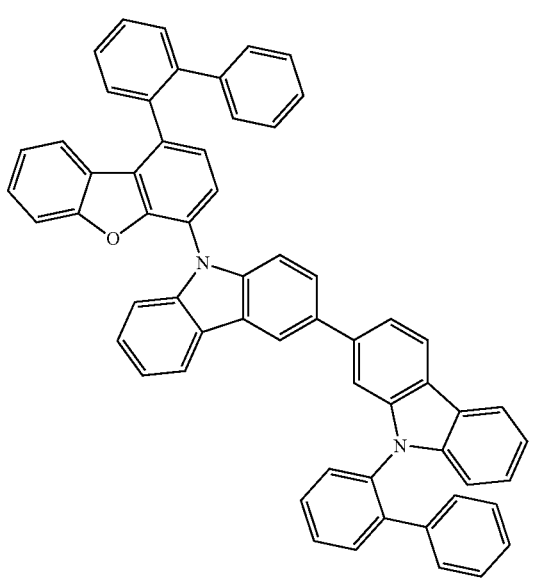

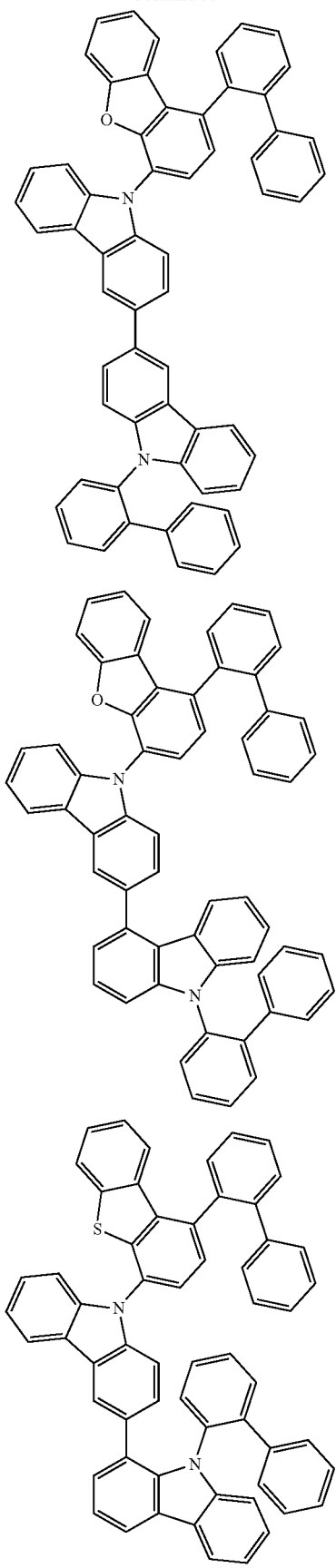
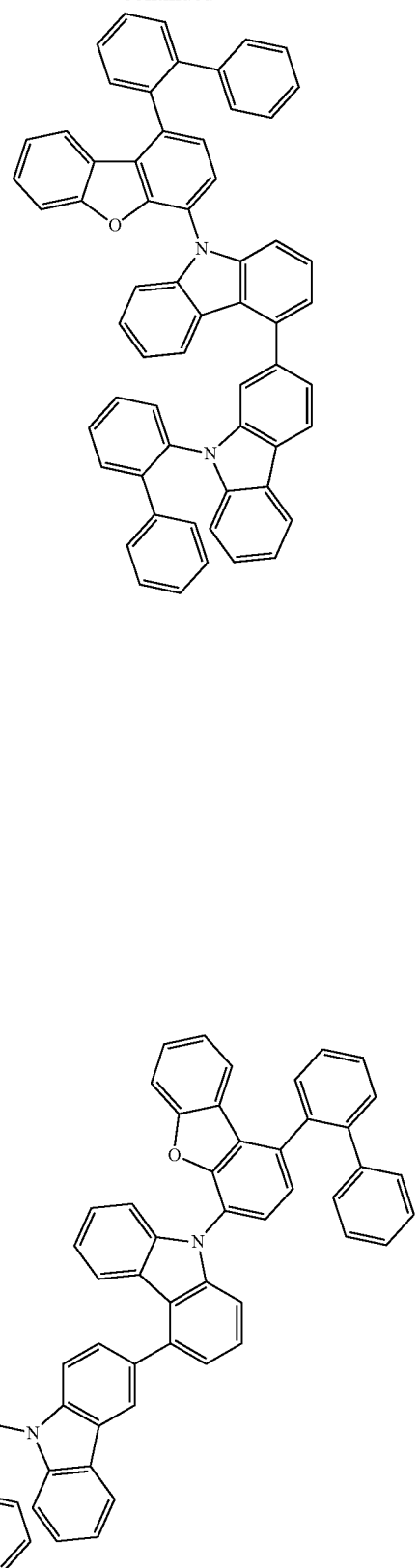

225
-continued
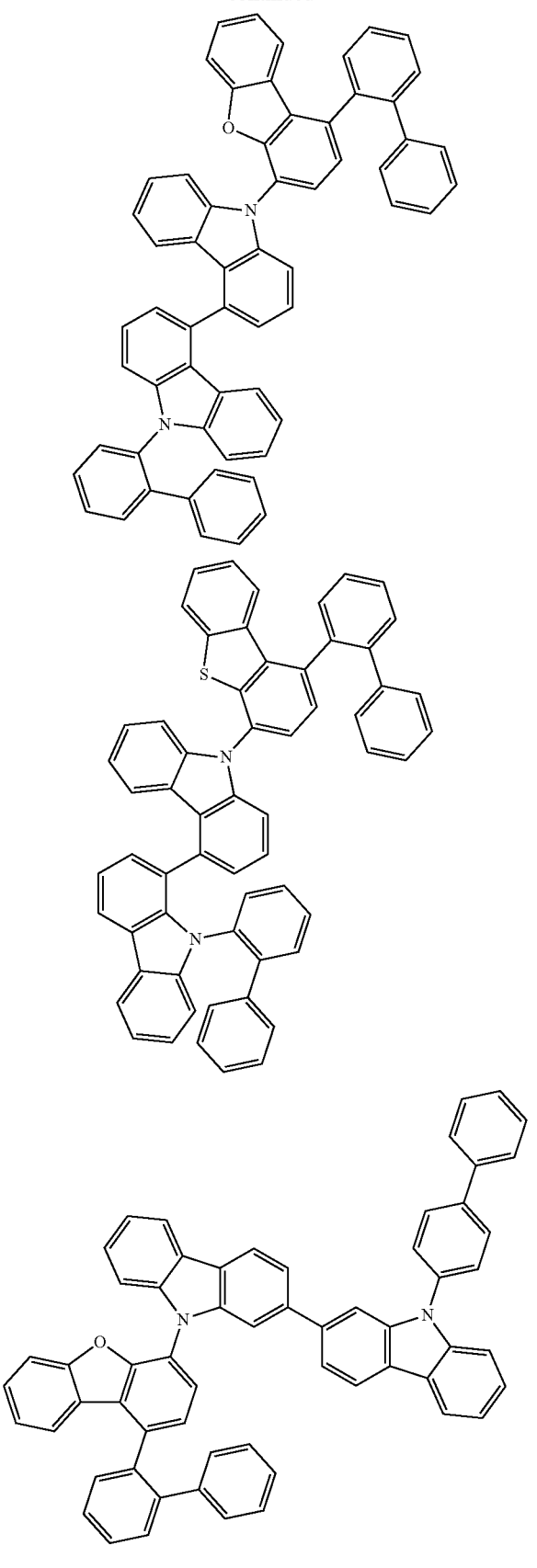
226
-continued
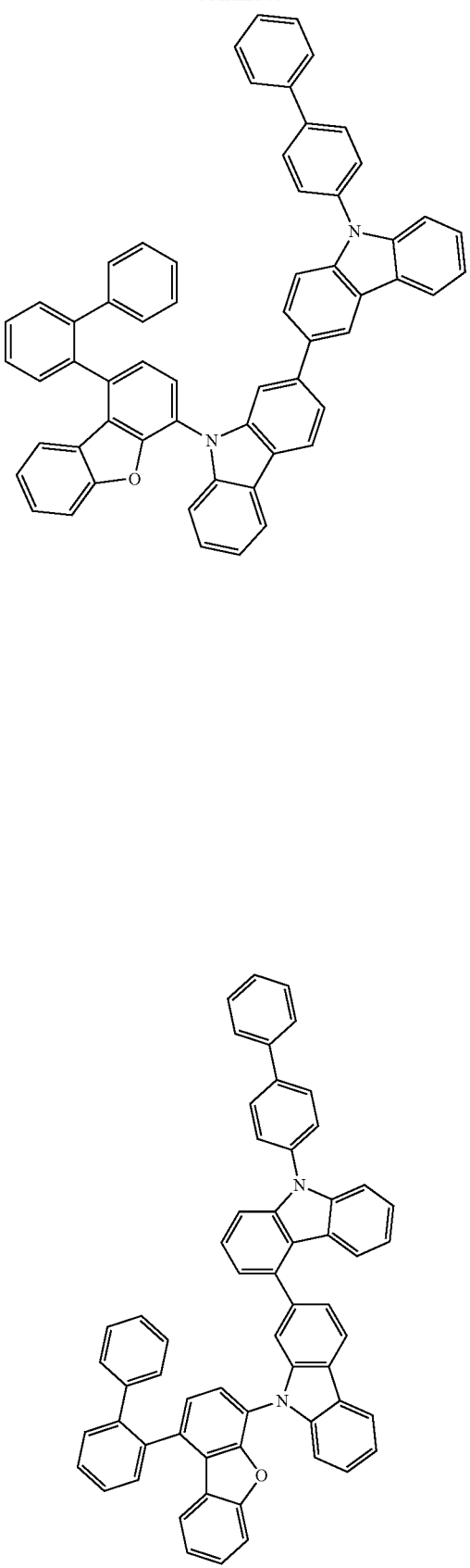

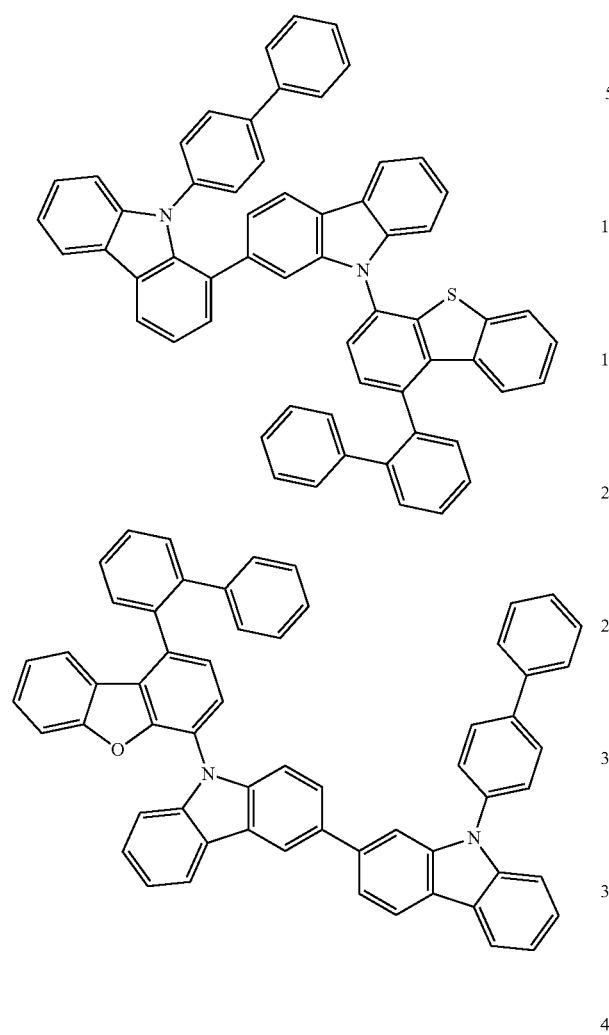
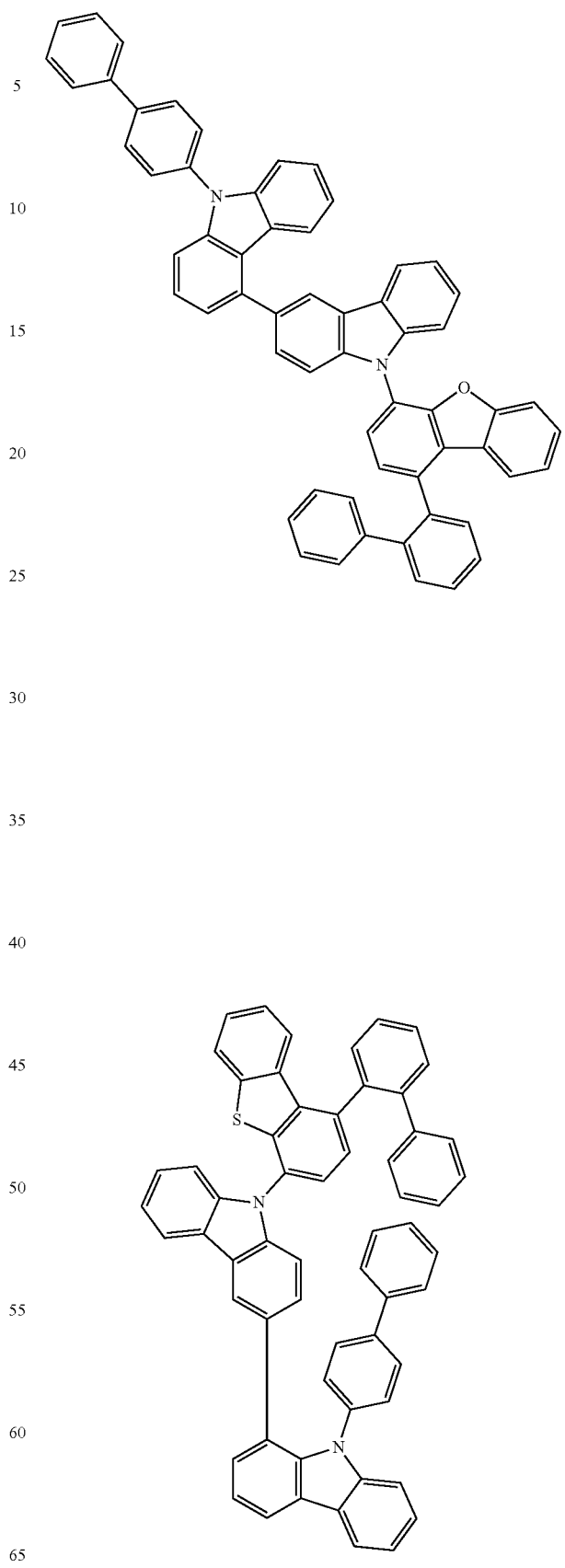

229
-continued
230
-continued
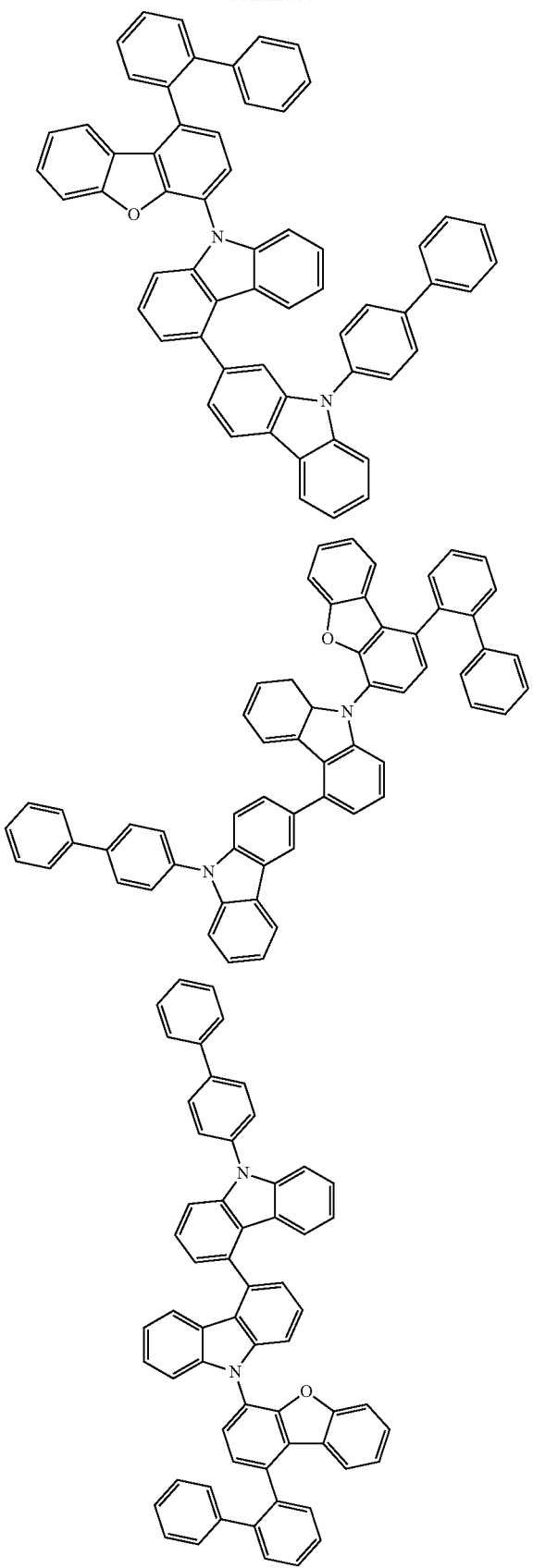
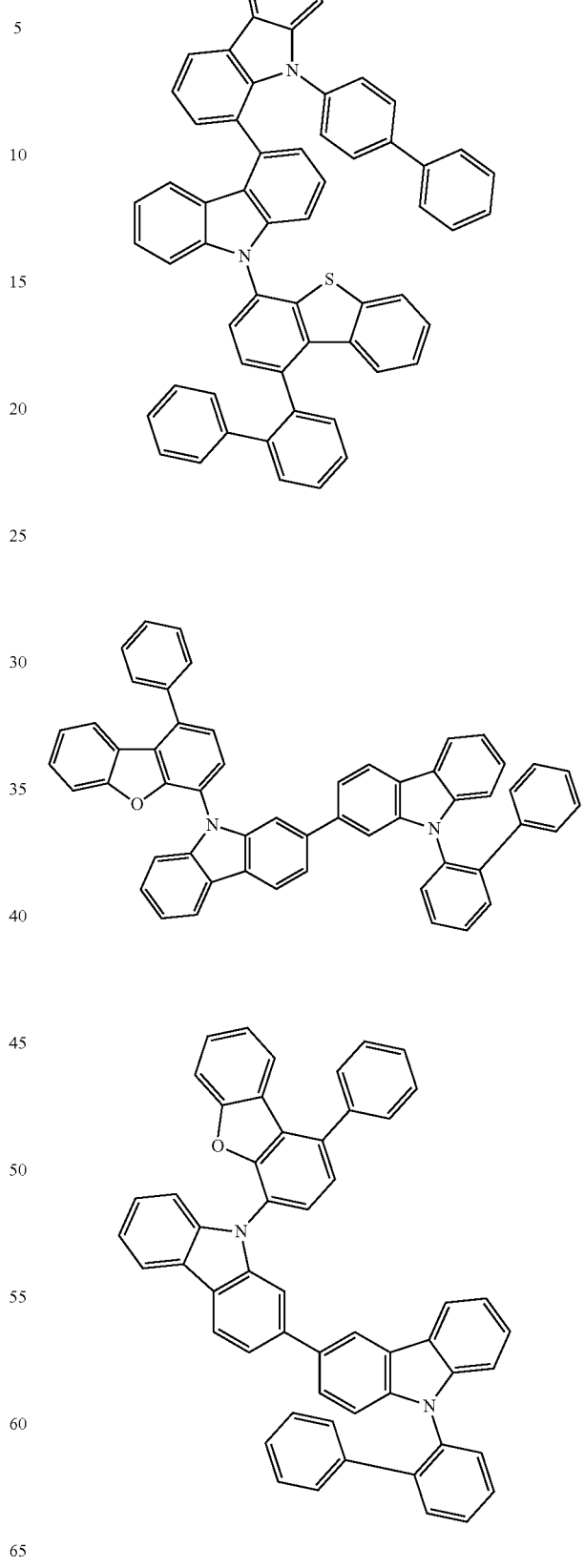

231
-continued
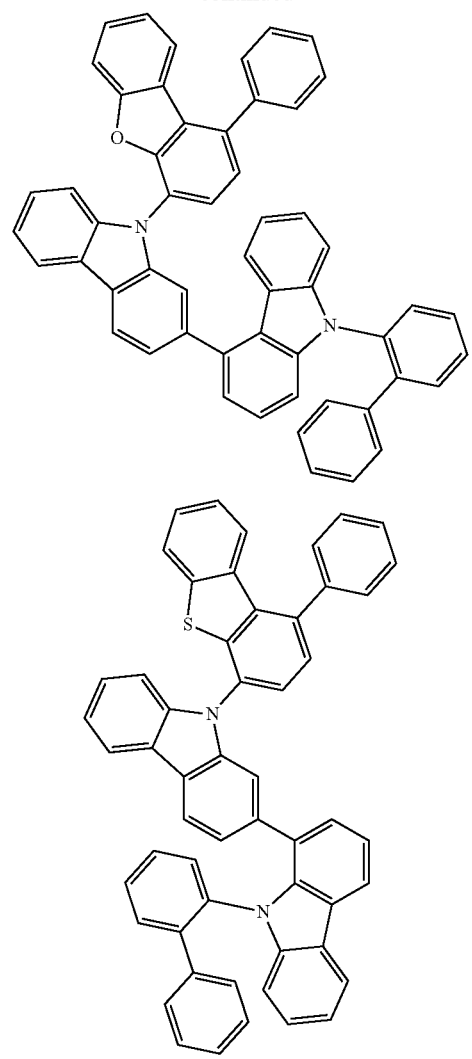
232
-continued
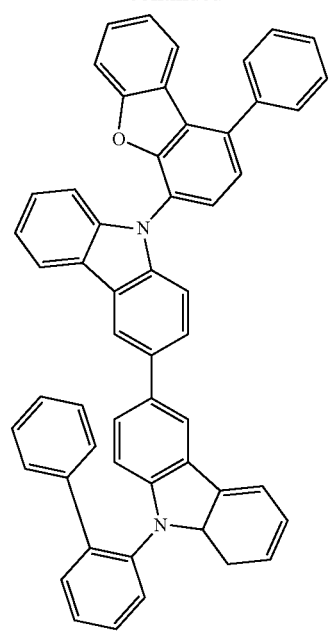
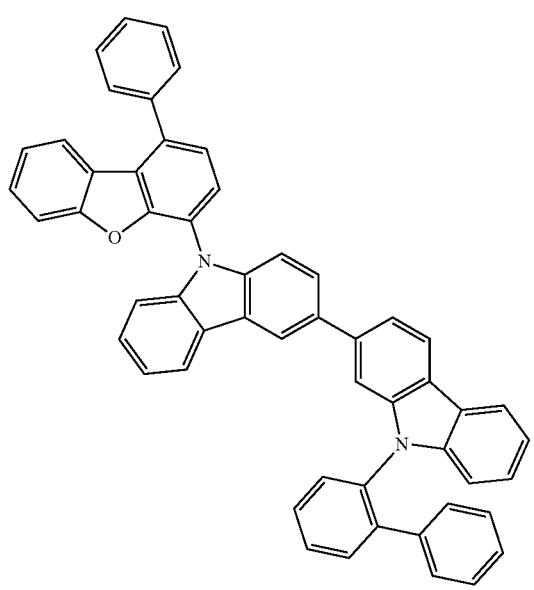
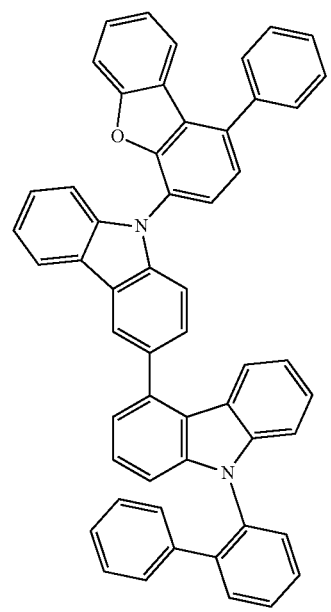

233
-continued
234
-continued
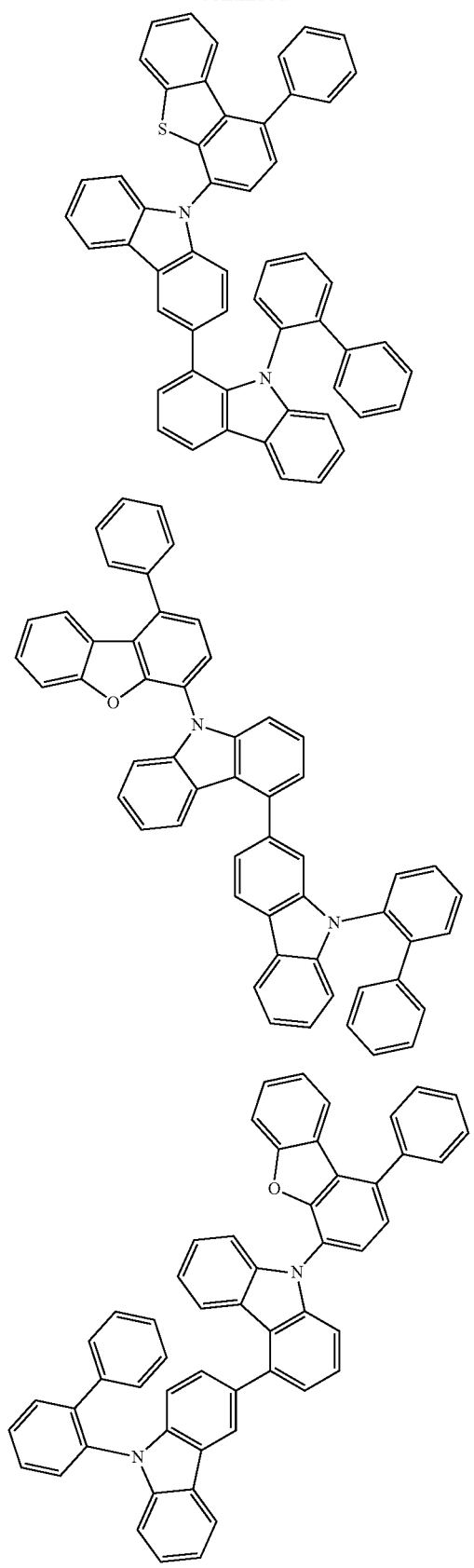
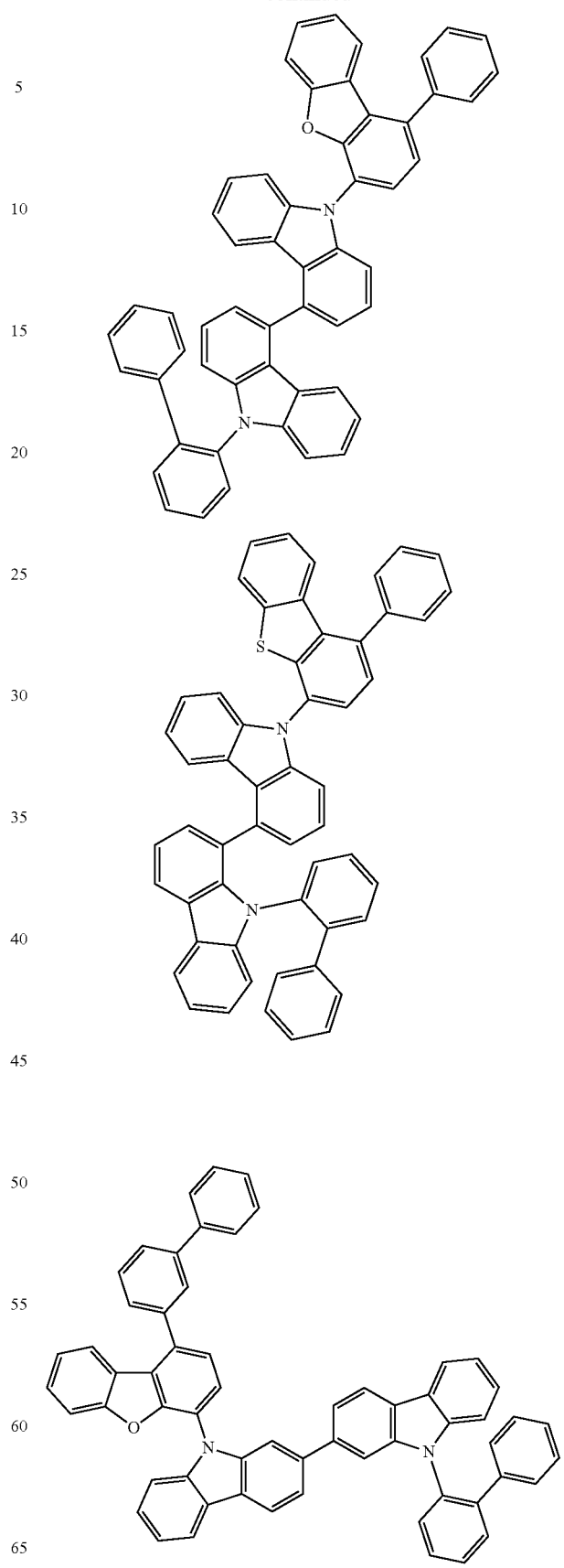

235
-continued
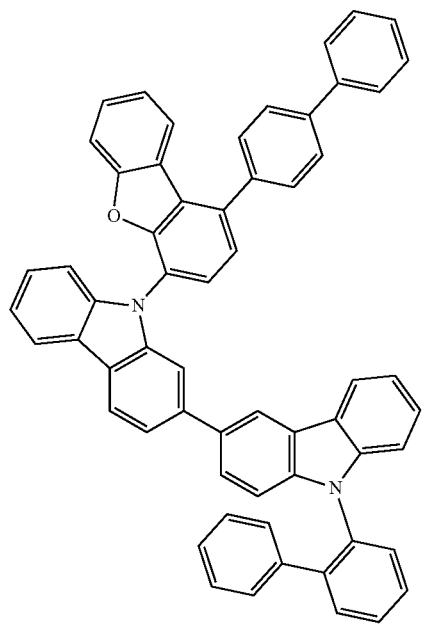
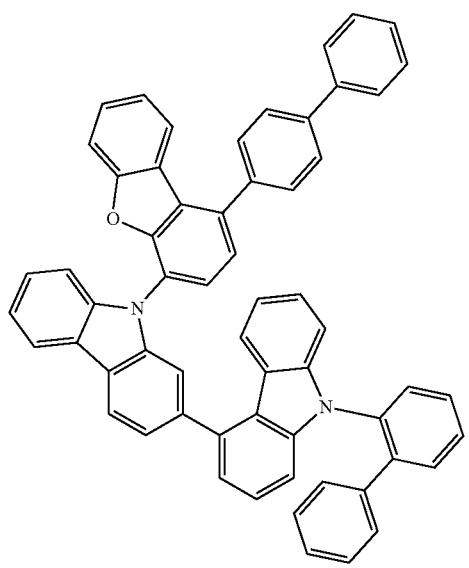
236
-continued
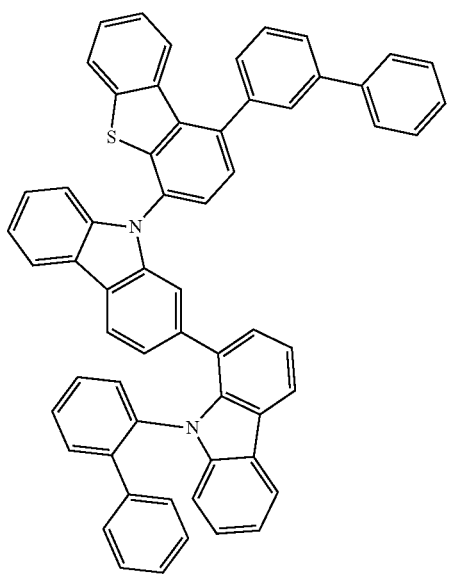
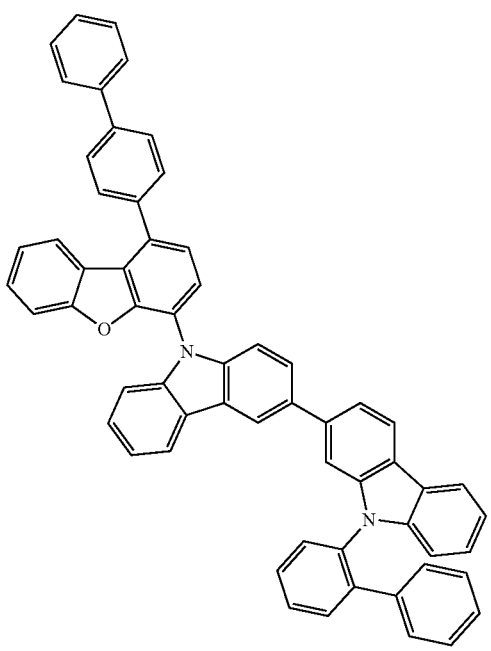

237
-continued
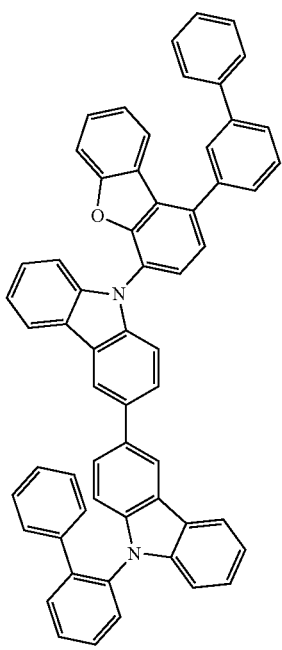
238
-continued
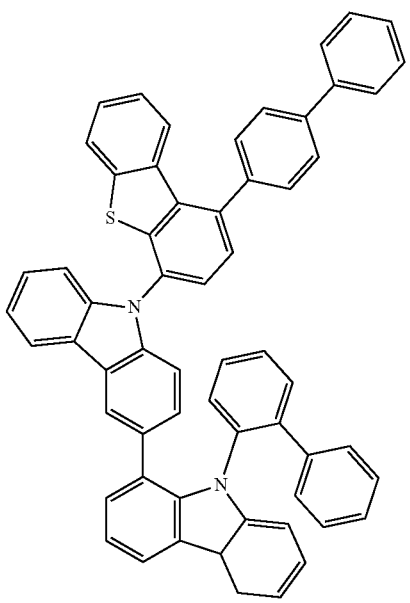
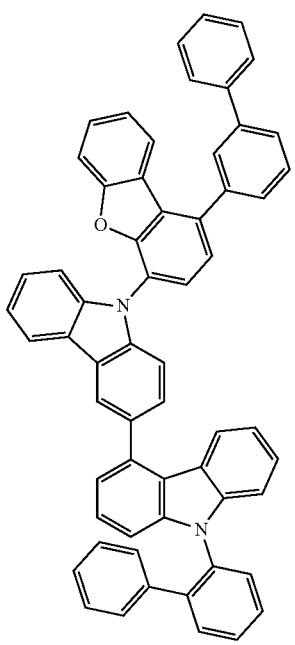
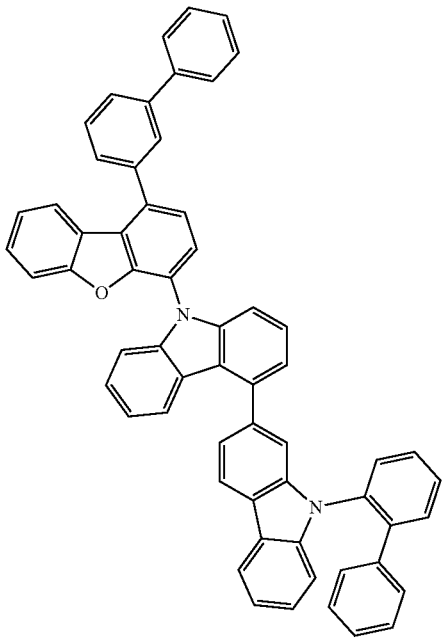

239
-continued
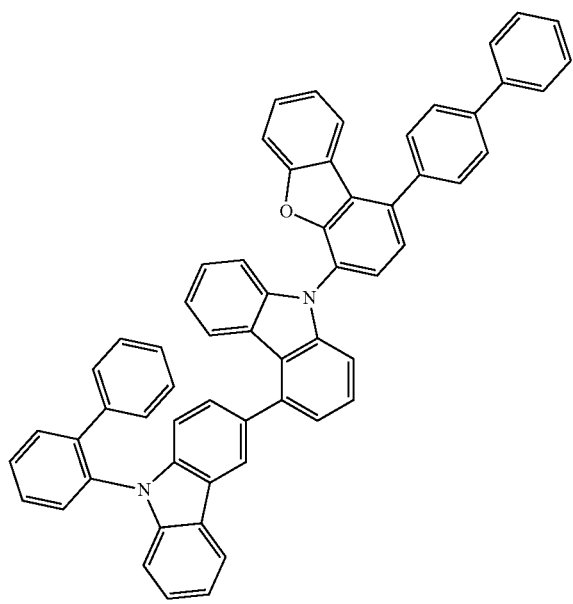
240
-continued
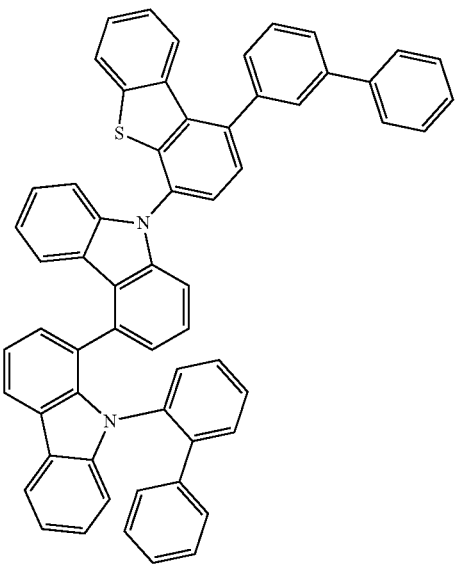
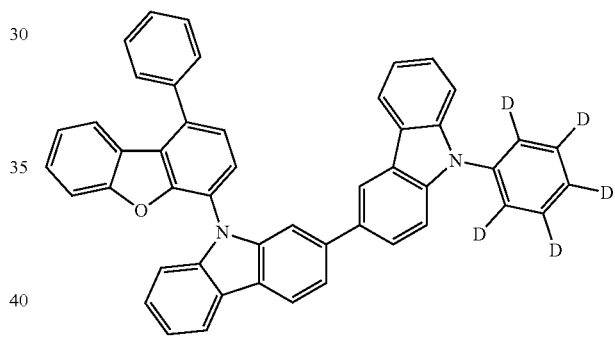
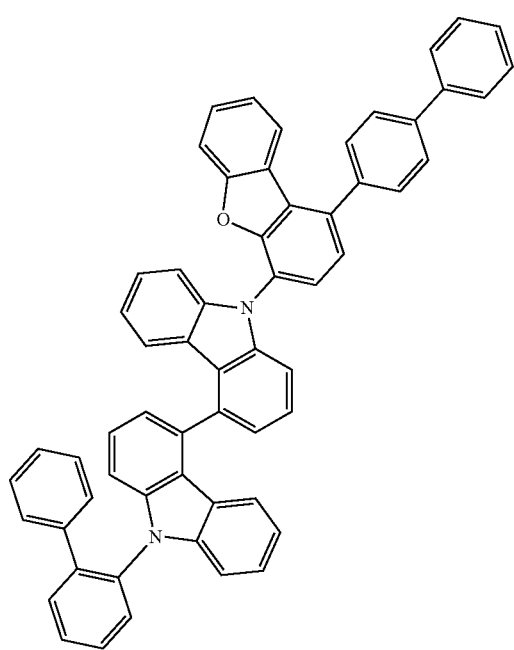
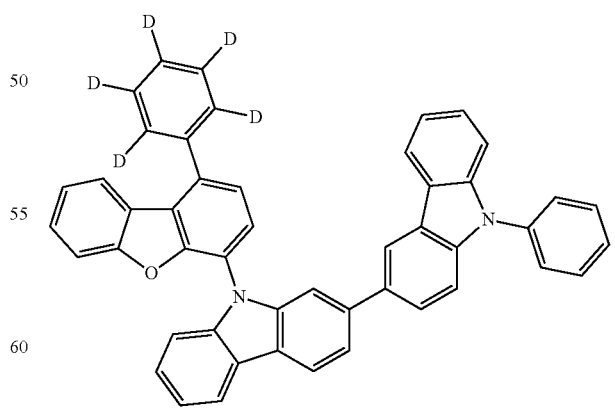

241
-continued
242
-continued
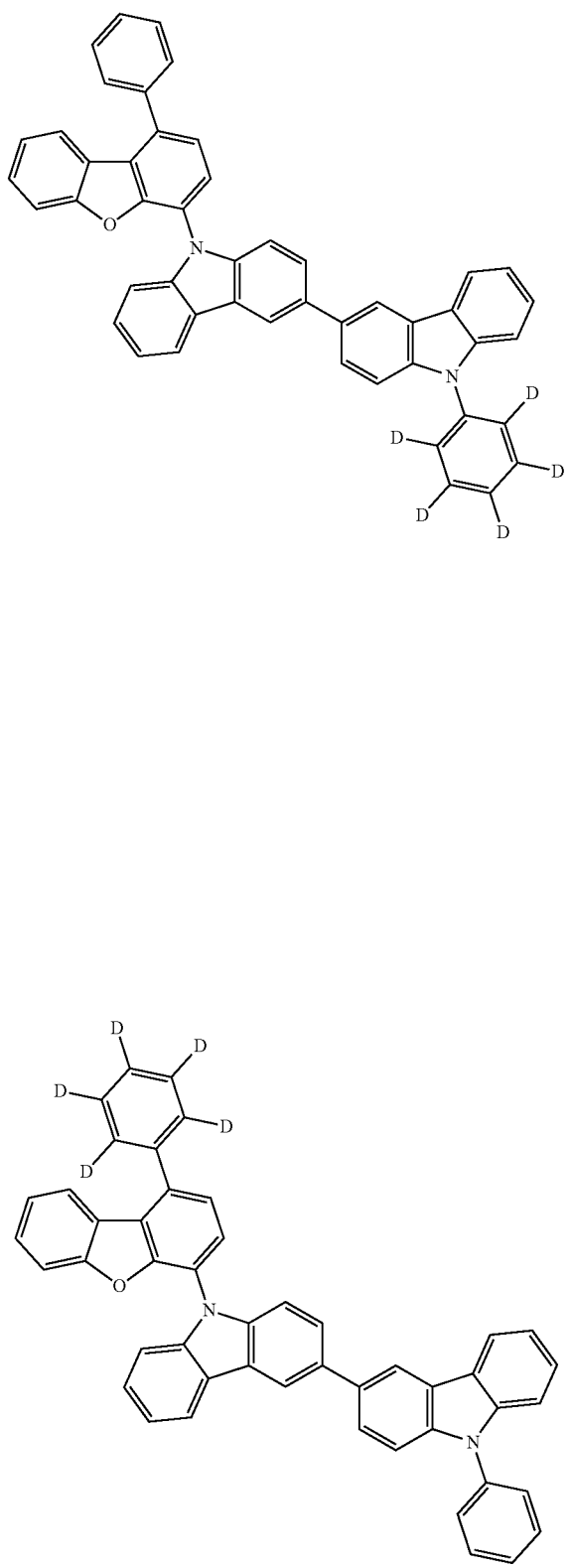
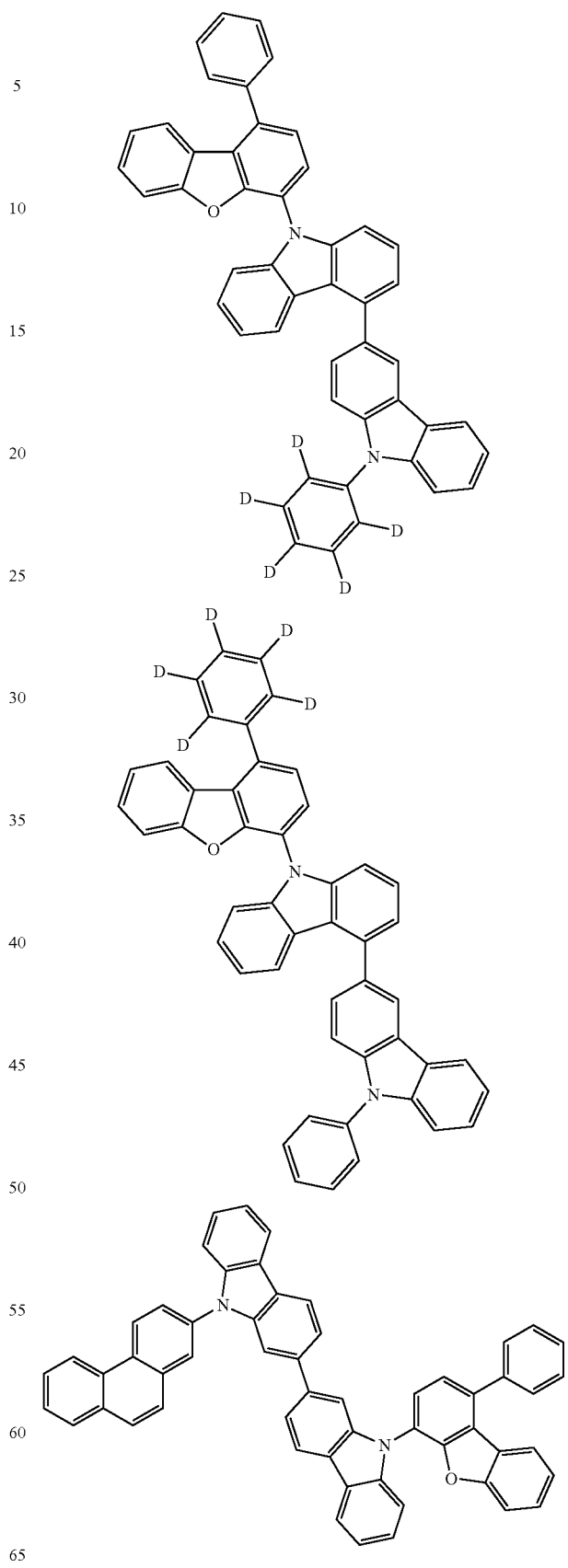

243
-continued
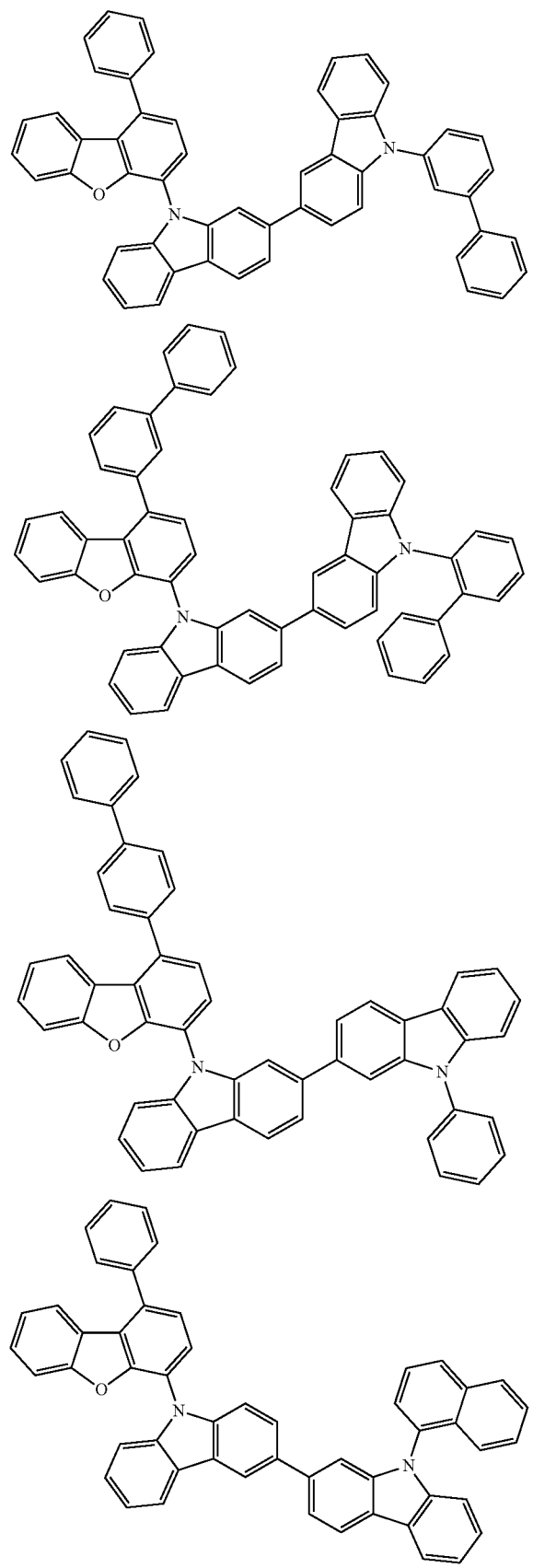
244
-continued
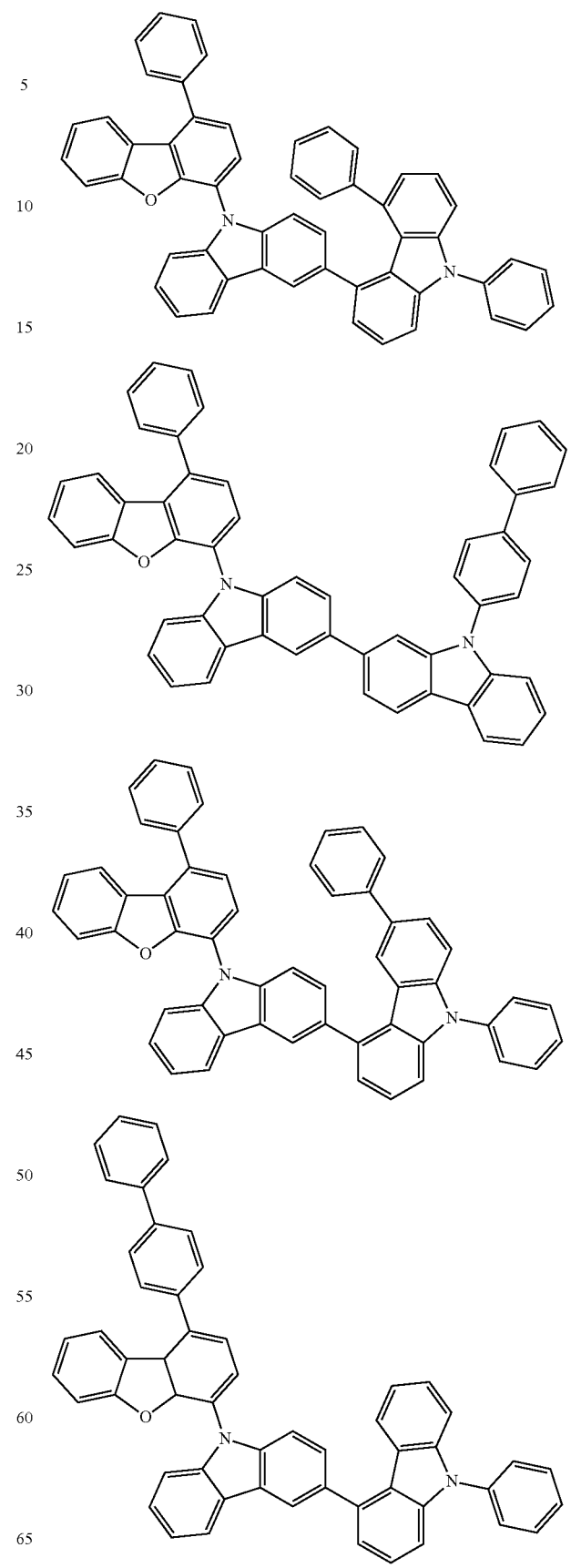

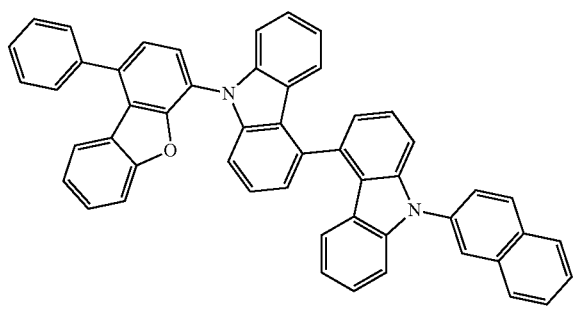
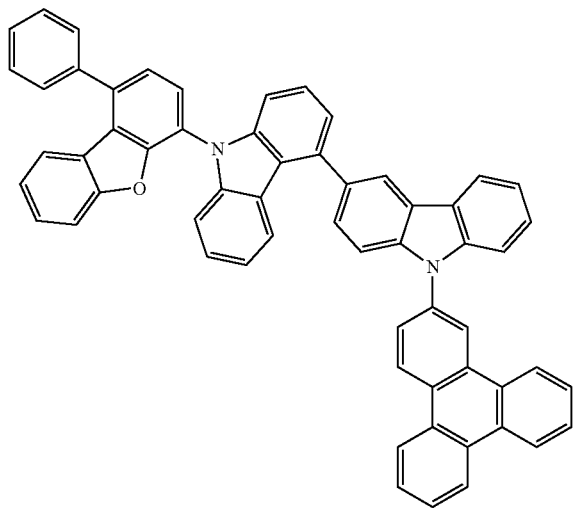
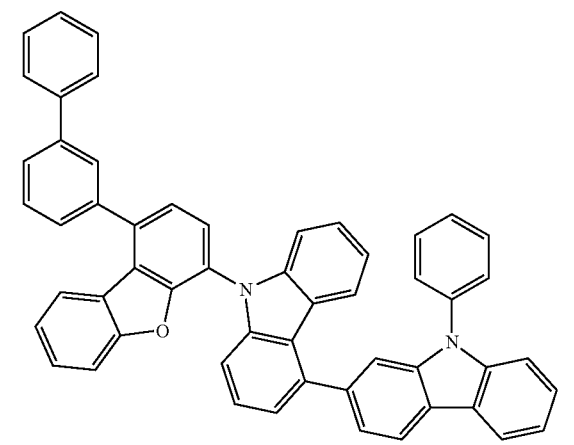
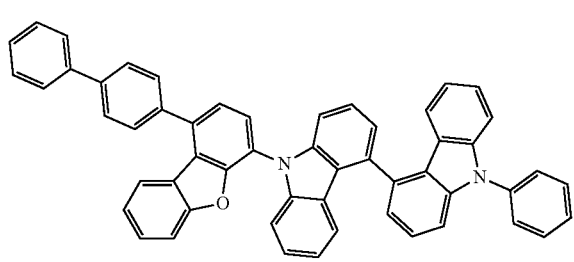
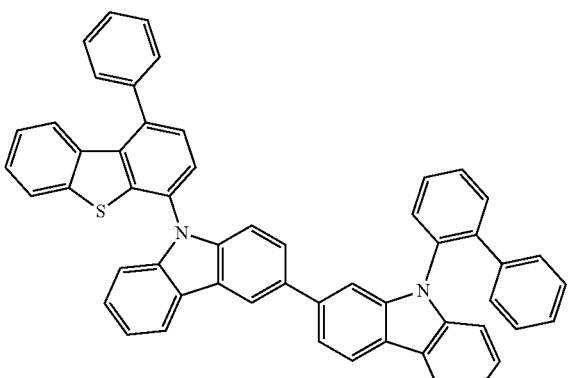
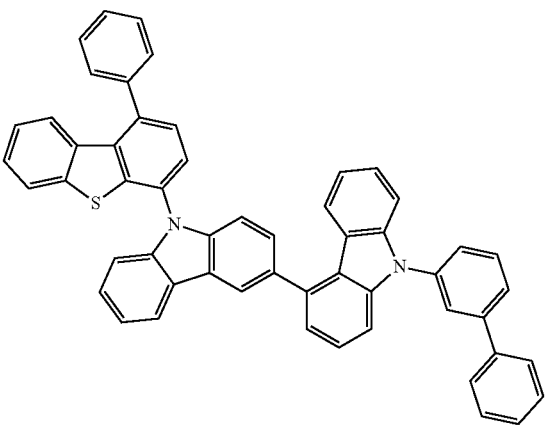
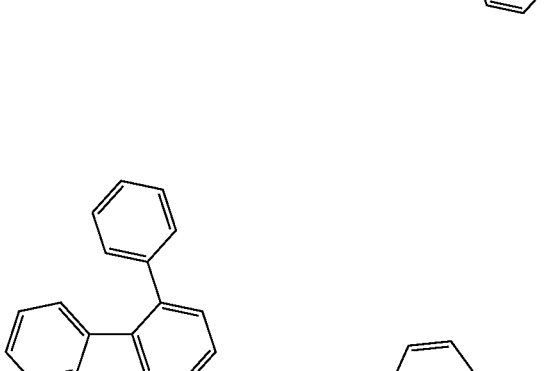
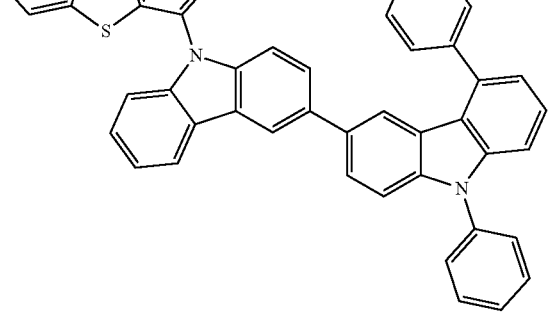

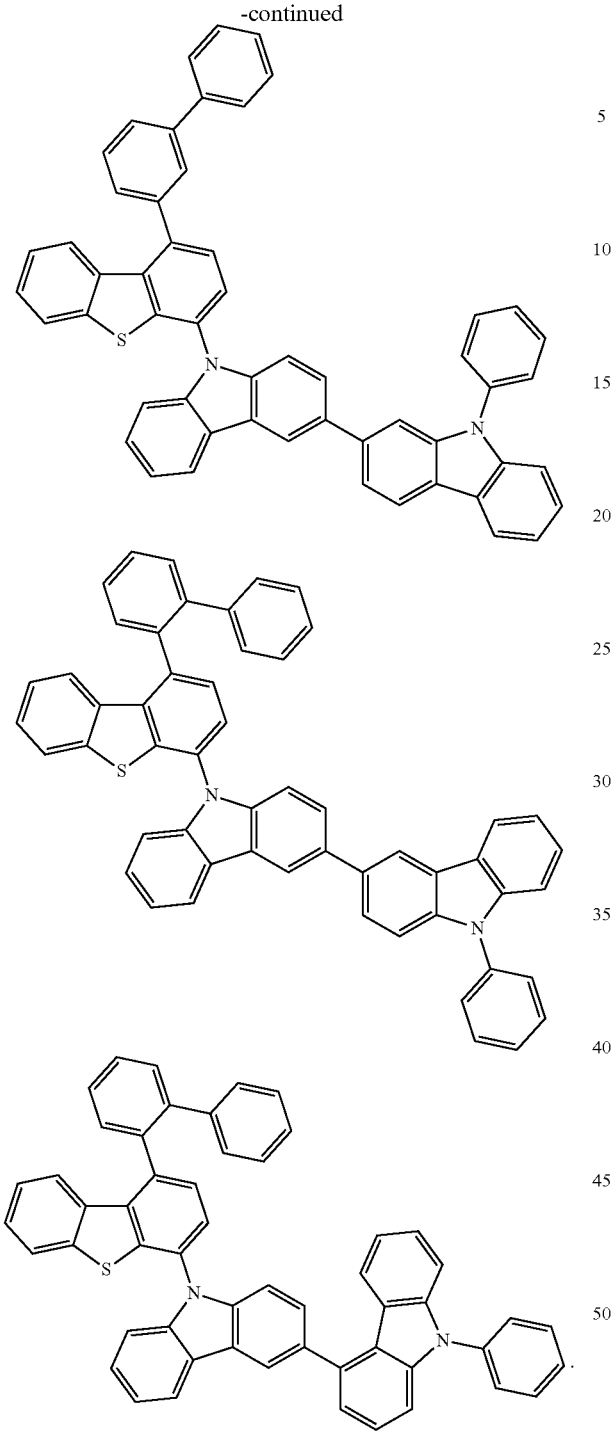

7. An organic light emitting device comprising:
a first electrode;
a second electrode provided opposite to the first electrode; and
one or more organic material layers provided between the first electrode and the second electrode,
wherein at least one of the organic material layers includes the compound of claim 1.

8. The organic light emitting device of claim 7, wherein the organic material layer includes a light emitting layer, and the light emitting layer includes the compound.

9. An organic light emitting device comprising:
a first electrode;
a second electrode provided opposite to the first electrode; and
one or more organic material layers provided between the first electrode and the second electrode,
wherein at least one of the organic material layer includes a hole injection layer, a hole transfer layer, or a hole injection and transfer layer, and the hole injection layer, the hole transfer layer, or the hole injection and transfer layer includes a compound of Chemical Formula 1:

Chemical Formula 1

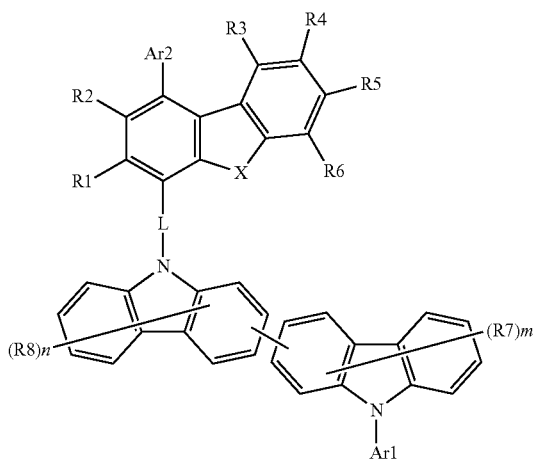

wherein, in Chemical Formula 1:
X is O or S;
L is a direct bond, a substituted or unsubstituted arylene group, or a substituted or unsubstituted heteroarylene group;
Ar1 is a substituted or unsubstituted aryl group or a substituted or unsubstituted heteroaryl group;
Ar2 is a substituted or unsubstituted aryl group having 6 to 30 carbon atoms;
R1 to R8 are the same as or different from each other, and each independently is hydrogen, a substituted or unsubstituted aryl group, or a substituted or unsubstituted heteroaryl group; and
m and n are each an integer of 0 to 7, and when m is 2 or greater, the R7s are the same as or different from each other, and when n is 2 or greater, the R8s are the same as or different from each other.

* * * * *